US005712381A

United States Patent [19]

Lin et al.

[11] Patent Number: 5,712,381
[45] Date of Patent: Jan. 27, 1998

[54] MADD, A TNF RECEPTOR DEATH DOMAIN LIGAND PROTEIN

[75] Inventors: Lih-Ling Lin, Concord; Jennifer Chen, Chestnut Hill; Andrea R. Schievella, Winchester; James Graham, Somerville, all of Mass.

[73] Assignee: Genetics Institute, Inc., Cambridge, Mass.

[21] Appl. No.: 698,551

[22] Filed: Aug. 15, 1996

Related U.S. Application Data

[63] Continuation-in-part of Ser. No. 602,228, Feb. 15, 1996, which is a continuation-in-part of Ser. No. 533,901, Sep. 26, 1995, which is a continuation-in-part of Ser. No. 494,440, Jun. 19, 1995, which is a continuation-in-part of Ser. No. 327,514, Oct. 19, 1994, abandoned.

[51] Int. Cl.$^6$ .................. C07M 21/04; C12N 15/12; C12N 15/85; C07K 14/715

[52] U.S. Cl. .................. 536/23.5; 536/23.5; 435/69.1; 435/325; 435/70.1; 435/320.1; 530/350; 530/300

[58] Field of Search .................. 435/69.1, 7.1, 435/70.1, 325, 320.1; 530/350, 300; 536/23.5

[56] References Cited

U.S. PATENT DOCUMENTS

| 5,296,592 | 3/1994 | Dower et al. | 530/413 |
|---|---|---|---|
| 5,506,340 | 4/1996 | Heavner | 530/324 |
| 5,563,039 | 10/1996 | Goeddel et al. | 435/7.1 |

FOREIGN PATENT DOCUMENTS

| A-46127/93 | 9/1993 | Australia. |
|---|---|---|
| 308378 | 9/1987 | European Pat. Off.. |
| 393438 | 4/1989 | European Pat. Off.. |
| 433900 | 12/1990 | European Pat. Off.. |
| 526905 | 8/1992 | European Pat. Off.. |
| 568924 | 4/1993 | European Pat. Off.. |
| 0 585 939 A2 | 9/1993 | European Pat. Off.. |
| WO 91/03533 | 8/1990 | WIPO. |
| WO 92/03470 | 3/1992 | WIPO. |
| WO 92/03471 | 3/1992 | WIPO. |
| WO 92/14834 | 9/1992 | WIPO. |
| WO 93/19777 | 3/1993 | WIPO. |
| WO 94/01548 | 1/1994 | WIPO. |
| WO 94/10207 | 5/1994 | WIPO. |
| WO 95/31544 | 11/1995 | WIPO. |
| WO 95/33051 | 12/1995 | WIPO. |
| WO 96/25941 | 8/1996 | WIPO. |

OTHER PUBLICATIONS

Luban et al. 1995. Current Opinion Biotech. 6,59.
Waye et al., Protein Engineering 8:90 (1995).
Auffray et al., Life Sciences 318:263–272 (1995).
Rothe et al., Cell 78:681–692 (1994).
Song et al., The Journal of Biological Chemistry 269:22492–22495 (1994).
Tartaglia et al., Cell 74:845–853 (1993).
Boldin et al., The Journal of Biological Chemistry 270(1):387–391 (1995).
Hsu et al., Cell 81:495–504 (1995).
Boldin et al., FEBS Letters 367:39–44 (1995).
Schall et al., Cell 61:361–370 (1990).
Shimasaki et al., J. Biol. Chem. 266:10646–10653 (1991).
Saragovi et al., Bio/Technology 10:773–778 (1992).
McDowell et al., J. Amer. Chem. Soc. 114:9245–9253 (1992).
Kaufman et al., Nucleic Acids Res. 19:4485–4490 (1991).
Kaufman et al., Methods in Enzymology 185:537–566 (1990).
Gyuris et al., Cell 75:791–803 (1993).
Gietz et al., Nucleic Acids Res. 20:1425 (1992).
Miki et al. 1992 (Cancer Res. 52, 643).
Darnay et al 1994 (J. Biol. Chem. 269,20299).
Schall et al 1990 (Cell 61, 361).
Song et al 1994 (J. Biol. Chem. 269, 22492).
Shimasaki et al, 1991. J. Biol. Chem 266, 10646.
Keifer et al. 1992. J. Biol. Chem 267, 12692.

*Primary Examiner*—Stephen Walsh
*Assistant Examiner*—Mukul Ranjan
*Attorney, Agent, or Firm*—Scott A. Brown; Suzanne A. Sprunger; Thomas J. DesRosier

[57] ABSTRACT

Novel TNF receptor death domain ("TNF-R1-DD") ligand proteins are disclosed. Polynucleotides encoding the TNF-R1-DD ligand protein are also disclosed, along with vectors, host cells, and methods of making the TNF-R1-DD ligand protein. Pharmaceutical compositions containing the TNF-R1-DD ligand protein, methods of treating inflammatory conditions, and methods of inhibiting TNF-R death domain binding are also disclosed. Methods of identifying inhibitors of TNF-R death domain binding and inhibitors identified by such methods are also disclosed.

24 Claims, 8 Drawing Sheets

MADD, A TNF RECEPTOR DEATH DOMAIN LIGAND PROTEIN

This application is a continuation-in-part of application Ser. No. 08/602,228, filed Feb. 15, 1996, which was a continuation-in-part of application Ser. No. 08/533,901, filed Sep. 26, 1995, which was a continuation-in-part of application Ser. No. 08/494,440, filed Jun. 19, 1995, which was a continuation-in-part of application Ser. No. 08/327,514, filed Oct. 19, 1994, now abandoned.

BACKGROUND OF THE INVENTION

The present invention relates to the field of anti-inflammatory substances and other substances which act by inhibiting binding to the intracellular domain of a tumor necrosis factor receptor (hereinafter "TNF-R"), such as, for example, the P55 type (or TNF-R1) TNF receptor. More particularly, the present invention is directed to novel ligands which bind to the TNF-R intracellular domain and to inhibition or modulation of signal transduction by this receptor.

Tumor necrosis factor (herein "TNF") is a cytokine which produces a wide range of cellular activities. TNF causes an inflammatory response, which can be beneficial, such as in mounting an immune response to a pathogen, or when overexpressed can lead to other detrimental effects of inflammation.

The cellular effects of TNF are initiated by the binding of TNF to its receptors (TNF-Rs) on the surface of target cells. The isolation of polynucleotides encoding TNF-Rs and variant forms of such receptors has been described in European patent publication Nos. EP 308,378, EP 393,438, EP 433,900, EP 526,905 and EP 568,925; in PCT patent publication Nos. WO91/03553 and WO93/19777; and by Schall et at., Cell 61:361–370 (1990) (disclosing the P55 type TNF receptor). Processes for purification of TNF-Rs have also been disclosed in U.S. Pat. No. 5,296,592.

Native TNF-Rs are characterized by distinct extracellular, transmembrane and intracellular domains. The primary purpose of the extracellular domain is to present a binding site for TNF on the outside of the cell. When TNF is bound to the binding site, a "signal" is transmitted to the inside of the cell through the transmembrane and intracellular domains, indicating that binding has occurred. Transmission or "transduction" of the signal to the inside of the cell occurs by a change in conformation of the transmembrane and/or intracellular domains of the receptor. This signal is "received" by the binding of proteins and other molecules to the intracellular domain of the receptor, resulting in the effects seen upon TNF stimulation. Two distinct TNF receptors of ~55 kd ("TNF-R1") and ~75 kd ("TNF-R2") have been identified. Numerous studies with anti-TNF receptor antibodies have demonstrated that TNF-R1 is the receptor which signals the majority of the pleiotropic activities of TNF. Recently, the domain required for signaling cytotoxicity and other TNF-mediated responses has been mapped to the ~80 amino acid near the C-terminus of TNF-R1. This domain is therefore termed the "death domain" (hereinafter referred to as "TNF-R death domain" and "TNF-R1-DD") (see, Tartaglia et at., Cell 74:845–853 (1993)).

While TNF binding by TNF-Rs results in beneficial cellular effects, it is often desirable to prevent or deter TNF binding from causing other detrimental cellular effects. Although substantial effort has been expended investigating inhibition of TNF binding to the extracellular domain of TNF-Rs, examination of binding of proteins and other molecules to the intracellular domain of TNF-Rs has received much less attention.

However, ligands which bind to the TNF-R intracellular domain have yet to be identified. It would be desirable to identify and isolate such ligands to examine their effects upon TNF-R signal transduction and their use as therapeutic agents for treatment of TNF-induced conditions. Furthermore, identification of such ligands would provide a means for screening for inhibitors of TNF-R/intracellular ligand binding, which will also be useful as anti-inflammatory agents.

SUMMARY OF THE INVENTION

Applicants have for the first time identified novel TNF-R1-DD ligand proteins and have isolated polynucleotides encoding such ligands. Applicants have also identified a known protein which may also bind to the death domain of TNF-R.

In one embodiment, the present invention provides a composition comprising an isolated polynucleotide encoding a protein having TNF-R1-DD ligand protein activity. In preferred embodiments, the polynucleotide is selected from the group consisting of:

(a) a polynucleotide comprising the nucleotide sequence of SEQ ID NO:1 from nucleotide 2 to nucleotide 1231;

(b) a polynucleotide comprising a fragment of the nucleotide sequence of SEQ ID NO:1;

(c) a polynucleotide encoding an TNF-R1-DD ligand protein comprising the amino acid sequence of SEQ ID NO:2;

(d) a polynucleotide encoding an TNF-R1-DD ligand protein comprising a fragment of the amino acid sequence of SEQ ID NO:2;

(e) a polynucleotide comprising the nucleotide sequence of SEQ ID NO:3 from nucleotide 2 to nucleotide 415;

(f) a polynucleotide comprising a fragment of the nucleotide sequence of SEQ ID NO:3;

(g) a polynucleotide encoding an TNF-R1-DD ligand protein comprising the amino acid sequence of SEQ ID NO:4;

(h) a polynucleotide encoding an TNF-R1-DD ligand protein comprising a fragment of the amino acid sequence of SEQ ID NO:4;

(i) a polynucleotide comprising the nucleotide sequence of SEQ ID NO:9 from nucleotide 2 to nucleotide 931;

(j) a polynucleotide comprising a fragment of the nucleotide sequence of SEQ ID NO:9;

(k) a polynucleotide encoding an TNF-R1-DD ligand protein comprising the amino acid sequence of SEQ ID NO:10;

(l) a polynucleotide encoding an TNF-R1-DD ligand protein comprising a fragment of the amino acid sequence of SEQ ID NO:10;

(m) a polynucleotide comprising the nucleotide sequence of SEQ ID NO:11 from nucleotide 2 to nucleotide 1822;

(n) a polynucleotide comprising a fragment of the nucleotide sequence of SEQ ID NO:11;

(o) a polynucleotide encoding an TNF-R1-DD ligand comprising the amino acid sequence of SEQ ID NO:12;

(p) a polynucleotide encoding an TNF-R1-DD ligand protein comprising a fragment of the amino acid sequence of SEQ ID NO:12;

(q) a polynucleotide comprising the nucleotide sequence of SEQ ID NO:13 from nucleotide 3 to nucleotide 2846;

(r) a polynucleotide comprising a fragment of the nucleotide sequence of SEQ ID NO:13, which encodes a protein having TNF-R1-DD ligand protein activity;

(s) a polynucleotide encoding an TNF-R1-DD ligand protein comprising the amino acid sequence of SEQ ID NO:14;

(t) a polynucleotide encoding an TNF-R1-DD ligand protein comprising a fragment of the amino acid sequence of SEQ ID NO:14 and having TNF-R 1-DD ligand protein activity;

(u) a polynucleotide comprising the nucleotide sequence of SEQ ID NO:15 from nucleotide 326 to nucleotide 5092;

(v) a polynucleotide comprising a fragment of the nucleotide sequence of SEQ ID NO:15;

(w) a polynucleotide encoding an TNF-R1-DD ligand protein comprising the amino acid sequence of SEQ ID NO:16;

(x) a polynucleotide encoding an TNF-R1-DD ligand protein comprising a fragment of the amino acid sequence of SEQ ID NO:16;

(y) a polynucleotide comprising the nucleotide sequence of SEQ ID NO:17 from nucleotide 14 to nucleotide 2404;

(z) a polynucleotide comprising a fragment of the nucleotide sequence of SEQ ID NO:17;

(aa) a polynucleotide encoding an TNF-R1-DD ligand protein comprising the amino acid sequence of SEQ ID NO:18;

(bb) a polynucleotide encoding an TNF-R1-DD ligand protein comprising a fragment of the amino acid sequence of SEQ ID NO:18; and (cc) a polynucleotide capable of hybridizing under stringent conditions to any one of the polynucleotides specified in (a)–(cc).

In certain preferred embodiments, the polynucleotide is operably linked to an expression control sequence. The invention also provides a host cell, including bacterial, yeast, insect and mammalian cells, transformed with such polynucleotide compositions.

Processes are also provided for producing an TNF-R1-DD ligand protein, which comprises:

(a) growing a culture of the host cell transformed with such polynucleotide compositions in a suitable culture medium; and (b) purifying the TNF-R1-DD ligand protein from the culture. The ligand protein produced according to such methods is also provided by the present invention.

Compositions comprising a protein having TNF-R1-DD ligand protein activity are also disclosed. In preferred embodiments the protein comprises an amino acid sequence selected from the group consisting of:

(a) the amino acid sequence of SEQ ID NO:2;

(b) fragments of the amino acid sequence of SEQ ID NO:2;

(c) the amino acid sequence of SEQ ID NO:4;

(d) fragments of the amino acid sequence of SEQ ID NO:4;

(e) the amino acid sequence of SEQ ID NO:6;

(f) fragments of the amino acid sequence of SEQ ID NO:6;

(g) the amino acid sequence of SEQ ID NO:10;

(h) fragments of the amino acid sequence of SEQ ID NO:10;

(i) the amino acid sequence of SEQ ID NO:12;

(j) fragments of the amino acid sequence of SEQ ID NO:12;

(k) the amino acid sequence of SEQ ID NO:14;

(l) fragments of the ammo acid sequence of SEQ ID NO:14;

(m) the amino acid sequence of SEQ ID NO:16;

(n) fragments of the amino acid sequence of SEQ ID NO:16;

(o) the amino acid sequence of SEQ ID NO:18; and (p) fragments of the amino acid sequence of SEQ ID NO:18;

the protein being substantially free from other mammalian proteins. Such compositions may further comprise a pharmaceutically acceptable carrier.

Compositions comprising an antibody which specifically reacts with such TNF-R 1-DD ligand protein are also provided by the present invention.

Methods are also provided for identifying an inhibitor of TNF-R death domain binding which comprise:

(a) combining an TNF-R death domain protein with an TNF-R1-DD ligand protein, said combination forming a first binding mixture;

(b) measuring the amount of binding between the TNF-R death domain protein and the TNF-R1-DD ligand protein in the first binding mixture;

(c) combining a compound with the TNF-R death domain protein and an TNF-R1-DD ligand protein to form a second binding mixture;

(d) measuring the amount of binding in the second binding mixture; and (e) comparing the amount of binding in the first binding mixture with the amount of binding in the second binding mixture;

wherein the compound is capable of inhibiting TNF-R death domain binding when a decrease in the amount of binding of the second binding mixture occurs. In certain preferred embodiments the TNF-R1-DD ligand protein used in such method comprises an amino acid sequence selected from the group consisting of:

(a) the amino acid sequence of SEQ ID NO:2;

(b) fragments of the amino acid sequence of SEQ ID NO:2;

(c) the amino acid sequence of SEQ ID NO:4;

(d) fragments of the amino acid sequence of SEQ ID NO:4;

(e) the amino acid sequence of SEQ ID NO:6;

(f) fragments of the amino acid sequence of SEQ ID NO:6;

(g) the ammo acid sequence of SEQ ID NO:8;

(h) fragments of the amino acid sequence of SEQ ID NO:8

(i) the amino acid sequence of SEQ ID NO:10;

(j) fragments of the amino acid sequence of SEQ ID NO:10;

(k) the amino acid sequence of SEQ ID NO:12;

(l) fragments of the amino acid sequence of SEQ ID NO:12;

(m) the amino acid sequence of SEQ ID NO:14;

(n) fragments of the amino acid sequence of SEQ ID NO:14;

(o) the amino acid sequence of SEQ ID NO:16;

(p) fragments of the amino acid sequence of SEQ ID NO:16;

(q) the amino acid sequence of SEQ ID NO:18;

(r) fragments of the amino acid sequence of SEQ ID NO:18.

Compositions comprising inhibitors identified according to such method are also provided. Such compositions may include pharmaceutically acceptable carriers.

Methods are also provided for preventing or ameliorating an inflammatory condition which comprises administering a therapeutically effective amount of a composition comprising a protein having TNF-R1-DD ligand protein activity and a pharmaceutically acceptable carrier.

Other embodiments provide methods of inhibiting TNF-R death domain binding comprising administering a therapeutically effective amount of a composition comprising a protein having TNF-R1-DD ligand protein activity and a pharmaceutically acceptable carrier.

Methods are also provided for preventing or ameliorating an inflammatory condition which comprises administering to a mammalian subject a therapeutically effective amount of a composition comprising a pharmaceutically acceptable carrier and a protein selected from the group consisting of insulin-like growth factor binding protein-5 ("IGFBP-5"), and fragments thereof having TNF-R1-DD ligand protein activity. Such proteins may also be administered for inhibiting TNF-R death domain binding.

Methods of preventing or ameliorating an inflammatory condition or of inhibiting TNF-R death domain binding are provided, which comprise administering to a mammalian subject a therapeutically effective amount of inhibitors of TNF-R death domain binding, are also provided.

Methods of identifying an inhibitor of TNF-R death domain binding are also provided by the present invention which comprise:

(a) transforming a cell with a first polynucleotide encoding an TNF-R death domain protein, a second polynucleotide encoding an TNF-R1-DD ligand protein, and at least one reporter gene, wherein the expression of the reporter gene is regulated by the binding of the TNF-R1-DD ligand protein encoded by the second polynucleotide to the TNF-R death domain protein encoded by the first polynucleotide;

(b) growing the cell in the presence of and in the absence of a compound; and (c) comparing the degree of expression of the reporter gene in the presence of and in the absence of the compound;

wherein the compound is capable of inhibiting TNF-R death domain binding when a decrease in the degree of expression of the reporter gene occurs. In preferred embodiments, the cell is a yeast cell and the second polynucleotide is selected from the group consisting of:

(a) a polynucleotide comprising the nucleotide sequence of SEQ ID NO:1 from nucleotide 2 to nucleotide 1231;

(b) a polynucleotide comprising a fragment of the nucleotide sequence of SEQ ID NO:1, which encodes a protein having TNF-R1-DD ligand protein activity;

(c) a polynucleotide encoding an TNF-R1-DD ligand protein comprising the amino acid sequence of SEQ ID NO:2;

(d) a polynucleotide encoding an TNF-R1-DD ligand protein comprising a fragment of the amino acid sequence of SEQ ID NO:2 and having TNF-R1-DD ligand protein activity;

(e) a polynucleotide comprising the nucleotide sequence of SEQ ID NO:3 from nucleotide 2 to nucleotide 415;

(f) a polynucleotide comprising a fragment of the nucleotide sequence of SEQ ID NO:3, which encodes a protein having TNF-R1-DD ligand protein activity;

(g) a polynucleotide encoding an TNF-R1-DD ligand protein comprising the amino acid sequence of SEQ ID NO:4;

(h) a polynucleotide encoding an TNF-R1-DD ligand protein comprising a fragment of the amino acid sequence of SEQ ID NO:4 and having TNF-R1-DD ligand protein activity;

(i) a polynucleotide comprising the nucleotide sequence of SEQ ID NO:5 from nucleotide 2 to nucleotide 559;

(j) a polynucleotide comprising a fragment of the nucleotide sequence of SEQ ID NO:5, which encodes a protein having TNF-R1-DD ligand protein activity;

(k) a polynucleotide encoding an TNF-R1-DD ligand protein comprising the amino acid sequence of SEQ ID NO:6;

(l) a polynucleotide encoding an TNF-R1-DD ligand protein comprising a fragment of the amino acid sequence of SEQ ID NO:6 and having TNF-R1-DD ligand protein activity;

(m) a polynucleotide comprising the nucleotide sequence of SEQ ID NO:7 from nucleotide 57 to nucleotide 875;

(n) a polynucleotide comprising a fragment of the nucleotide sequence of SEQ ID NO:7, which encodes a protein having TNF-R1-DD ligand protein activity;

(o) a polynucleotide encoding an TNF-R1-DD ligand protein comprising the amino acid sequence of SEQ ID NO:8;

(p) a polynucleotide encoding an TNF-R1-DD ligand protein comprising a fragment of the amino acid sequence of SEQ ID NO:8 and having TNF-R1-DD ligand protein activity;

(q) a polynucleotide comprising the nucleotide sequence of SEQ ID NO:9 from nucleotide 2 to nucleotide 931;

(r) a polynucleotide comprising a fragment of the nucleotide sequence of SEQ ID NO:9;

(s) a polynucleotide encoding an TNF-R1-DD ligand protein comprising the amino acid sequence of SEQ ID NO:10;

(t) a polynucleotide encoding an TNF-R1-DD ligand protein comprising a fragment of the amino acid sequence of SEQ ID NO:10;

(u) a polynucleotide comprising the nucleotide sequence of SEQ ID NO:11 from nucleotide 2 to nucleotide 1822;

(v) a polynucleotide comprising a fragment of the nucleotide sequence of SEQ ID NO:11;

(w) a polynucleotide encoding an TNF-R1-DD ligand protein comprising the amino acid sequence of SEQ ID NO:12;

(x) a polynucleotide encoding an TNF-R1-DD ligand protein comprising a fragment of the amino acid sequence of SEQ ID NO:12;

(y) a polynucleotide comprising the nucleotide sequence of SEQ ID NO:13 from nucleotide 3 to nucleotide 2846;

(z) a polynucleotide comprising a fragment of the nucleotide sequence of SEQ ID NO:13, which encodes a protein having TNF-R1-DD ligand protein activity;

(aa) a polynucleotide encoding an TNF-R1-DD ligand protein comprising the amino acid sequence of SEQ ID NO:14;

(bb) a polynucleotide encoding an TNF-R1-DD ligand protein comprising a fragment of the amino acid sequence of SEQ ID NO:14 and having TNF-R1-DD ligand protein activity;

(cc) a polynucleotide comprising the nucleotide sequence of SEQ ID NO:15 from nucleotide 326 to nucleotide 5092;

(dd) a polynucleotide comprising a fragment of the nucleotide sequence of SEQ ID NO:15, which encodes a protein having TNF-R1-DD ligand protein activity;

(ee) a polynucleotide encoding an TNF-R1-DD ligand protein comprising the amino acid sequence of SEQ ID NO:16;

(ff) a polynucleotide encoding an TNF-R1-DD ligand protein comprising a fragment of the amino acid sequence of SEQ ID NO:16 and having TNF-R1-DD ligand protein activity;

(gg) a polynucleotide comprising the nucleotide sequence of SEQ ID NO:17 from nucleotide 14 to nucleotide 2404;

(hh) a polynucleotide comprising a fragment of the nucleotide sequence of SEQ ID NO:17, which encodes a protein having TNF-R1-DD ligand protein activity;

(ii) a polynucleotide encoding an TNF-R1-DD ligand protein comprising the amino acid sequence of SEQ ID NO:18;

(jj) a polynucleotide encoding an TNF-R1-DD ligand protein comprising a fragment of the amino acid sequence of SEQ ID NO:18 and having TNF-R1-DD ligand protein activity; and (kk) a polynucleotide capable of hybridizing under stringent conditions to any one of the polynucleotides specified in (a)–(jj), which encodes a protein having TNF-R1-DD ligand protein activity.

DETAILED DESCRIPTION OF THE INVENTION

Figure 1:
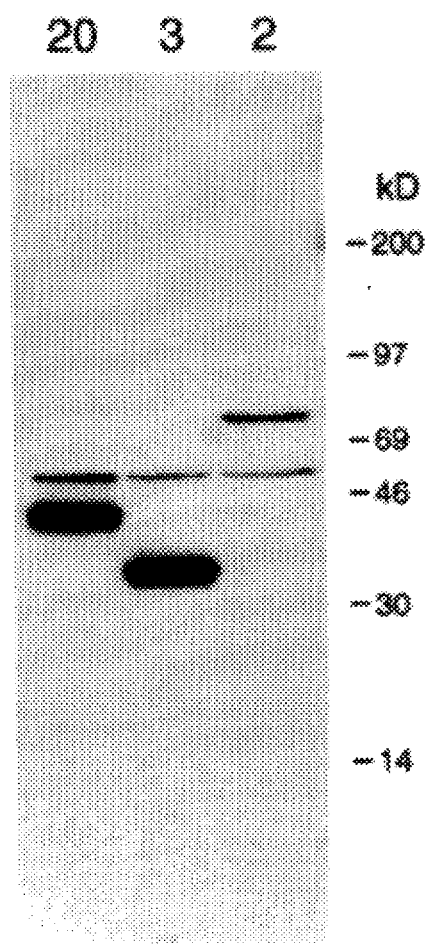
FIGS. 1 and 2 depict autoradiographs demonstrating the expression of TNF-R1-DD ligand proteins of the present invention.

The present inventors have for the first time identified and isolated novel polynucleotides which encode proteins which bind to the TNF-R death domain. As used herein "TNF-R" includes all receptors for tumor necrosis factor. The P55 type TNF-R is the preferred receptor for practicing the present invention.

The sequence of a polynucleotide encoding one such protein is set forth in SEQ ID NO:1 from nucleotides 2 to 1231. This polynucleotide has been identified as "clone 2DD" The amino acid sequence of the TNF-R1-DD ligand protein encoded by clone 2DD is set forth in SEQ ID NO:2. It is believed that clone 2DD is a partial cDNA clone of a longer full length coding sequence. However, as demonstrated herein the protein encoded by clone 2DD does bind the death domain of TNF-R (i.e., has "TNF-R1-DD ligand protein activity" as defined herein). Clone 2DD was deposited with the American Type Culture Collection on Oct. 13, 1994 and given the accession number ATCC 69706.

The protein encoded by clone 2DD is 410 amino acids in length. No identical or closely related sequences were found using BLASTN/BLASTX or FASTA searches. Therefore, clone 2DD encodes a novel protein.

The sequence of a polynucleotide encoding one such protein is set forth in SEQ ID NO:3 from nucleotides 2 to 415. This polynucleotide has been identified as "clone 3DD". The amino acid sequence of the TNF-R1-DD ligand protein encoded by clone 3DD is set forth in SEQ ID NO:4. It is believed that clone 3DD is a partial cDNA clone of a longer full length coding sequence. However, as demonstrated herein the protein encoded by clone 3DD does bind the death domain of TNF-R (i.e., has "TNF-R1-DD ligand protein activity" as defined herein). Clone 3DD was deposited with the American Type Culture Collection on Oct. 13, 1994 and given the accession number ATCC 69705.

The protein encoded by clone 3DD is 138 amino acids. No identical or closely related sequences were found using BLASTN/BLASTX or FASTA searches. Therefore, clone 3DD encodes a novel protein.

A full-length clone corresponding to clone 3DD was also isolated and identified as "clone 3TW". The nucleotide sequence of clone 3TW is reported as SEQ ID NO:13. Nucleotides 3 to 2846 of SEQ ID NO:13 encode a TNF-R1-DD ligand protein, the amino acid sequence of which is reported as SEQ ID NO:14. Amino acids 811 to 948 of SEQ ID NO:14 correspond to amino acids 1 to 138 of SEQ ID NO:4 (clone 3DD). Clone 3TW was deposited with the American Type Culture Collection on Sep. 26, 1995 and given the accession number ATCC 69904.

The sequence of a polynucleotide encoding another such protein is set forth in SEQ ID NO:5 from nucleotides 2 to 559. This polynucleotide has been identified as "clone 20DD." The amino acid sequence of the TNF-R1-DD ligand protein encoded by clone 20DD is set forth in SEQ ID NO:6. It is believed that clone 20DD is a partial cDNA clone of a longer full length coding sequence. However, as demonstrated herein the protein encoded by clone 20DD does bind the death domain of TNF-R (i.e., has "TNF-R1-DD ligand protein activity" as defined herein). Clone 20DD was deposited with the American Type Culture Collection on Oct. 13, 1994 and given the accession number ATCC 69704.

The protein encoded by clone 20DD is identical to amino acids 87 to 272 of insulin-like growth factor binding protein-5 ("IGFBP-5"), a sequence for which was disclosed in J. Biol. Chem. 266:10646–10653 (1991) by Shimasaki et al., which is incorporated herein by reference. The polynucleotide and amino acid sequences of IGFBP-5 are set forth in SEQ ID NO:7 and SEQ ID NO:8, respectively. Based upon the sequence identity between clone 20DD and IGFBP-5, IGFBP-5 and certain fragments thereof will exhibit TNF-R1 -DD ligand binding activity (as defined herein).

The sequence of a polynucleotide encoding another such protein is set forth in SEQ ID NO:9 from nucleotides 2 to 931. This polynucleotide has been identified as "clone 1TU". The amino acid sequence of the TNF-R1-DD ligand protein encoded by clone 1TU is set forth in SEQ ID NO:10. It is believed that clone 1TU is a partial cDNA clone of a longer full length coding sequence. However, as demonstrated herein the protein encoded by clone 1TU does bind the death domain of TNF-R (i.e., has "TNF-R1-DD ligand protein activity" as defined herein). Clone 1TU was deposited with the American Type Culture Collection on Jun. 7, 1995 and given the accession number ATCC 69848.

The protein encoded by clone 1TU is 310 amino acids in length. No identical or closely related sequences were found using BLASTN/BLASTX or FASTA searches. Therefore, clone 1TU encodes a novel protein.

The sequence of a polynucleotide encoding another such protein is set forth in SEQ ID NO:11 from nucleotides 2 to 1822. This polynucleotide has been identified as "clone 27TU". The amino acid sequence of the TNF-R1-DD ligand protein encoded by clone 27TU is set forth in SEQ ID NO:12. It is believed that clone 27TU is a partial cDNA clone of a longer full length coding sequence. However, as demonstrated herein the protein encoded by clone 27TU does bind the death domain of TNF-R (i.e., has "TNF-R1-DD ligand protein activity" as defined herein). Clone 27TU was deposited with the American Type Culture Collection on Jun. 7, 1995 and given the accession number ATCC 69846.

The protein encoded by clone 27TU is 607 amino acids in length. No identical or closely related sequences were found using BLASTN/BLASTX or FASTA searches. Therefore, clone 27TU encodes a novel protein. 27TU may be a longer version of clone 2DD. 2DD encodes the same amino acid sequence (SEQ ID NO:2) as amino acids 198–607 encoded by 27TU (SEQ ID NO:12). The nucleotide sequences of 2DD and 27TU are also identical within this region of identity.

An additional "clone 15TU" was isolated which encoded a portion of the 27TU sequence (approximately amino acids 289–607 of SEQ ID NO:12). Clone 15TU was deposited with the American Type Culture Collection on Jun. 7, 1995 and given the accession number ATCC 69847. 15TU comprises the same nucleotide sequence as 27TU over this region of amino acids.

A full-length clone corresponding to clone 27TU was also isolated and identified as "clone 57TU4A". The nucleotide sequence of clone 57TU4A is reported as SEQ ID NO:15. Nucleotides 336 to 5092 of SEQ ID NO:15 encode a TNF-R1-DD ligand protein, the amino acid sequence of which is reported as SEQ ID NO:16. Amino acids 982 to 1588 of SEQ ID NO:16 correspond to amino acids 1 to 607 of SEQ ID NO:12 (clone 27TU). Clone 57TU4A was deposited with the American Type Culture Collection on Feb. 13, 1996 and given the accession number ATCC 69988.

A full-length clone corresponding to clone 1TU was also isolated and identified as "clone 33-1B". The nucleotide sequence of clone 33-1B is reported as SEQ ID NO:17. Nucleotides 14 to 2404 of SEQ ID NO:17 encode a TNF-R1-DD ligand protein, the amino acid sequence of which is reported as SEQ ID NO:18. Amino acids 488 to 797 of SEQ ID NO:18 correspond to amino acids 1 to 310 of SEQ ID NO:10 (clone 1TU). Clone 33-1B was deposited with the American Type Culture Collection on Aug. 13, 1996 and given the accession number ATCC 98137

Polynucleotides hybridizing to the polynucleotides of the present invention under stringent conditions and highly stringent conditions are also part of the present invention. As used herein, "highly stringent conditions" include, for example, 0.2×SSC at 65° C.; and "stringent conditions" include, for example, 4×SSC at 65° C. or 50% formamide and 4×SSC at 42° C.

For the purposes of the present application, "TNF-R1-DD ligand protein" includes proteins which exhibit TNF-R1-DD ligand protein activity. For the purposes of the present application, a protein is defined as having "TNF-R1-DD ligand protein activity" when it binds to a protein derived from the TNF-R death domain. Activity can be measured by using any assay which will detect binding to an TNF-R death domain protein. Examples of such assays include without limitation the interaction trap assays and assays in which TNF-R death domain protein which is affixed to a surface in a manner conducive to observing binding, including without limitation those described in Examples 1 and 3. As used herein an "TNF-R death domain protein" includes the entire death domain or fragments thereof.

Fragments of the TNF-R1-DD ligand protein which are capable of interacting with the TNF-R death domain or which are capable of inhibiting TNF-R death domain binding (i.e., exhibit TNF-R1-DD ligand protein activity) are also encompassed by the present invention. Fragments of the TNF-R1-DD ligand protein may be in linear form or they may be cyclized using known methods, for example, as described in H. U. Saragovi, et al., Bio/Technology 10, 773–778 (1992) and in R. S. McDowell, et at., J. Amer. Chem. Soc. 114, 9245–9253 (1992), both of which are incorporated herein by reference. Such fragments may be fused to carrier molecules such as immunoglobulins for many purposes, including increasing the valency of TNF-R 1-DD ligand protein binding sites. For example, fragments of the TNF-R1-DD ligand protein may be fused through "linker" sequences to the Fc portion of an immunoglobulin. For a bivalent form of the TNF-R1-DD ligand protein, such a fusion could be to the Fc portion of an IgG molecule. Other immunoglobulin isotypes may also be used to generate such fusions. For example, an TNF-R1-DD ligand protein-IgM fusion would generate a decavalent form of the TNF-R 1-DD ligand protein of the invention.

The isolated polynucleotide of the invention may be operably linked to an expression control sequence such as the pMT2 or pED expression vectors disclosed in Kaufman et al., Nucleic Acids Res. 19, 4485–4490 (1991), in order to produce the TNF-R1-DD ligand protein recombinantly. Many suitable expression control sequences are known in the art. General methods of expressing recombinant proteins are also known and are exemplified in R. Kaufman, Methods in Enzymology 185, 537–566 (1990). As defined herein "operably linked" means that the isolated polynucleotide of the invention and the expression control sequence are situated within a vector or cell in such a way that the TNF-R1-DD ligand protein is expressed by a host cell which has been transformed (transfected) with the ligated polynucleotide/ expression control sequence.

A number of types of cells may act as suitable host cells for expression of the TNF-R1-DD ligand protein. Host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells.

The TNF-R1-DD ligand protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), and such methods are well known in the art, as described in Summers and Smith, *Texas Agricultural Experiment Station Bulletin* No. 1555 (1987), incorporated herein by reference.

Alternatively, it may be possible to produce the TNF-R1-DD ligand protein in lower eukaryotes such as yeast or in prokaryotes such as bacteria. Potentially suitable yeast strains include *Saccharomyces cerevisiae, Schizosaccharomyces pombe*, Kluyveromyces strains, Candida, or any yeast strain capable of expressing heterologous proteins. Potentially suitable bacterial strains include *Escherichia coli, Bacillus subtilis, Salmonella typhimurium*, or any bacterial strain capable of expressing heterologous proteins. If the TNF-R1-DD ligand protein is made in yeast or bacteria, it may be necessary to modify the protein produced therein, for example by phosphorylation or glycosylation of the appropriate sites, in order to obtain the functional TNF-R1-DD ligand protein. Such covalent attachments may be accomplished using known chemical or enzymatic methods.

The TNF-R1-DD ligand protein of the invention may also be expressed as a product of transgenic animals, e.g., as a component of the milk of transgenic cows, goats, pigs, or sheep which are characterized by somatic or germ cells containing a nucleotide sequence encoding the TNF-R1-DD ligand protein.

The TNF-R1-DD ligand protein of the invention may be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the TNF-R 1-DD ligand protein may also include an affinity column containing the TNF-R death domain or other TNF-R death domain protein; one or more column steps over such affinity resins as concanavalin A-agarose, heparin-toyopearl® or Cibacrom blue 3GA Sepharose®; one or more steps involving hydrophobic interaction chromatography using such resins as phenyl ether, butyl ether, or propyl ether; or immunoaffinity chromatography.

Alternatively, the TNF-R1-DD ligand protein of the invention may also be expressed in a form which will facilitate purification. For example, it may be expressed as a fusion protein, such as those of maltose binding protein (MBP) or glutathione-S-transferase (GST). Kits for expression and purification of such fusion proteins are commercially available from New England BioLab (Beverly, Mass.) and Pharmacia (Piscataway, N.J.), respectively. The TNF-R ligand protein can also be tagged with an epitope and subsequently purified by using a specific antibody directed to such epitope. One such epitope ("Flag") is commercially available from Kodak (New Haven, Conn.).

Finally, one or more reverse-phase high performance liquid chromatography (RP-HPLC) steps employing hydrophobic RP-HPLC media, e.g., silica gel having pendant methyl or other aliphatic groups, can be employed to further purify the TNF-R1-DD ligand protein. Some or all of the foregoing purification steps, in various combinations, can also be employed to provide a substantially homogeneous isolated recombinant protein. The TNF-R1-DD ligand protein thus purified is substantially free of other mammalian proteins and is defined in accordance with the present invention as an "isolated TNF-R1-DD ligand protein."

TNF-R1-DD ligand proteins may also be produced by known conventional chemical synthesis. Methods for constructing the proteins of the present invention by synthetic means are known to those skilled in the art. The synthetically-constructed protein sequences, by virtue of sharing primary, secondary or tertiary structural and/or conformational characteristics with TNF-R1-DD ligand proteins may possess biological properties in common therewith, including TNF-R1-DD ligand protein activity. Thus, they may be employed as biologically active or immunological substitutes for natural, purified TNF-R1-DD ligand proteins in screening of therapeutic compounds and in immunological processes for the development of antibodies.

The TNF-R1-DD ligand proteins provided herein also include proteins characterized by amino acid sequences similar to those of purified TNF-R1-DD ligand proteins but into which modification are naturally provided or deliberately engineered. For example, modifications in the peptide or DNA sequences can be made by those skilled in the art using known techniques. Modifications of interest in the TNF-R1-DD ligand protein sequences may include the replacement, insertion or deletion of a selected amino acid residue in the coding sequence. For example, one or more of the cysteine residues may be deleted or replaced with another amino acid to alter the conformation of the molecule. Mutagenic techniques for such replacement, insertion or deletion are well known to those skilled in the art (see, e.g., U.S. Pat. No. 4,518,584).

Other fragments and derivatives of the sequences of TNF-R1-DD ligand proteins which would be expected to retain TNF-R1-DD ligand protein activity in whole or in part and may thus be useful for screening or other immunological methodologies may also be easily made by those skilled in the art given the disclosures herein. Such modifications are believed to be encompassed by the present invention.

TNF-R1-DD ligand protein of the invention may also be used to screen for agents which are capable of inhibiting or blocking binding of an TNF-R1-DD ligand protein to the death domain of TNF-R, and thus may act as inhibitors of TNF-R death domain binding and/or TNF activity. Binding assays using a desired binding protein, immobilized or not, are well known in the art and may be used for this purpose using the TNF-R1-DD ligand protein of the invention. Examples 1 and 3 describe examples of such assays. Appropriate screening assays may be cell-based or cell-free. Alternatively, purified protein based screening assays may be used to identify such agents. For example, TNF-R1-DD ligand protein may be immobilized in purified form on a carrier and binding to purified TNF-R death domain may be measured in the presence and in the absence of potential inhibiting agents. A suitable binding assay may alternatively employ purified TNF-R death domain immobilized on a carrier, with a soluble form of a TNF-R1-DD ligand protein of the invention. Any TNF-R1-DD ligand protein may be used in the screening assays described above.

In such a screening assay, a first binding mixture is formed by combining TNF-R death domain protein and TNF-R1-DD ligand protein, and the amount of binding in the first binding mixture ($B_o$) is measured. A second binding mixture is also formed by combining TNF-R death domain protein, TNF-R1-DD ligand protein, and the compound or agent to be screened, and the amount of binding in the second binding mixture (B) is measured. The amounts of binding in the first and second binding mixtures are compared, for example, by performing a $B/B_o$ calculation. A compound or agent is considered to be capable of inhibiting TNF-R death domain binding if a decrease in binding in the second binding mixture as compared to the first binding mixture is observed. The formulation and optimization of binding mixtures is within the level of skill in the art. Such binding mixtures may also contain buffers and salts necessary to enhance or to optimize binding, and additional control assays may be included in the screening assay of the invention.

Alternatively, appropriate screening assays may be cell based. For example, the binding or interaction between an TNF-R ligand protein and the TNF-R death domain can be measured in yeast as described below in Examples 1 and 3.

Compounds found to reduce, preferably by at least about 10%, more preferably greater than about 50% or more, the binding activity of TNF-R1-DD ligand protein to TNF-R death domain may thus be identified and then secondarily screened in other binding assays, including in vivo assays. By these means compounds having inhibitory activity for TNF-R death domain binding which may be suitable as anti-inflammatory agents may be identified.

Isolated TNF-R1-DD ligand protein may be useful in treating, preventing or ameliorating inflammatory conditions and other conditions, such as cachexia, autoimmune disease, graft versus host reaction, osteoporosis, colitis, myelogenous leukemia, diabetes, wasting, and atherosclerosis. Isolated TNF-R1-DD ligand protein may be used itself as an inhibitor of TNF-R death domain binding or to design inhibitors of TNF-R death domain binding. Inhibitors of binding of TNF-R1-DD ligand protein to the TNF-R death domain ("TNF-R intracellular binding inhibitors") are also useful for treating such conditions.

The present invention encompasses both pharmaceutical compositions and therapeutic methods of treatment or use which employ isolated TNF-R1-DD ligand protein and/or binding inhibitors of TNF-R intracellular binding.

Isolated TNF-R1-DD ligand protein or binding inhibitors (from whatever source derived, including without limitation from recombinant and non-recombinant cell lines) may be used in a pharmaceutical composition when combined with a pharmaceutically acceptable carrier. Such a composition may also contain (in addition to TNF-R1-DD ligand protein or binding inhibitor and a carrier) diluents, fillers, salts, buffers, stabilizers, solubilizers, and other materials Well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors such as M-CSF, GM-CSF, TNF, IL-2, IL-3, IL-4, IL-5, IL-6, IL-7, IL-8, IL-9, G-CSF, Meg-CSF, stem cell factor, and erythropoietin. The pharmaceutical composition may further contain other anti-inflammatory agents. Such additional factors and/or agents may be included in the pharmaceutical composition to produce a synergistic effect with isolated TNF-R1-DD ligand protein or binding inhibitor, or to minimize side effects caused by the isolated TNF-R1-DD ligand protein or binding inhibitor. Conversely, isolated TNF-R1-DD ligand protein or binding inhibitor may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent.

The pharmaceutical composition of the invention may be in the form of a liposome in which isolated TNF-R1-DD ligand protein or binding inhibitor is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

As used herein, the term "therapeutically effective amount" means the total amount of each active component of the pharmaceutical composition or method that is sufficient to show a meaningful patient benefit, i.e., treatment, healing, prevention or amelioration of an inflammatory response or condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of isolated TNF-R1-DD ligand protein or bidding inhibitor is administered to a mammal having a condition to be treated. Isolated TNF-R 1-DD ligand protein or binding inhibitor may be administered in accordance with the method of the invention either alone or in combination with other therapies such as treatments employing cytokines, lymphokines or other hematopoietic factors. When co-administered with one or more cytokines, lymphokines or other hematopoietic factors, isolated TNF-R1-DD ligand protein or binding inhibitor may be administered either simultaneously with the cytokine(s), lymphokine(s), other hematopoietic factor(s), thrombolytic or anti-thrombotic factors, or sequentially. If administered sequentially, the attending physician will decide on the appropriate sequence of administering isolated TNF-R1-DD ligand protein or binding inhibitor in combination with cytokine(s), lymphokine(s), other hematopoietic factor(s), thrombolytic or anti-thrombotic factors.

Administration of isolated TNF-R1-DD ligand protein or binding inhibitor used in the pharmaceutical composition or to practice the method of the present invention can be carried out in a variety of conventional ways, such as oral ingestion, inhalation, or cutaneous, subcutaneous, or intravenous injection. Intravenous administration to the patient is preferred.

When a therapeutically effective amount of isolated TNF-R1-DD ligand protein or binding inhibitor is administered orally, isolated TNF-R1-DD ligand protein or binding inhibitor will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% isolated TNF-R1-DD ligand protein or binding inhibitor, and preferably from about 25 to 90% isolated TNF-R1-DD ligand protein or binding inhibitor. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of isolated TNF-R1-DD ligand protein or binding inhibitor, and preferably from about 1 to 50% isolated TNF-R1-DD ligand protein or binding inhibitor.

When a therapeutically effective amount of isolated TNF-R1-DD ligand protein or binding inhibitor is administered by intravenous, cutaneous or subcutaneous injection, isolated TNF-R1-DD ligand protein or binding inhibitor will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to isolated TNF-R1-DD ligand protein or binding inhibitor, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of isolated TNF-R1-DD ligand protein or binding inhibitor in the pharmaceutical composition of the present invention will depend upon the nature and severity of the condition being treated, and on the nature of prior treatments which the patient has undergone. Ultimately, the attending physician will decide the amount of isolated TNF-R1-DD ligand protein or binding inhibitor with which to treat each individual patient. Initially, the attending physician will administer low doses of isolated TNF-R1-DD ligand protein or binding inhibitor and observe the patient's response. Larger doses of isolated TNF-R1-DD ligand protein or binding inhibitor may be administered until the optimal therapeutic effect is obtained for the patient, and at that point the dosage is not increased further. It is contemplated that the various pharmaceutical compositions used to practice the method of the present invention should contain about 0.1 μg to about 100 mg of isolated TNF-R1-DD ligand protein or binding inhibitor per kg body weight.

The duration of intravenous therapy using the pharmaceutical composition of the present invention will vary, depending on the severity of the disease being treated and the condition and potential idiosyncratic response of each individual patient. It is contemplated that the duration of each application of the isolated TNF-R1-DD ligand protein or binding inhibitor will be in the range of 12 to 24 hours of continuous intravenous administration. Ultimately the attending physician will decide on the appropriate duration of intravenous therapy using the pharmaceutical composition of the present invention.

Isolated TNF-R1-DD ligand protein of the invention may also be used to immunize animals to obtain polyclonal and monoclonal antibodies which specifically react with the TNF-R1-DD ligand protein and which may inhibit TNF-R death domain binding. Such antibodies may be obtained using either the entire TNF-R1-DD ligand protein or fragments of TNF-R1-DD ligand protein as an immunogen. The peptide immunogens additionally may contain a cysteine residue at the carboxyl terminus, and are conjugated to a hapten such as keyhole limpet hemocyanin (KLH). Methods for synthesizing such peptides are known in the art, for example, as in R. P. Merrifield, J. Amer. Chem. Soc. 85, 2149-2154 (1963); J. L. Krstenansky, et al., FEBS Lett. 211, 10 (1987).

Monoclonal antibodies binding to TNF-R1-DD ligand protein or to complex carbohydrate moieties characteristic of the TNF-R1-DD ligand glycoprotein may be useful diagnostic agents for the immunodetection of TNF-R ligand protein.

Neutralizing monoclonal antibodies binding to TNF-R1-DD ligand protein or to complex carbohydrates characteristic of TNF-R1-DD ligand glycoprotein may also be useful therapeutics for both inflammatory conditions and also in the treatment of some forms of cancer where abnormal expression of TNF-R1-DD ligand protein is involved. These neutralizing monoclonal antibodies are capable of blocking the signaling function of the TNF-R1-DD ligand protein. By blocking the binding of TNF-R1-DD ligand protein, certain biological responses to TNF are either abolished or markedly reduced. In the case of cancerous cells or leukemic cells, neutralizing monoclonal antibodies against TNF-R1-DD ligand protein may be useful in detecting and preventing the metastatic spread of the cancerous cells, which may be mediated by the TNF-R1-DD ligand protein.

Due to the similarity of their sequences to the insulin growth factor binding protein ("IGFBP-5") and fragments thereof which bind to the TNF-R death domain are proteins having TNF-R1-DD ligand protein activity as defined herein. As a result, they are also useful in pharmaceutical compositions, for treating inflammatory conditions and for inhibiting TNF-R death domain binding as described above for TNF-R 1-DD ligand proteins generally.

EXAMPLE 1

CLONING OF TNF-R DEATH DOMAIN LIGAND PROTEIN ENCODING POLYNUCLEOTIDE

A yeast genetic selection method, the "interaction trap" [Gyuris et al, Cell 75:791-803, 1993, which is incorporated herein by reference], was used to screen WI38 cell cDNA libraries (preparation, see below) for proteins that interact with the death domain of the P55 type 1 TNF receptor (TNF-R1-DD). A polynucleotide encoding amino acids 326 to 413 of the P55 type TNF receptor, TNF-R1-DD, was obtained via the polymerase chain reaction (PCR) using a grafting method. This TNF-R1-DD DNA was then cloned into pEG202 by BamHI and Sal I sites, generating the bait plasmid, pEG202-TNF-R1-DD. This plasmid contains the HIS3 selectable marker, and expression of the bait, the LexA-TNF-R1-DD fusion protein, is from the strong constitutive ADH1 promoter. To create the reporter strain carrying the bait protein, yeast strain EGY48, containing the reporter sequence LexAop-Leu2 in place of the chromosomal LEU2, was transformed with pEG202-TNF-R1-DD and pSH18-34 (Ura+), which carries another reporter sequence, LexAop-lacZ. For screening cDNAs encoding proteins that interact with TNF-R1-DD, the expression vector pJG4-5 (TRP1), containing the WI38 cell cDNA library (see below for the cDNA library construction), was transformed into the above strain (EGY48/pEG202-TNF-R1-DD/pSH18-34) according to the method described by Gietz et al., Nucleic Acids Res., 20:1425 (1992).

cDNA Library Construction:

WI38 cell cDNA library: Double stranded cDNA was prepared from 3 μg of WI38 mRNA using reagents provided by the Superscript Choice System (Gibco/BRL, Gaithersberg, Md.) with the following substitutions: the first strand synthesis was primed using an oligo dT/XhoI primer/linker, and the dNTP mix was substituted with a mix containing methyl dCTP (Stratagene, LaJolla, Calif.). The cDNA was modified at both ends by addition of an EcoRI/NotI/SalI adapter linker and subsequently digested with XhoI. This produced cDNA molecules possessing an EcoRI/NotI/SalI overhang at the 5' end of the gene and an XhoI overhang at the 3' end. These fragments were then ligated into the yeast expression/fusion vector pJG4-5 (Gyuris et al., Cell, 75, 791–803, 1993), which contains at its amino terminus, the influenza virus HA1 epitope tag, the B42 acidic transcription activation domain, and the SV40 nuclear localization signal, all under the control of the galactose-dependent GAL1 promoter. The resulting plasmids were then electroporated into DH10B cells (Gibco/BRL). A total of $7.1 \times 10^6$ colonies were plated on LB plates containing 100 ug/ml of ampicillin. These E. coli were scraped, pooled, and a large scale plasmid prep was performed using the Wizard Maxi Prep kit (Promega, Madison, Wis.), yielding 3.2 mg of supercoiled plasmid DNA.

WI38 Cell cDNA Screening Results:

$1 \times 10^6$ transformants were obtained on glucose Ura⁻ His⁻ Trp⁻ plates. These transformants were pooled and resuspended in a solution of 65% glycerol, 10 mM Tris-HCl (pH 7.5), 10 mM $MgCl_2$ and stored at $-80°$ C. in 1 mL aliquots. For screening purposes, aliquots of these were diluted 10-fold into Ura⁻His⁻Trp⁻ CM dropout gal/raff medium (containing 2% galactose, 1% raffinose), which induces the expresssion of the library encoded proteins, and incubated at 30° C. for 4 hours. $12 \times 10^6$ colony forming units (CFUs) were then plated on standard 10 cm galactose X-Gal Ura⁻His⁻Trp⁻Leu⁻ plates at a density of $2 \times 10^5$ CFU/plate. After three days at 30° C., about 1,000 colonies were formed ($Leu^+$) and of those, sixty-four colonies were $LacZ^+$. In order to test if the $Leu^+/LacZ^+$ phenotype was due to the library-encoded protein, the galactose dependency of the phenotype was tested. Expression of the library-encoded proteins was turned off by growth on glucose Ura⁻His Trp master plates and then retested for galactose-dependency on glucose Ura⁻His⁻Trp⁻Leu⁻, galactose Ura⁻His⁻Trp⁻Leu⁻, glucose X-Gal Ura⁻His⁻Trp⁻, and galactose X-Gal Ura⁻His⁻Trp⁻ plates. Of these, 32 colonies showed galactose-dependent growth on Leu⁻ plates and galactose-dependent blue color on X-Gal-containing medium ($LacZ^+$ phenotype). Total yeast DNA was prepared from these colonies according to the method described previously (Hoffman and Winston, 1987). In order to analyze the cDNA sequences, PCR reactions were performed using the above yeast DNA as a template and oligo primers specific for the vector pJG4-5, flanking the cDNA insertion point. PCR products were purified (Qiagen PCR purification kit), subjected to restriction digest with the enzyme HaeIII, run on 1.8% agarose gels, and the restriction patterns compared. Similar and identical restriction patterns were grouped and representatives of each group were sequenced and compared to Genbank and other databases to identify any sequence homologies.

One clone of unique sequence ("2DD") and three clones with identical sequence ("3DD") were isolated and showed no significant sequence homologies compared to Genbank and other databases. Additionally, four other clones ("20DD") with identical sequence to a portion of human insulin-like growth factor binding protein-5 (Shunichi Shimasaki et al., J. Biol. Chem. 266:10646–10653 (1991)) were isolated. The clones "2DD," "3DD" and "20DD" were chosen for further analysis. Library vector pJG4-5 containing these clones sequences were rescued from yeast by transforming the total yeast DNAs into the E. coli strain KC8 and selecting for growth on Trp-ampicillin plates. These putative TNFR1 interacting proteins were then tested further for specificity of interaction with the TNF-R1-DD by the reintroduction of JG4-5 clone into EGY48 derivatives containing a panel of different baits, including bicoid, the cytoplasmic domain of the IL-1 receptor, and TNF-R1-DD. The above clones were found to interact only with the TNF-R1-DD. The interaction between these clones and TNF-R1-DD was thus judged to be specific.

U937 cDNA Screening Results:

A U937 cDNA library was also constructed and screened as described above. 1,020 Leu+ colonies were found and of those, 326 colonies were also LacZ+. 62 colonies of these Leu+/LacZ+ colonies showed a galactose-dependent phenotype. One of these clones, 1TU, encodes a novel sequence. Interestingly, two clones, 15TU and 27TU, encode related or identical sequences, except that 27TU contains about 864 additional nucleotides (or about 288 amino acids) at the 5' end. 15/27TU also encode a novel sequence.

EXAMPLE 2

EXPRESSION OF THE TNF-R1-DD ligand PROTEIN cDNAs encoding TNF-R intracellular ligand proteins were released from the pJG4-5 vector with the appropriate restriction enzymes. For example, EcoRI and XhoI or NotI and XhoI were used to release cDNA from clone 2DD and clone 20DD. Where the restriction sites were also present in the internal sequence of the cDNA, PCR was performed to obtain the cDNA. For example, the cDNA fragment encoding "clone 3DD" was obtained through PCR due to the presence of an internal XhoI site. These cDNAs were then cloned into various expression vectors. These included pGEX (Pharmacia) or pMAL (New England Biolabs) for expression as a GST (Glutathione-S-transferase) or MBP (maltose binding protein) fusion protein in E. coli, a pED-based vector for mammalian expression, and pVL or pBlue-BacHis (Invitrogen) for baculovirus/insect expression. For the immunodetection of TNF-R intracellular ligand expression in mammalian cells, an epitope sequence, "Flag," was inserted into the translational start site of the pED vector, generating the pED-Flag vector. cDNAs were then inserted into the pED-Flag vector. Thus, the expression of cDNA from pED-Flag yields a protein with an amino terminal Met, followed by the "Flag" sequence, Asp-Tyr-Lys-Asp-Asp-Asp-Asp-Lys. Standard DEAE-Dextran or lipofectamine methods were used to transfect COS or CHO dukx cells. Immunodetection of Flag-tagged proteins was achieved using the M2 antibody (Kodak). Moreover, an immunoaffinity column using the M2 antibody, followed by elution with the "Flag" peptide, can be used for the rapid purification of the flag-tagged protein. Similarly, affinity purification of GST-, MBP- or His-tagged fusion proteins can be performed using glutathione, amylose, or nickel columns. Detailed purification protocols are provided by the manufacturers. For many fusion proteins, the TNF-R intracellular ligand can be released by the action of thrombin, factor Xa, or enterokinase cleavage. In the case where highly purified material is required, standard purification procedures, such as ion-exchange, hydrophobic, and gel filtration chromatography will be applied in addition to the affinity purification step.

Figure 2:
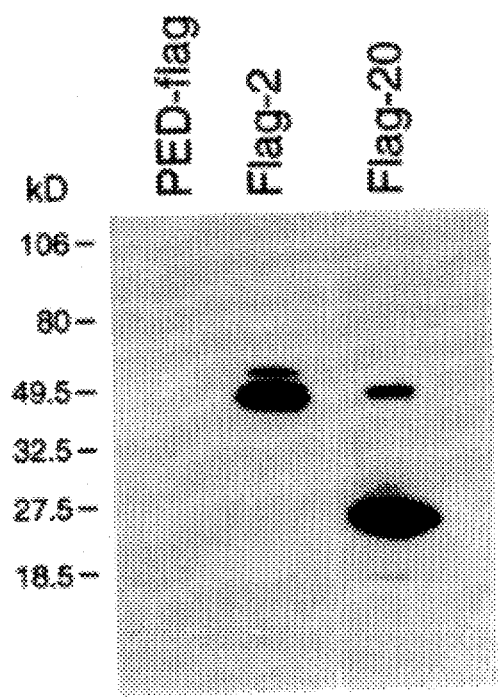

FIGS. 1 and 2 depict autoradiographs demonstrating the expression of TNF-R1-DD ligand proteins in yeast and mammalian cells. FIG. 1 shows the results of expression of isolated clones of the present invention in yeast. EGY48 was transformed with pJG4-5 containing clone 2DD, 3DD or 20DD. Cells were then grown overnight in the galactose/raffinose medium. Cell lysates were prepared and subject to 4–20% SDS gel electrophoresis, followed by Western blot analysis using anti-HA antibody (12CA5, Boehringer Mannheim, Indianapolis, Ind.). FIG. 2 shows the results of expression of Flag-2DD and Flag-20DD in COS cells. COS cells were transfected with either pED-Flag (Vector control), Flag-2DD or Flag-20DD plasmid by the lipofectamine method. Thirty µg of each cell lysate were prepared and subjected to 4–20% SDS gel electrophoresis, followed by Western blot analysis using M2 antibody (Kodak). The bands in the Flag-2DD and Flag-20DD lanes indicate significant expression of the respective TNF-R1-DD ligand proteins.

EXAMPLE 3

ASSAYS OF TNF-R DEATH DOMAIN BINDING

Two different methods were used to assay for TNF-R1-DD ligand protein activity. The first assay measures binding in the yeast strain in "interaction trap," the system used here to screen for TNF-R1-DD interacting proteins. In this system, the expression of reporter genes from both LexAop-Leu2 and LexAop-LacZ relies on the interaction between the bait protein, in this case TNF-R1DD, and the prey, the TNF-R intracellular ligand. Thus, one can measure the strength of the interaction by the level of Leu2 or LacZ expression. The most simple method is to measure the activity of the LacZ encoded protein, β-galactosidase. This activity can be judged by the degree of blueness on the X-Gal containing medium or filter. For the quantitative measurement of β-galactosidase activity, standard assays can be found in "Methods in Yeast Genetics" Cold Spring Harbor, N.Y., 1990 (by Rose, M. D., Winston, F., and Hieter, P.).

The second assay for measuring binding is a cell-free system. An example of a typical assay is described below. Purified GST-TNF-R1-DD fusion protein (2 µg) was mixed with amylose resins bound with a GST-TNF-R1-DD intracellular ligand for 2 hour at 4° C. The mixture was then centrifuged to separate bound (remained with the beads) and unbound (remained in the supernatant) GST-TNF-R1-DD. After extensive washing, the bound GST-TNF-R1-DD was eluted with maltose and detected by Western blot analysis using a GST antibody. The TNF-R1-DD or the intracellular ligand can also be immobilized on other solid supports, such as on plates or fluorobeads. The binding can then be measured using ELISA or SPA (scintillation proximity assay).

EXAMPLE 4

CHARACTERIZATION OF TNF-R DEATH DOMAIN LIGAND PROTEIN

Mapping the interaction site in TNF-R1

Many of the key amino acids for TNF-R signaling have been determined by site-directed mutagenesis (Tataglia et at., Cell 74:845–853 (1993). These amino acids are conserved between TNF-R and the Fas antigen, which is required for mediating cytotoxicity and other cellular responses. In order to test if the TNF-R intracellular proteins interact with these residues, the following mutations were constructed: F345A (substitution of phe at amino acid 345 to Ala), R347A, L351A, F345A/R347A/L351A, E369A, W378A and I408A. The ability of the mutant protein to interact with the intracellular ligand in the "interaction trap" system was tested.

Effect on the TNF-mediated response

The effect of the TNF-R intracellular ligands on the TNF-mediated response can be evaluated in cells overexpressing the ligands. A number of TNF-mediated responses, including transient or prolonged responses, can be measured. For example, TNF-induced kinase activity toward either MBP (myelin basic protein) or the N-terminus (amino acids 1–79) of c-jun can be measured in COS cells or CHO cells either transiently or stably overexpressing clone 2DD, 3DD or clone 20DD. The significance of these ligand proteins in TNF-mediated cytotoxicity and other cellular responses can be measured in L929 or U937 overexpressing cells. Alternatively, other functional assays, such as the induction of gene expression or $PGE_2$ production after prolonged incubation with TNF, can also be used to measure the TNF mediated response. Conversely, the significance of the TNF-R1-DD ligand proteins in TNF signaling can be established by lowering or eliminating the expression of the ligands. These experiments can be performed using antisense expression or transgenic mice.

Enzymatic or functional assays

The signal transduction events initiated by TNF binding to its receptor are still largely unknown. However, one major result of TNF binding is the stimulation of cellular serine/threonine kinase activity. In addition, TNF has been shown to stimulate the activity of PC-PLC, $PLA_2$, and sphingomyelinase. Therefore, some of the TNF-R1-DD ligand proteins may possess intrinsic enzymatic activity that is responsible for these activities. Therefore, enzymatic assays can be performed to test this possibility, particularly with those clones that encode proteins with sequence homology to known enzymes. In addition to enzymatic activity, based on the sequence homology to proteins with known function, other functional assays can also be measured.

EXAMPLE 5

ISOLATION OF FULL LENGTH CLONES

In many cases, cDNAs obtained from the interaction trap method each encode only a portion of the full length protein. For example, based on identity and sequence and the lack of the initiating methionine codon, clones 2DD, 3DD and 20DD apparently do not encode full length proteins. Therefore, it is desirable to isolate full length clones. The cDNAs obtained from the screening, such as clone 2DD, are used as probes, and the cDNA libraries described herein, or alternatively phage cDNA libraries, are screened to obtain full length clones in accordance with known methods (see for example, "Molecular Cloning, A Laboratory Manual", by Sambrook et al., 1989 Cold Spring Harbor).

EXAMPLE 6

ANTIBODIES SPECIFIC FOR TNF-R INTRACELLULAR LIGAND PROTEIN

Antibodies specific for TNF-R intracellular ligand proteins can be produced using purified recombinant protein, as described in Example 2, as antigen. Both polyclonal and monoclonal antibodies will be produced using standard techniques, such as those described in "Antibodies, a Laboratory Manual" by Ed Harlow and David Lane (1988), Cold Spring Harbor Laboratory.

EXAMPLE 7

CHARACTERIZATION OF CLONES 1TU AND 15/27TU

Specificity of Interaction

The specificity of clones 1TU, 15TU and 27TU was tested using a panel of baits. The ability of these clones to bind the TNF-R death domain was compared to their binding to the intracellular domain of the second TNF-R (TNF-R $p75_{IC}$), the entire intracellular domain of TNF-R (TNF-R $p55_{IC}$), the death domain of the fas antigen (which shares 28% identity with TNF-R-DD) ($Fas_{DD}$), the Drosophila transcription factor bicoid, and a region of the IL-1 receptor known to be critical for signalling ($IL-1R_{477-527}$). As shown in Table 1, none of these clones interacted with TNF-R $p75_{IC}$ or $Fas_{DD}$, and only 1TU interacted with bicoid. In contrast, both 1TU and 15TU bound the cytoplasmic domain of the p55 TNF-R, as well as residues 477–527 of the IL-1R. 27TU interacted relatively weakly with these sequences.

TABLE 1

| clone | TNF-$R_{DD}$ | TNF-R $p75_{IC}$ | TNF-R $p55_{IC}$ | $Fas_{DD}$ | bicoid | IL-1R (477-527) |
|---|---|---|---|---|---|---|
| 1TU | +++ | − | +++ | − | ++ | +++ |
| 15TU | +++ | ± | +++ | − | − | ++ |
| 27TU | +++ | − | + | − | − | + |

Interaction with Amino Acids Critical for Signalling

The ability of each clone to interact with four single-site mutations in the TNF-R death domain (each known to abolish signalling) was measured. As shown in Table 2, each of the clones interacted less strongly with the death domain mutants than with the wild type death domain, suggesting that these clones may bind critical residues in vivo.

TABLE 2

| clone | TNF-$R_{DD}$ | F345A | L351A | W378A | I408A |
|---|---|---|---|---|---|
| 1TU | +++ | + | ++ | ++ | + |
| 15TU | +++ | + | + | ++ | ++ |
| 27TU | +++ | + | + | ± | ++ |

Expression of 1TU, 15TU and 27TU

Figure 3A:
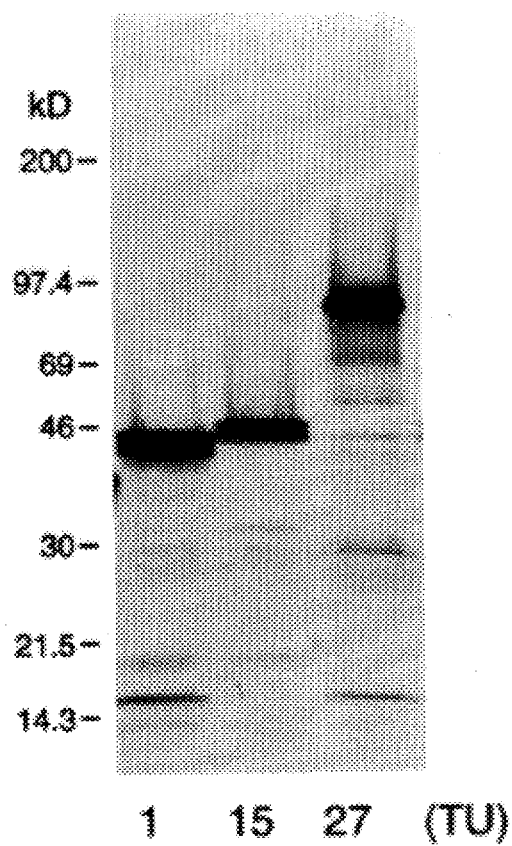
FIGS. 3A and 3B depict autoradiograph demonstrating the expression of clones 1TU, 15TU and 27TU.
Figure 3B:
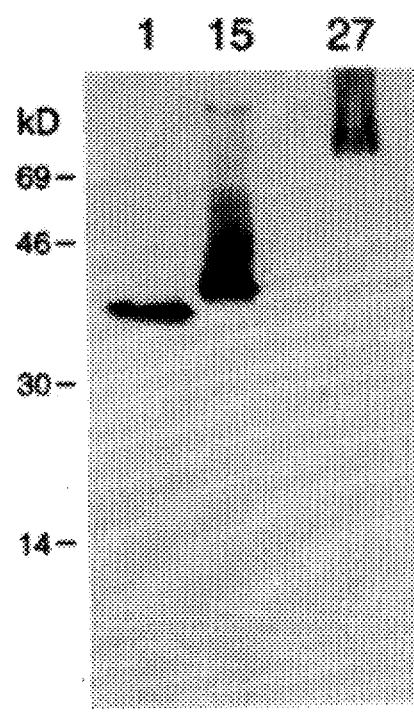

FIG. 3 depicts an autoradiograph demonstrating the expression of clones 1TU, 15TU and 27TU in yeast (A) and COS cells (B).

In (A): EGY48 was transformed with pJG4-5 containing clones 1TU, 15TU or 27TU. Cells were then grown overnight in galactose/raffinose medium. Cell lysates were prepared and subjected to 4–20% SDS gel electrophoresis, followed by Western blot analysis using anti-HA antibody (12CA5, Boehringer Mannheim).

In (B): COS cells were transfected with pED-Flag containing clones 1TU, 15TU and 27TU. Cell lysates were prepared and analyzed by Western blot using anti-Flag antibody (M2, Kodak).

Specific Binding of 1TU and 27TU to TNF-R1-DD

Figure 4:
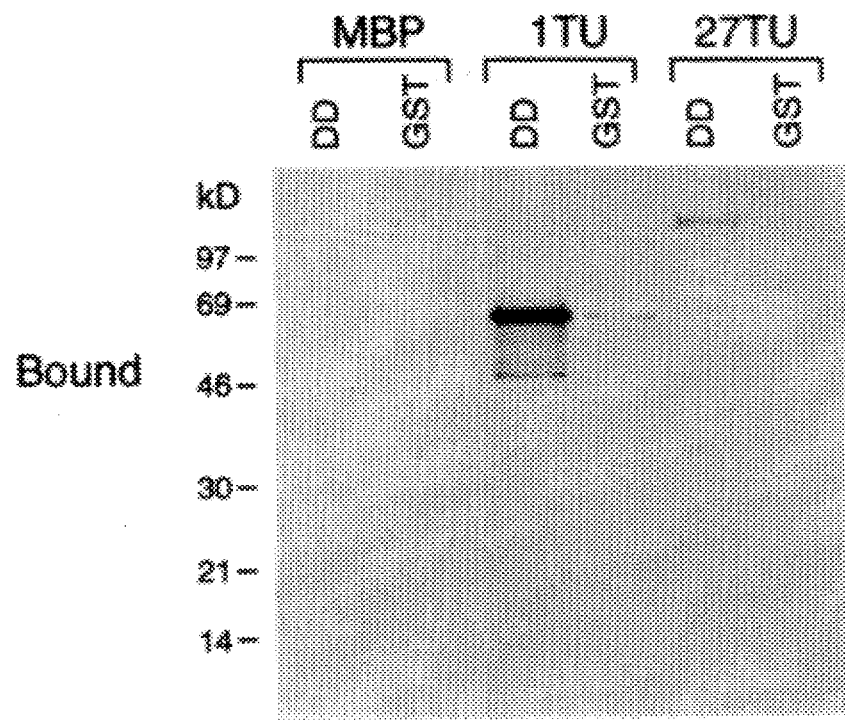
FIG. 4 demonstrates the binding of 1TU and 27TU to TNF-R1-DD. MBP, MBP-1TU or MBP-27TU (3 µg) was incubated with glutathione beads containing 3 µg of either GST or GST-TNF-R1-DD in 100 µl of binding buffer (0.2% Triton, 20 mM Tris pH 7.5, 140 mM NaCl, 0.1 mM EDTA, 10 mM DTT and 5% glycerol). The reaction was performed at 4° C. for 2 hours and centrifuged to remove unbound fraction (Unbound). The beads were then washed with 500 µl binding buffer four times and resuspended into SDS-sample buffer (Bound). These samples were analyzed by Western blot using anti-MBP antibody (New England Biolab).
Figure 4:
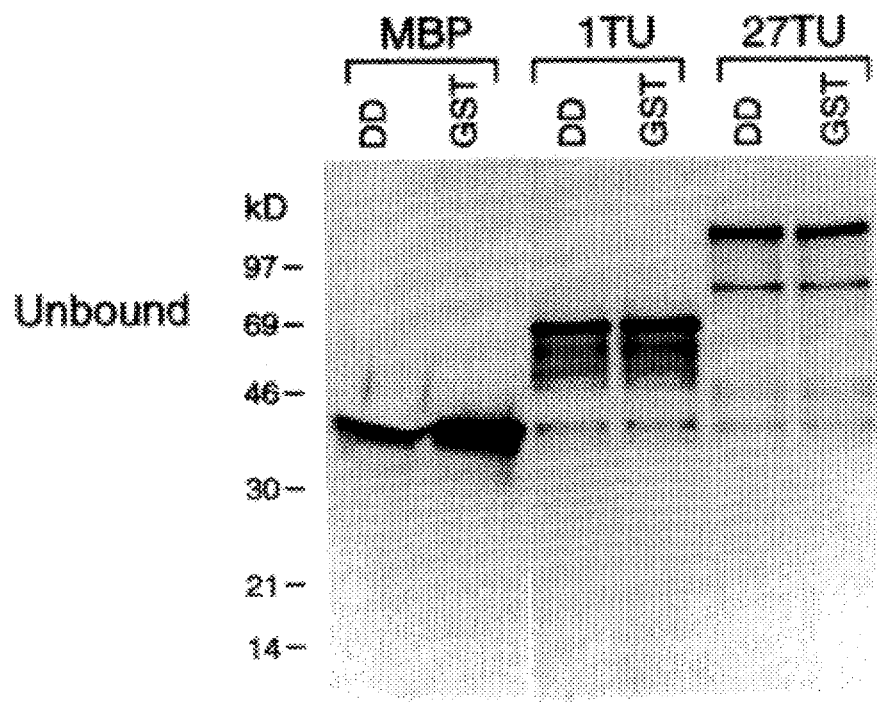

The interaction of 1TU and 27TU with TNF-R1-DD was tested using purified bacterially expressed fusion proteins. As shown in FIG. 4, MBP fusion proteins containing 1TU or 27TU bound only to TNF-R1-DD expressed as a GST fusion protein, but not to GST protein alone. In the control experiment, MBP protein did not bind either GST or GST/TNF-R1-DD. These results indicate that 1TU and 27TU bound specifically to the TNF-R1 death domain in vitro, confirming the data obtained in the interaction trap.

15TU and 27TU Activation JNK Activity

Figure 5:
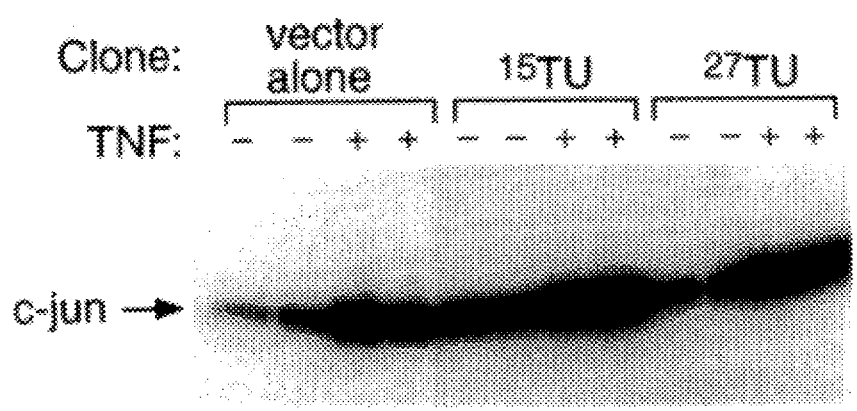
FIG. 5 demonstrates the ability of 15TU and 27TU to activate the JNK pathway. COS cells were contransfected with HA-tagged JNK1 and clones 15tu or 27TU. Cells were left untreated or treated for 15 min with 50 ng/ml TNF, and HA-JNK1 was immunoprecipitated with anti-HA antibody. JNK activity was measured in an in vitro kinase assay using GST-c-jun (amino acids 1–79) as substrate, and reactions were electrophoresed on SDS-PAGE.

The jun N-terminal kinase (JNK) is normally activated within 15 min of TNF treatment in COS cells. 15TU and 27TU were cotransfected with an epitope tagged version of JNK, HA-JNK, in duplicate. After TNF treatment, JNK was immunoprecipitated with anti-HA antibody and JNK activity was measured in immunoprecipitation kinase assays, using GST-c-jun (amino acids 1–79) as substrate). Reactions were electrophoresed on SDS-PAGE. As shown in FIG. 5, transfection of 15TU and 27TU, but not vector alone, into COS cells activated JNK even in the absence of TNF, suggesting that these clones are involved in signal transduction of TNF and the pathway leading to JNK activation in vivo.

EXAMPLE 8

ISOLATION, EXPRESSION AND ASSAY OF CLONE 3TW

Figure 6:
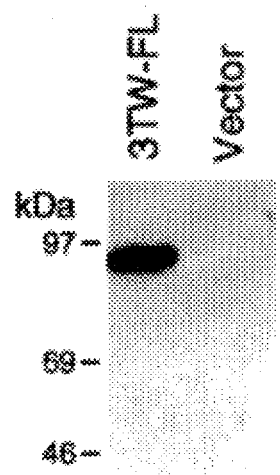
FIG. 6 is an autoradiograph of an SDS-PAGE gel of conditioned media from COS cells transfected with clone 3TW.

Clone 3TW was isolated from the WI38 cDNA library using clone 3DD as a probe. Clone 3TW was expressed. FIG. 6 is an autoradiograph which demonstrates expression of 3TW (indicated by arrow).

Figure 7:
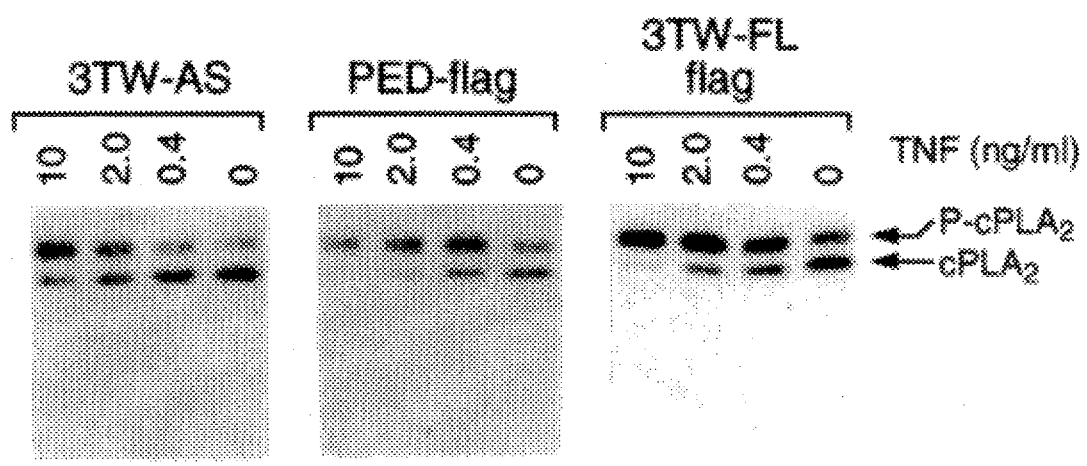
FIG. 7 is an autoradiograph which demonstrates that an antisense oligonucleotide derived from the sequence of clone 3TW inhibits TNF-induced cPLA$_2$ phosphorylation.

An antisense oligonucleotide was derived from the sequence of clone 3TW. The antisense oligonucleotide was assayed to determine its ability to inhibit TNF-induced $cPLA_2$ phosphorylation. FIG. 7 depicts the results of that experiment. Activity of the anitsense oligonucleotide (3TWAS) was compared with the full-length clone (3TWFL), Flag-3TW full length (3TWFLflag) and pED-flag vector (pEDflag). The antisense oligonucleotide inhibited phosphorylation.

SEQUENCE LISTING ( 1 ) GENERAL INFORMATION:

( i i i ) NUMBER OF SEQUENCES: 18

(2) INFORMATION FOR SEQ ID NO:1:

(i) SEQUENCE CHARACTERISTICS:
        (A) LENGTH: 2158 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (ix) FEATURE:
        (A) NAME/KEY: CDS
        (B) LOCATION: 2..1231

(xi) SEQUENCE DESCRIPTION: SEQ ID NO:1:

```
C AGC AAT GCA GGT GAT GGA CCA GGT GGC GAG GGC AGT GTT CAC CTG            46
  Ser Asn Ala Gly Asp Gly Pro Gly Gly Glu Gly Ser Val His Leu
  1               5                  10                  15

GCA AGC TCT CGG GGC ACT TTG TCT GAT AGT GAA ATT GAG ACC AAC TCT          94
Ala Ser Ser Arg Gly Thr Leu Ser Asp Ser Glu Ile Glu Thr Asn Ser
                20                  25                  30

GCC ACA AGC ACC ATC TTT GGT AAA GCC CAC AGC TTG AAG CCA AGC ATA         142
Ala Thr Ser Thr Ile Phe Gly Lys Ala His Ser Leu Lys Pro Ser Ile
            35                  40                  45

AAG GAG AAG CTG GCA GGC AGC CCC ATT CGT ACT TCT GAA GAT GTG AGC         190
Lys Glu Lys Leu Ala Gly Ser Pro Ile Arg Thr Ser Glu Asp Val Ser
        50                  55                  60

CAG CGA GTC TAT CTC TAT GAG GGA CTC CTA GGC AAA GAG CGT TCT ACT         238
Gln Arg Val Tyr Leu Tyr Glu Gly Leu Leu Gly Lys Glu Arg Ser Thr
    65                  70                  75

TTA TGG GAC CAA ATG CAA TTC TGG GAA GAT GCC TTC TTA GAT GCT GTG         286
Leu Trp Asp Gln Met Gln Phe Trp Glu Asp Ala Phe Leu Asp Ala Val
80                  85                  90                  95

ATG TTG GAG AGA GAA GGG ATG GGT ATG GAC CAG GGT CCC CAG GAA ATG         334
Met Leu Glu Arg Glu Gly Met Gly Met Asp Gln Gly Pro Gln Glu Met
                100                 105                 110

ATC GAC AGG TAC CTG TCC CTT GGA GAA CAT GAC CGG AAG CGC CTG GAA         382
Ile Asp Arg Tyr Leu Ser Leu Gly Glu His Asp Arg Lys Arg Leu Glu
            115                 120                 125

GAT GAT GAA GAT CGC TTG CTG GCC ACA CTT CTG CAC AAC CTC ATC TCC         430
Asp Asp Glu Asp Arg Leu Leu Ala Thr Leu Leu His Asn Leu Ile Ser
        130                 135                 140

TAC ATG CTG CTG ATG AAG GTA AAT AAG AAT GAC ATC CGC AAG AAG GTG         478
Tyr Met Leu Leu Met Lys Val Asn Lys Asn Asp Ile Arg Lys Lys Val
    145                 150                 155

AGG CGC CTA ATG GGA AAG TCG CAC ATT GGG CTT GTG TAC AGC CAG CAA         526
Arg Arg Leu Met Gly Lys Ser His Ile Gly Leu Val Tyr Ser Gln Gln
160                 165                 170                 175

ATC AAT GAG GTG CTT GAT CAG CTG GCG AAC CTG AAT GGA CGC GAT CTC         574
Ile Asn Glu Val Leu Asp Gln Leu Ala Asn Leu Asn Gly Arg Asp Leu
                180                 185                 190

TCT ATC TGG TCC AGT GGC AGC CGG CAC ATG AAG AAG CAG ACA TTT GTG         622
Ser Ile Trp Ser Ser Gly Ser Arg His Met Lys Lys Gln Thr Phe Val
            195                 200                 205

GTA CAT GCA GGG ACA GAT ACA AAC GGA GAT ATC TTT TTC ATG GAG GTG         670
Val His Ala Gly Thr Asp Thr Asn Gly Asp Ile Phe Phe Met Glu Val
        210                 215                 220

TGC GAT GAC TGT GTG GTG TTG CGT AGT AAC ATC GGA ACA GTG TAT GAG         718
Cys Asp Asp Cys Val Val Leu Arg Ser Asn Ile Gly Thr Val Tyr Glu
    225                 230                 235

CGC TGG TGG TAC GAG AAG CTC ATC AAC ATG ACC TAC TGT CCC AAG ACG         766
Arg Trp Trp Tyr Glu Lys Leu Ile Asn Met Thr Tyr Cys Pro Lys Thr
```

-continued

| | | | | | | | | | | | | | | | | |
|---|---|---|---|---|---|---|---|---|---|---|---|---|---|---|---|---|
| 240 | | | | | 245 | | | | | 250 | | | | | 255 | |

```
AAG GTG TTG TGC TTG TGG CGT AGA AAT GGC TCT GAG ACC CAG CTC AAC         814
Lys Val Leu Cys Leu Trp Arg Arg Asn Gly Ser Glu Thr Gln Leu Asn
                    260                 265                 270

AAG TTC TAT ACT AAA AAG TGT CGG GAG CTG TAC TAC TGT GTG AAG GAC         862
Lys Phe Tyr Thr Lys Lys Cys Arg Glu Leu Tyr Tyr Cys Val Lys Asp
                275                 280                 285

AGC ATG GAG CGC GCT GCC GCC CGA CAG CAA AGC ATC AAA CCC GGA CCT         910
Ser Met Glu Arg Ala Ala Ala Arg Gln Gln Ser Ile Lys Pro Gly Pro
            290                 295                 300

GAA TTG GGT GGC GAG TTC CCT GTG CAG GAC CTG AAG ACT GGT GAG GGT         958
Glu Leu Gly Gly Glu Phe Pro Val Gln Asp Leu Lys Thr Gly Glu Gly
        305                 310                 315

GGC CTG CTG CAG GTG ACC CTG GAA GGG ATC AAC CTC AAA TTC ATG CAC        1006
Gly Leu Leu Gln Val Thr Leu Glu Gly Ile Asn Leu Lys Phe Met His
320                 325                 330                 335

AAT CAG GTT TTC ATA GAG CTG AAT CAC ATT AAA AAG TGC AAT ACA GTT        1054
Asn Gln Val Phe Ile Glu Leu Asn His Ile Lys Lys Cys Asn Thr Val
                    340                 345                 350

CGA GGC GTC TTT GTC CTG GAG GAA TTT GTT CCT GAA ATT AAA GAA GTG        1102
Arg Gly Val Phe Val Leu Glu Glu Phe Val Pro Glu Ile Lys Glu Val
                355                 360                 365

GTG AGC CAC AAG TAC AAG ACA CCA ATG GCC CAC GAA ATC TGC TAC TCC        1150
Val Ser His Lys Tyr Lys Thr Pro Met Ala His Glu Ile Cys Tyr Ser
            370                 375                 380

GTA TTA TGT CTC TTC TCG TAC GTG GCT GCA GTT CAT AGC AGT GAG GAA        1198
Val Leu Cys Leu Phe Ser Tyr Val Ala Ala Val His Ser Ser Glu Glu
        385                 390                 395

GAT CTC AGA ACC CCG CCC CGG CCT GTC TCT AGC TGATGGAGAG GGGCTACGCA      1251
Asp Leu Arg Thr Pro Pro Arg Pro Val Ser Ser
400                 405                 410

GCTGCCCCAG CCCAGGGCAC GCCCTGGCC CCTTGCTGTT CCCAAGTGCA CGATGCTGCT       1311
GTGACTGAGG AGTGGATGAT GCTCGTGTGT CCTCTGCAAG CCCCCTGCTG TGGCTTGGGT      1371
GGGTACCGGT TATGTGTCCC TCTGAGTGTG TCTTGAGCGT GTCCACCTTC TCCCTCTCCA      1431
CTCCCAGAAG ACCAAACTGC CTTCCCCTCA GGGCTCAAGA ATGTGTACAG TCTGTGGGGC      1491
CGGTGTGAAC CCACTATTTT GTGTCCTTGA GACATTTGTG TTGTGGTTCC TTGTCCTTGT      1551
CCCTGGCGTT AACTGTCCAC TGCAAGAGTC TGGCTCTCCC TTCTCTGTGA CCCGGCATGA      1611
CTGGGCGCCT GGAGCAGTTT CACTCTGTGA GGAGTGAGGG AACCCTGGGG CTCACCCTCT      1671
CAGAGGAAGG GCACAGAGAG GAAGGGAAGA ATTGGGGGGC AGCCGGAGTG AGTGGCAGCC      1731
TCCCTGCTTC CTTCTGCATT CCCAAGCCGG CAGCTACTGC CCAGGGCCCG CAGTGTTGGC      1791
TGCTGCCTGC CACAGCCTCT GTGACTGCAG TGGAGCGGCG AATTCCCTGT GGCCTGCCAC      1851
GCCTTCGGCA TCAGAGGATG GAGTGGTCGA GGCTAGTGGA GTCCAGGGA CCGCTGGCTG       1911
CTCTGCCTGA GCATCAGGGA GGGGGCAGGA AAGACCAAGC TGGGTTTGCA CATCTGTCTG      1971
CAGGCTGTCT CTCCAGGCAC GGGGTGTCAG GAGGGAGAGA CAGCCTGGGT ATGGGCAAGA      2031
AATGACTGTA AATATTTCAG CCCCACATTA TTTATAGAAA ATGTACAGTT GTGTGAATGT      2091
GAAATAAATG TCCTCACCTC CCAAAAAAAA AAAAAAAAAA AAAAAAAAAA AAAAAAAAA       2151
AAAAAAA                                                               2158
```

( 2 ) INFORMATION FOR SEQ ID NO:2:

( i ) SEQUENCE CHARACTERISTICS:
( A ) LENGTH: 410 amino acids
( B ) TYPE: amino acid -continued ( D ) TOPOLOGY: linear ( i i ) MOLECULE TYPE: protein ( x i ) SEQUENCE DESCRIPTION: SEQ ID NO:2:

| Ser | Asn | Ala | Gly | Asp | Gly | Pro | Gly | Gly | Glu | Gly | Ser | Val | His | Leu | Ala |
|-----|-----|-----|-----|-----|-----|-----|-----|-----|-----|-----|-----|-----|-----|-----|-----|
| 1 | | | | 5 | | | | | 10 | | | | | 15 | |
| Ser | Ser | Arg | Gly | Thr | Leu | Ser | Asp | Ser | Glu | Ile | Glu | Thr | Asn | Ser | Ala |
| | | | 20 | | | | 25 | | | | | 30 | | | |
| Thr | Ser | Thr | Ile | Phe | Gly | Lys | Ala | His | Ser | Leu | Lys | Pro | Ser | Ile | Lys |
| | | 35 | | | | | 40 | | | | | 45 | | | |
| Glu | Lys | Leu | Ala | Gly | Ser | Pro | Ile | Arg | Thr | Ser | Glu | Asp | Val | Ser | Gln |
| | 50 | | | | | 55 | | | | | 60 | | | | |
| Arg | Val | Tyr | Leu | Tyr | Glu | Gly | Leu | Leu | Gly | Lys | Glu | Arg | Ser | Thr | Leu |
| 65 | | | | | 70 | | | | | 75 | | | | | 80 |
| Trp | Asp | Gln | Met | Gln | Phe | Trp | Glu | Asp | Ala | Phe | Leu | Asp | Ala | Val | Met |
| | | | | 85 | | | | | 90 | | | | | 95 | |
| Leu | Glu | Arg | Glu | Gly | Met | Gly | Met | Asp | Gln | Gly | Pro | Gln | Glu | Met | Ile |
| | | | 100 | | | | | 105 | | | | | 110 | | |
| Asp | Arg | Tyr | Leu | Ser | Leu | Gly | Glu | His | Asp | Arg | Lys | Arg | Leu | Glu | Asp |
| | | 115 | | | | | 120 | | | | | 125 | | | |
| Asp | Glu | Asp | Arg | Leu | Leu | Ala | Thr | Leu | Leu | His | Asn | Leu | Ile | Ser | Tyr |
| | 130 | | | | | 135 | | | | | 140 | | | | |
| Met | Leu | Leu | Met | Lys | Val | Asn | Lys | Asn | Asp | Ile | Arg | Lys | Lys | Val | Arg |
| 145 | | | | | 150 | | | | | 155 | | | | | 160 |
| Arg | Leu | Met | Gly | Lys | Ser | His | Ile | Gly | Leu | Val | Tyr | Ser | Gln | Gln | Ile |
| | | | | 165 | | | | | 170 | | | | | 175 | |
| Asn | Glu | Val | Leu | Asp | Gln | Leu | Ala | Asn | Leu | Asn | Gly | Arg | Asp | Leu | Ser |
| | | | 180 | | | | | 185 | | | | | 190 | | |
| Ile | Trp | Ser | Ser | Gly | Ser | Arg | His | Met | Lys | Lys | Gln | Thr | Phe | Val | Val |
| | | 195 | | | | | 200 | | | | | 205 | | | |
| His | Ala | Gly | Thr | Asp | Thr | Asn | Gly | Asp | Ile | Phe | Phe | Met | Glu | Val | Cys |
| | 210 | | | | | 215 | | | | | 220 | | | | |
| Asp | Asp | Cys | Val | Val | Leu | Arg | Ser | Asn | Ile | Gly | Thr | Val | Tyr | Glu | Arg |
| 225 | | | | | 230 | | | | | 235 | | | | | 240 |
| Trp | Trp | Tyr | Glu | Lys | Leu | Ile | Asn | Met | Thr | Tyr | Cys | Pro | Lys | Thr | Lys |
| | | | | 245 | | | | | 250 | | | | | 255 | |
| Val | Leu | Cys | Leu | Trp | Arg | Arg | Asn | Gly | Ser | Glu | Thr | Gln | Leu | Asn | Lys |
| | | | 260 | | | | | 265 | | | | | 270 | | |
| Phe | Tyr | Thr | Lys | Lys | Cys | Arg | Glu | Leu | Tyr | Tyr | Cys | Val | Lys | Asp | Ser |
| | | 275 | | | | | 280 | | | | | 285 | | | |
| Met | Glu | Arg | Ala | Ala | Ala | Arg | Gln | Gln | Ser | Ile | Lys | Pro | Gly | Pro | Glu |
| | 290 | | | | | 295 | | | | | 300 | | | | |
| Leu | Gly | Gly | Glu | Phe | Pro | Val | Gln | Asp | Leu | Lys | Thr | Gly | Glu | Gly | Gly |
| 305 | | | | | 310 | | | | | 315 | | | | | 320 |
| Leu | Leu | Gln | Val | Thr | Leu | Glu | Gly | Ile | Asn | Leu | Lys | Phe | Met | His | Asn |
| | | | | 325 | | | | | 330 | | | | | 335 | |
| Gln | Val | Phe | Ile | Glu | Leu | Asn | His | Ile | Lys | Lys | Cys | Asn | Thr | Val | Arg |
| | | | 340 | | | | | 345 | | | | | 350 | | |
| Gly | Val | Phe | Val | Leu | Glu | Glu | Phe | Val | Pro | Glu | Ile | Lys | Glu | Val | Val |
| | | 355 | | | | | 360 | | | | | 365 | | | |
| Ser | His | Lys | Tyr | Lys | Thr | Pro | Met | Ala | His | Glu | Ile | Cys | Tyr | Ser | Val |
| | 370 | | | | | 375 | | | | | 380 | | | | |
| Leu | Cys | Leu | Phe | Ser | Tyr | Val | Ala | Ala | Val | His | Ser | Ser | Glu | Glu | Asp |
| 385 | | | | | 390 | | | | | 395 | | | | | 400 |

```
Leu Arg Thr Pro Pro Arg Pro Val Ser Ser
            405                 410
```

(2) INFORMATION FOR SEQ ID NO:3:

(i) SEQUENCE CHARACTERISTICS:
        (A) LENGTH: 826 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (ix) FEATURE:
        (A) NAME/KEY: CDS
        (B) LOCATION: 2..415

(xi) SEQUENCE DESCRIPTION: SEQ ID NO:3:

```
G GAG GTG CAG GAC CTC TTC GAA GCC CAG GGC AAT GAC CGA CTG AAG      46
  Glu Val Gln Asp Leu Phe Glu Ala Gln Gly Asn Asp Arg Leu Lys
   1               5                  10                  15

CTG CTG GTG CTG TAC AGT GGA GAG GAT GAT GAG CTG CTA CAG CGG GCA    94
Leu Leu Val Leu Tyr Ser Gly Glu Asp Asp Glu Leu Leu Gln Arg Ala
                 20                  25                  30

GCT GCC GGG GGC TTG GCC ATG CTT ACC TCC ATG CGG CCC ACG CTC TGC   142
Ala Ala Gly Gly Leu Ala Met Leu Thr Ser Met Arg Pro Thr Leu Cys
             35                  40                  45

AGC CGC ATT CCC CAA GTG ACC ACA CAC TGG CTG GAG ATC CTG CAG GCC   190
Ser Arg Ile Pro Gln Val Thr Thr His Trp Leu Glu Ile Leu Gln Ala
         50                  55                  60

CTG CTT CTG AGC TCC AAC CAG GAG CTG CAG CAC CGG GGT GCT GTG GTG   238
Leu Leu Leu Ser Ser Asn Gln Glu Leu Gln His Arg Gly Ala Val Val
     65                  70                  75

GTG CTG AAC ATG GTG GAG GCC TCG AGG GAG ATT GCC AGC ACC CTG ATG   286
Val Leu Asn Met Val Glu Ala Ser Arg Glu Ile Ala Ser Thr Leu Met
 80                  85                  90                  95

GAG AGT GAG ATG ATG GAG ATC TTG TCA GTG CTA GCT AAG GGT GAC CAC   334
Glu Ser Glu Met Met Glu Ile Leu Ser Val Leu Ala Lys Gly Asp His
                100                 105                 110

AGC CCT GTC ACA AGG GCT GCT GCA GCC TGC CTG GAC AAA GCA GTG GAA   382
Ser Pro Val Thr Arg Ala Ala Ala Ala Cys Leu Asp Lys Ala Val Glu
            115                 120                 125

TAT GGG CTT ATC CAA CCC AAC CAA GAT GGA GAG TGAGGGGGTT GTCCCTGGGC  435
Tyr Gly Leu Ile Gln Pro Asn Gln Asp Gly Glu
        130                 135

CCAAGGCTCA TGCACACGCT ACCTATTGTG GCACGGAGAG TAAGGACGGA AGCAGCTTTG  495

GCTGGTGGTG GCTGGCATGC CAATACTCT  TGCCCATCCT CGCTTGCTGC CTAGGATGT   555

CCTCTGTTCT GAGTCAGCGG CCACGTTCAG TCACACAGCC CTGCTTGGCC AGCACTGCCT  615

GCAGCCTCAC TCAGAGGGGC CCTTTTCTG TACTACTGTA GTCAGCTGGG AATGGGGAAG   675

GTGCATCCCA ACACAGCCTG TGGATCCTGG GGCATTTGGA AGGGCGCACA CATCAGCAGC  735

CTCACCAGCT GTGAGCCTGC TATCAGGCCT GCCCCTCCAA TAAAAGTGTG TAGAACTCCA  795

AAAAAAAAAA AAAAAAAAAA AAAAAAAAA A                                 826
```

(2) INFORMATION FOR SEQ ID NO:4:

(i) SEQUENCE CHARACTERISTICS:
        (A) LENGTH: 138 amino acids
        (B) TYPE: amino acid
        (D) TOPOLOGY: linear (ii) MOLECULE TYPE: protein (xi) SEQUENCE DESCRIPTION: SEQ ID NO:4:

```
Glu Val Gln Asp Leu Phe Glu Ala Gln Gly Asn Asp Arg Leu Lys Leu
 1               5                  10                  15
Leu Val Leu Tyr Ser Gly Glu Asp Glu Leu Leu Gln Arg Ala Ala
                20                  25                  30
Ala Gly Gly Leu Ala Met Leu Thr Ser Met Arg Pro Thr Leu Cys Ser
         35                  40                  45
Arg Ile Pro Gln Val Thr Thr His Trp Leu Glu Ile Leu Gln Ala Leu
     50                  55                  60
Leu Leu Ser Ser Asn Gln Glu Leu Gln His Arg Gly Ala Val Val
 65                  70                  75                  80
Leu Asn Met Val Glu Ala Ser Arg Glu Ile Ala Ser Thr Leu Met Glu
                 85                  90                  95
Ser Glu Met Met Glu Ile Leu Ser Val Leu Ala Lys Gly Asp His Ser
            100                 105                 110
Pro Val Thr Arg Ala Ala Ala Ala Cys Leu Asp Lys Ala Val Glu Tyr
            115                 120                 125
Gly Leu Ile Gln Pro Asn Gln Asp Gly Glu
        130                 135
```

(2) INFORMATION FOR SEQ ID NO:5:

(i) SEQUENCE CHARACTERISTICS:
    (A) LENGTH: 722 base pairs
    (B) TYPE: nucleic acid
    (C) STRANDEDNESS: double
    (D) TOPOLOGY: linear (ii) MOLECULE TYPE: cDNA (iii) HYPOTHETICAL: NO (ix) FEATURE:
    (A) NAME/KEY: CDS
    (B) LOCATION: 2..559

(xi) SEQUENCE DESCRIPTION: SEQ ID NO:5:

```
G GAG AAG CCG CTG CAC GCC CTG CTG CAC GGC CGC GGG GTT TGC CTC      46
  Glu Lys Pro Leu His Ala Leu Leu His Gly Arg Gly Val Cys Leu
   1               5                  10                  15

AAC GAA AAG AGC TAC CGC GAG CAA GTC AAG ATC GAG AGA GAC TCC CGT     94
Asn Glu Lys Ser Tyr Arg Glu Gln Val Lys Ile Glu Arg Asp Ser Arg
                 20                  25                  30

GAG CAC GAG GAG CCC ACC ACC TCT GAG ATG GCC GAG GAG ACC TAC TCC    142
Glu His Glu Glu Pro Thr Thr Ser Glu Met Ala Glu Glu Thr Tyr Ser
             35                  40                  45

CCC AAG ATC TTC CGG CCC AAA CAC ACC CGC ATC TCC GAG CTG AAG GCT    190
Pro Lys Ile Phe Arg Pro Lys His Thr Arg Ile Ser Glu Leu Lys Ala
         50                  55                  60

GAA GCA GTG AAG AAG GAC CGC AGA AAG AAG CTG ACC CAG TCC AAG TTT    238
Glu Ala Val Lys Lys Asp Arg Arg Lys Lys Leu Thr Gln Ser Lys Phe
     65                  70                  75

GTC GGG GGA GCC GAG AAC ACT GCC CAC CCC CGG ATC ATC TCT GAA CCT    286
Val Gly Gly Ala Glu Asn Thr Ala His Pro Arg Ile Ile Ser Glu Pro
 80                  85                  90                  95

GAG ATG AGA CAG GAG TCT GAG CAG GGC CCC TGC CGC AGA CAC ATG GAG    334
Glu Met Arg Gln Glu Ser Glu Gln Gly Pro Cys Arg Arg His Met Glu
            100                 105                 110

GCT TCC CTG CAG GAG CTC AAA GCC AGC CCA CGC ATG GTG CCC CGT GCT    382
```

```
Ala Ser Leu Gln Glu Leu Lys Ala Ser Pro Arg Met Val Pro Arg Ala
        115                 120                 125

GTG TAC CTG CCC AAT TGT GAC CGC AAA GGA TTC TAC AAG AGA AAG CAG        430
Val Tyr Leu Pro Asn Cys Asp Arg Lys Gly Phe Tyr Lys Arg Lys Gln
        130                 135                 140

TGC AAA CCT TCC CGT GGC CGC AAG CGT GGC ATC TGC TGG TGC GTG GAC        478
Cys Lys Pro Ser Arg Gly Arg Lys Arg Gly Ile Cys Trp Cys Val Asp
    145                 150                 155

AAG TAC GGG ATG AAG CTG CCA GGC ATG GAG TAC GTT GAC GGG GAC TTT        526
Lys Tyr Gly Met Lys Leu Pro Gly Met Glu Tyr Val Asp Gly Asp Phe
160                 165                 170                 175

CAG TGC CAC ACC TTC GAC AGC AGC AAC GTT GAG TGATGCGTCC CCCCCAACC       579
Gln Cys His Thr Phe Asp Ser Ser Asn Val Glu
                180                 185

TTTCCCTCAC CCCCTTCCAC CCCCAGCCCC GACTCCAGCC AGCGCCTCCC TCCACCCCAG      639

GACGCCACTC ATTTCATCTC ATTTAAGGGA AAAATATATA TCTATCTATT TGAGGAAAAA      699

AAAAAAAAAA AAAAAAAAA AAA                                              722
```

( 2 ) INFORMATION FOR SEQ ID NO:6:

( i ) SEQUENCE CHARACTERISTICS:
    ( A ) LENGTH: 186 amino acids
    ( B ) TYPE: amino acid
    ( D ) TOPOLOGY: linear ( i i ) MOLECULE TYPE: protein ( x i ) SEQUENCE DESCRIPTION: SEQ ID NO:6:

```
Glu Lys Pro Leu His Ala Leu Leu His Gly Arg Gly Val Cys Leu Asn
 1           5                  10                  15

Glu Lys Ser Tyr Arg Glu Gln Val Lys Ile Glu Arg Asp Ser Arg Glu
            20                  25                  30

His Glu Glu Pro Thr Thr Ser Glu Met Ala Glu Glu Thr Tyr Ser Pro
        35                  40                  45

Lys Ile Phe Arg Pro Lys His Thr Arg Ile Ser Glu Leu Lys Ala Glu
    50                  55                  60

Ala Val Lys Lys Asp Arg Arg Lys Lys Leu Thr Gln Ser Lys Phe Val
65                  70                  75                  80

Gly Gly Ala Glu Asn Thr Ala His Pro Arg Ile Ile Ser Glu Pro Glu
                85                  90                  95

Met Arg Gln Glu Ser Glu Gln Gly Pro Cys Arg Arg His Met Glu Ala
            100                 105                 110

Ser Leu Gln Glu Leu Lys Ala Ser Pro Arg Met Val Pro Arg Ala Val
        115                 120                 125

Tyr Leu Pro Asn Cys Asp Arg Lys Gly Phe Tyr Lys Arg Lys Gln Cys
    130                 135                 140

Lys Pro Ser Arg Gly Arg Lys Arg Gly Ile Cys Trp Cys Val Asp Lys
145                 150                 155                 160

Tyr Gly Met Lys Leu Pro Gly Met Glu Tyr Val Asp Gly Asp Phe Gln
                165                 170                 175

Cys His Thr Phe Asp Ser Ser Asn Val Glu
            180                 185
```

( 2 ) INFORMATION FOR SEQ ID NO:7:

( i ) SEQUENCE CHARACTERISTICS:
    ( A ) LENGTH: 1023 base pairs
    ( B ) TYPE: nucleic acid
    ( C ) STRANDEDNESS: double -continued (D) TOPOLOGY: linear (ii) MOLECULE TYPE: cDNA (iii) HYPOTHETICAL: NO (ix) FEATURE:
    (A) NAME/KEY: CDS
    (B) LOCATION: 57..875

(xi) SEQUENCE DESCRIPTION: SEQ ID NO:7:

```
CCCTGCACTC TCGCTCTCCT GCCCCACCCC GAGGTAAAGG GGGCGACTAA GAGAAG            56

ATG GTG TTG CTC ACC GCG GTC CTG CTG CTG CTG GCC GCC TAT GCG GGG         104
Met Val Leu Leu Thr Ala Val Leu Leu Leu Leu Ala Ala Tyr Ala Gly
 1               5                  10                  15

CCG GCC CAG AGC CTG GGC TCC TTC GTG CAC TGC GAG CCC TGC GAC GAG         152
Pro Ala Gln Ser Leu Gly Ser Phe Val His Cys Glu Pro Cys Asp Glu
             20                  25                  30

AAA GCC CTC TCC ATG TGC CCC CCC AGC CCC CTG GGC TGC GAG CTG GTC         200
Lys Ala Leu Ser Met Cys Pro Pro Ser Pro Leu Gly Cys Glu Leu Val
         35                  40                  45

AAG GAG CCG GGC TGC GGC TGC TGC ATG ACC TGC GCC CTG GCC GAG GGG         248
Lys Glu Pro Gly Cys Gly Cys Cys Met Thr Cys Ala Leu Ala Glu Gly
     50                  55                  60

CAG TCG TGC GGC GTC TAC ACC GAG CGC TGC GCC CAG GGG CTG CGC TGC         296
Gln Ser Cys Gly Val Tyr Thr Glu Arg Cys Ala Gln Gly Leu Arg Cys
 65                  70                  75                  80

CTC CCC CGG CAG GAC GAG GAG AAG CCG CTG CAC GCC CTG CTG CAC GGC         344
Leu Pro Arg Gln Asp Glu Glu Lys Pro Leu His Ala Leu Leu His Gly
                 85                  90                  95

CGC GGG GTT TGC CTC AAC GAA AAG AGC TAC CGC GAG CAA GTC AAG ATC         392
Arg Gly Val Cys Leu Asn Glu Lys Ser Tyr Arg Glu Gln Val Lys Ile
            100                 105                 110

GAG AGA GAC TCC CGT GAG CAC GAG GAG CCC ACC ACC TCT GAG ATG GCC         440
Glu Arg Asp Ser Arg Glu His Glu Glu Pro Thr Thr Ser Glu Met Ala
        115                 120                 125

GAG GAG ACC TAC TCC CCC AAG ATC TTC CGG CCC AAA CAC ACC CGC ATC         488
Glu Glu Thr Tyr Ser Pro Lys Ile Phe Arg Pro Lys His Thr Arg Ile
    130                 135                 140

TCC GAG CTG AAG GCT GAA GCA GTG AAG AAG GAC CGC AGA AAG AAG CTG         536
Ser Glu Leu Lys Ala Glu Ala Val Lys Lys Asp Arg Arg Lys Lys Leu
145                 150                 155                 160

ACC CAG TCC AAG TTT GTC GGG GGA GCC GAG AAC ACT GCC CAC CCC CGG         584
Thr Gln Ser Lys Phe Val Gly Gly Ala Glu Asn Thr Ala His Pro Arg
                165                 170                 175

ATC ATC TCT GCA CCT GAG ATG AGA CAG GAG TCT GAG CAG GGC CCC TGC         632
Ile Ile Ser Ala Pro Glu Met Arg Gln Glu Ser Glu Gln Gly Pro Cys
            180                 185                 190

CGC AGA CAC ATG GAG GCT TCC CTG CAG GAG CTC AAA GCC AGC CCA CGC         680
Arg Arg His Met Glu Ala Ser Leu Gln Glu Leu Lys Ala Ser Pro Arg
        195                 200                 205

ATG GTG CCC CGT GCT GTG TAC CTG CCC AAT TGT GAC CGC AAA GGA TTC         728
Met Val Pro Arg Ala Val Tyr Leu Pro Asn Cys Asp Arg Lys Gly Phe
    210                 215                 220

TAC AAG AGA AAG CAG TGC AAA CCT TCC CGT GGC CGC AAG CGT GGC ATC         776
Tyr Lys Arg Lys Gln Cys Lys Pro Ser Arg Gly Arg Lys Arg Gly Ile
225                 230                 235                 240

TGC TGG TGC GTG GAC AAG TAC GGG ATG AAG CTG CCA GGC ATG GAG TAC         824
Cys Trp Cys Val Asp Lys Tyr Gly Met Lys Leu Pro Gly Met Glu Tyr
                245                 250                 255

GTT GAC GGG GAC TTT CAG TGC CAC ACC TTC GAC AGC AGC AAC GTT GAG         872
Val Asp Gly Asp Phe Gln Cys His Thr Phe Asp Ser Ser Asn Val Glu
```

|        |        |        | 260    |        |        | 265    |        |        | 270    |        |      |
|--------|--------|--------|--------|--------|--------|--------|--------|--------|--------|--------|------|
TGATGCGTCC CCCCCCAACC TTTCCCTCAC CCCCTCCCAC CCCCAGCCCC GACTCCAGCC 932

AGCGCCTCCC TCCACCCCAG GACGCCACTC ATTTCATCTC ATTTAAGGGA AAAATATATA 992

TCTATCTATT TGAAAAAAAA AAAAAAAACC C 1023

(2) INFORMATION FOR SEQ ID NO:8:

(i) SEQUENCE CHARACTERISTICS:
        (A) LENGTH: 272 amino acids
        (B) TYPE: amino acid
        (D) TOPOLOGY: linear (ii) MOLECULE TYPE: protein (xi) SEQUENCE DESCRIPTION: SEQ ID NO:8:

```
Met Val Leu Leu Thr Ala Val Leu Leu Leu Ala Ala Tyr Ala Gly
  1               5                  10                  15

Pro Ala Gln Ser Leu Gly Ser Phe Val His Cys Glu Pro Cys Asp Glu
                 20                  25                  30

Lys Ala Leu Ser Met Cys Pro Pro Ser Pro Leu Gly Cys Glu Leu Val
             35                  40                  45

Lys Glu Pro Gly Cys Gly Cys Cys Met Thr Cys Ala Leu Ala Glu Gly
     50                  55                  60

Gln Ser Cys Gly Val Tyr Thr Glu Arg Cys Ala Gln Gly Leu Arg Cys
 65                  70                  75                  80

Leu Pro Arg Gln Asp Glu Glu Lys Pro Leu His Ala Leu Leu His Gly
                 85                  90                  95

Arg Gly Val Cys Leu Asn Glu Lys Ser Tyr Arg Glu Gln Val Lys Ile
             100                 105                 110

Glu Arg Asp Ser Arg Glu His Glu Glu Pro Thr Thr Ser Glu Met Ala
     115                 120                 125

Glu Glu Thr Tyr Ser Pro Lys Ile Phe Arg Pro Lys His Thr Arg Ile
130                 135                 140

Ser Glu Leu Lys Ala Glu Ala Val Lys Lys Asp Arg Arg Lys Lys Leu
145                 150                 155                 160

Thr Gln Ser Lys Phe Val Gly Gly Ala Glu Asn Thr Ala His Pro Arg
                 165                 170                 175

Ile Ile Ser Ala Pro Glu Met Arg Gln Glu Ser Glu Gln Gly Pro Cys
             180                 185                 190

Arg Arg His Met Glu Ala Ser Leu Gln Glu Leu Lys Ala Ser Pro Arg
     195                 200                 205

Met Val Pro Arg Ala Val Tyr Leu Pro Asn Cys Asp Arg Lys Gly Phe
210                 215                 220

Tyr Lys Arg Lys Gln Cys Lys Pro Ser Arg Gly Arg Lys Arg Gly Ile
225                 230                 235                 240

Cys Trp Cys Val Asp Lys Tyr Gly Met Lys Leu Pro Gly Met Glu Tyr
                 245                 250                 255

Val Asp Gly Asp Phe Gln Cys His Thr Phe Asp Ser Ser Asn Val Glu
             260                 265                 270
```

(2) INFORMATION FOR SEQ ID NO:9:

(i) SEQUENCE CHARACTERISTICS:
        (A) LENGTH: 1694 base pairs
        (B) TYPE: nucleic acid
        (C) STRANDEDNESS: double
        (D) TOPOLOGY: linear ( i i ) MOLECULE TYPE: cDNA ( i i i ) HYPOTHETICAL: NO ( i x ) FEATURE:
    ( A ) NAME/KEY: CDS
    ( B ) LOCATION: 2..931

( x i ) SEQUENCE DESCRIPTION: SEQ ID NO:9:

```
C TCT CTC AAG GCC AAC ATC CCT GAG GTG GAA GCT GTC CTC AAC ACC            46
  Ser Leu Lys Ala Asn Ile Pro Glu Val Glu Ala Val Leu Asn Thr
   1               5                  10                  15

GAC AGG AGT TTG GTG TGT GAT GGG AAG AGG GGC TTA TTA ACT CGT CTG          94
Asp Arg Ser Leu Val Cys Asp Gly Lys Arg Gly Leu Leu Thr Arg Leu
                20                  25                  30

CTG CAG GTC ATG AAG AAG GAG CCA GCA GAG TCG TCT TTC AGG TTT TGG         142
Leu Gln Val Met Lys Lys Glu Pro Ala Glu Ser Ser Phe Arg Phe Trp
                35                  40                  45

CAA GCT CGG GCT GTG GAG AGT TTC CTC CGA GGG ACC ACC TCC TAT GCA         190
Gln Ala Arg Ala Val Glu Ser Phe Leu Arg Gly Thr Thr Ser Tyr Ala
            50                  55                  60

GAC CAG ATG TTC CTG CTG AAG CGA GGC CTC TTG GAG CAC ATC CTT TAC         238
Asp Gln Met Phe Leu Leu Lys Arg Gly Leu Leu Glu His Ile Leu Tyr
        65                  70                  75

TGC ATT GTG GAC AGC GAG TGT AAG TCA AGG GAT GTG CTC CAG AGT TAC         286
Cys Ile Val Asp Ser Glu Cys Lys Ser Arg Asp Val Leu Gln Ser Tyr
    80                  85                  90                  95

TTT GAC CTC CTG GGG GAG CTG ATG AAG TTC AAC GTT GAT GCA TTC AAG         334
Phe Asp Leu Leu Gly Glu Leu Met Lys Phe Asn Val Asp Ala Phe Lys
                100                 105                 110

AGA TTC AAT AAA TAT ATC AAC ACC GAT GCA AAG TTC CAG GTA TTC CTG         382
Arg Phe Asn Lys Tyr Ile Asn Thr Asp Ala Lys Phe Gln Val Phe Leu
                115                 120                 125

AAG CAG ATC AAC AGC TCC CTG GTG GAC TCC AAC ATG CTG GTG CGC TGT         430
Lys Gln Ile Asn Ser Ser Leu Val Asp Ser Asn Met Leu Val Arg Cys
            130                 135                 140

GTC ACT CTG TCC CTG GAC CGA TTT GAA AAC CAG GTG GAT ATG AAA GTT         478
Val Thr Leu Ser Leu Asp Arg Phe Glu Asn Gln Val Asp Met Lys Val
        145                 150                 155

GCC GAG GTA CTG TCT GAA TGC CGC CTG CTC GCC TAC ATA TCC CAG GTG         526
Ala Glu Val Leu Ser Glu Cys Arg Leu Leu Ala Tyr Ile Ser Gln Val
160                 165                 170                 175

CCC ACG CAG ATG TCC TTC CTC TTC CGC CTC ATC AAC ATC ATC CAC GTG         574
Pro Thr Gln Met Ser Phe Leu Phe Arg Leu Ile Asn Ile Ile His Val
                180                 185                 190

CAG ACG CTG ACC CAG GAG AAC GTC AGC TGC CTC AAC ACC AGC CTG GTG         622
Gln Thr Leu Thr Gln Glu Asn Val Ser Cys Leu Asn Thr Ser Leu Val
            195                 200                 205

ATC CTG ATG CTG GCC CGA CGG AAA GAG CGG CTG CCC CTG TAC CTG CGG         670
Ile Leu Met Leu Ala Arg Arg Lys Glu Arg Leu Pro Leu Tyr Leu Arg
        210                 215                 220

CTG CTG CAG CGG ATG GAG CAC AGC AAG AAG TAC CCC GGC TTC CTG CTC         718
Leu Leu Gln Arg Met Glu His Ser Lys Lys Tyr Pro Gly Phe Leu Leu
    225                 230                 235

AAC AAC TTC CAC AAC CTG CTG CGC TTC TGG CAG CAG CAC TAC CTG CAC         766
Asn Asn Phe His Asn Leu Leu Arg Phe Trp Gln Gln His Tyr Leu His
240                 245                 250                 255

AAG GAC AAG GAC AGC ACC TGC CTA GAG AAC AGC TCC TGC ATC AGC TTC         814
Lys Asp Lys Asp Ser Thr Cys Leu Glu Asn Ser Ser Cys Ile Ser Phe
                260                 265                 270

TCA TAC TGG AAG GAG ACA GTG TCC ATC CTG TTG AAC CCG GAC CGG CAG         862
Ser Tyr Trp Lys Glu Thr Val Ser Ile Leu Leu Asn Pro Asp Arg Gln
```

|     |     |     |     |     |     | 275 |     |     |     |     | 280 |     |     |     |     | 285 |     |     |     |      |
|-----|-----|-----|-----|-----|-----|-----|-----|-----|-----|-----|-----|-----|-----|-----|-----|-----|-----|-----|-----|------|
| TCA | CCC | TCT | GCT | CTC | GTT | AGC | TAC | ATT | GAG | GAG | CCC | TAC | ATG | GAC | ATA |     |     |     |     | 910  |
| Ser | Pro | Ser | Ala | Leu | Val | Ser | Tyr | Ile | Glu | Glu | Pro | Tyr | Met | Asp | Ile |     |     |     |     |      |
|     |     | 290 |     |     |     | 295 |     |     |     | 300 |     |     |     |     |     |     |     |     |     |      |

| GAC | AGG | GAC | TTC | ACT | GAG | GAG | TGACCTTGGG | CCAGGCCTCG | GGAGGCTGCT | 961 |
|-----|-----|-----|-----|-----|-----|-----|------------|------------|------------|-----|
| Asp | Arg | Asp | Phe | Thr | Glu | Glu |            |            |            |     |
|     | 305 |     |     |     | 310 |     |            |            |            |     |

| GGGCCAGTGT | GGGTGAGCGT | GGGTACGATG | CCACACGCCC | TGCCCTGTTC | CCGTTCCTCC | 1021 |
|------------|------------|------------|------------|------------|------------|------|
| CTGCTGCTCT | CTGCCTGCCC | CAGGTCTTTG | GGTACAGGCT | TGGTGGGAGG | GAAGTCCTAG | 1081 |
| AAGCCCTTGG | TCCCCCTGGG | TCTGAGGGCC | CTAGGTCATG | GAGAGCCTCA | GTCCCCATAA | 1141 |
| TGAGGACAGG | GTACCATGCC | CACCTTTCCT | TCAGAACCCT | GGGGCCCAGG | GCCACCCAGA | 1201 |
| GGTAAGAGGA | CATTTAGCAT | TAGCTCTGTG | TGAGCTCCTG | CCGGTTTCTT | GGCTGTCAGT | 1261 |
| CAGTCCCAGA | GTGGGGAGGA | AGATATGGGT | GACCCCACC  | CCCCATCTGT | GAGCCAAGCC | 1321 |
| TCCCTTGTCC | CTGGCCTTTG | GACCCAGGCA | AAGGCTTCTG | AGCCCTGGGC | AGGGGTGGTG | 1381 |
| GGTACCAGAG | AATGCTGCCT | TCCCCAAGC  | CTGCCCCTCT | GCCTCATTTT | CCTGTAGCTC | 1441 |
| CTCTGGTTCT | GTTTGCTCAT | TGGCCGCTGT | GTTCATCCAA | GGGGGTTCTC | CCAGAAGTGA | 1501 |
| GGGGCCTTTC | CCTCCATCCC | TTGGGGCACG | GGGCAGCTGT | GCCTGCCCTG | CCTCTGCCTG | 1561 |
| AGGCAGCCGC | TCCTGCCTGA | GCCTGGACAT | GGGGCCCTTC | CTTGTGTTGC | CAATTTATTA | 1621 |
| ACAGCAAATA | AACCAATTAA | ATGGAGACTA | TTAAATAACT | TTATTTAAA  | AATGAAAAAA | 1681 |
| AAAAAAAAAA | AAA        |            |            |            |            | 1694 |

( 2 ) INFORMATION FOR SEQ ID NO:10:

( i ) SEQUENCE CHARACTERISTICS:
        ( A ) LENGTH: 310 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

| Ser | Leu | Lys | Ala | Asn | Ile | Pro | Glu | Val | Glu | Ala | Val | Leu | Asn | Thr | Asp |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Arg | Ser | Leu | Val | Cys | Asp | Gly | Lys | Arg | Gly | Leu | Leu | Thr | Arg | Leu | Leu |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Gln | Val | Met | Lys | Lys | Glu | Pro | Ala | Glu | Ser | Ser | Phe | Arg | Phe | Trp | Gln |
|-----|-----|-----|-----|-----|-----|-----|-----|-----|-----|-----|-----|-----|-----|-----|-----|
|     |     |     | 35  |     |     |     | 40  |     |     |     |     | 45  |     |     |     |

| Ala | Arg | Ala | Val | Glu | Ser | Phe | Leu | Arg | Gly | Thr | Thr | Ser | Tyr | Ala | Asp |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Gln | Met | Phe | Leu | Leu | Lys | Arg | Gly | Leu | Leu | Glu | His | Ile | Leu | Tyr | Cys |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Ile | Val | Asp | Ser | Glu | Cys | Lys | Ser | Arg | Asp | Val | Leu | Gln | Ser | Tyr | Phe |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Asp | Leu | Leu | Gly | Glu | Leu | Met | Lys | Phe | Asn | Val | Asp | Ala | Phe | Lys | Arg |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Phe | Asn | Lys | Tyr | Ile | Asn | Thr | Asp | Ala | Lys | Phe | Gln | Val | Phe | Leu | Lys |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Gln | Ile | Asn | Ser | Ser | Leu | Val | Asp | Ser | Asn | Met | Leu | Val | Arg | Cys | Val |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Thr | Leu | Ser | Leu | Asp | Arg | Phe | Glu | Asn | Gln | Val | Asp | Met | Lys | Val | Ala |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Glu | Val | Leu | Ser | Glu | Cys | Arg | Leu | Leu | Ala | Tyr | Ile | Ser | Gln | Val | Pro |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

```
Thr Gln Met Ser Phe Leu Phe Arg Leu Ile Asn Ile Ile His Val Gln
            180                 185                 190

Thr Leu Thr Gln Glu Asn Val Ser Cys Leu Asn Thr Ser Leu Val Ile
        195                 200                 205

Leu Met Leu Ala Arg Arg Lys Glu Arg Leu Pro Leu Tyr Leu Arg Leu
    210                 215                 220

Leu Gln Arg Met Glu His Ser Lys Lys Tyr Pro Gly Phe Leu Leu Asn
225                 230                 235                 240

Asn Phe His Asn Leu Leu Arg Phe Trp Gln Gln His Tyr Leu His Lys
                245                 250                 255

Asp Lys Asp Ser Thr Cys Leu Glu Asn Ser Ser Cys Ile Ser Phe Ser
            260                 265                 270

Tyr Trp Lys Glu Thr Val Ser Ile Leu Leu Asn Pro Asp Arg Gln Ser
        275                 280                 285

Pro Ser Ala Leu Val Ser Tyr Ile Glu Glu Pro Tyr Met Asp Ile Asp
    290                 295                 300

Arg Asp Phe Thr Glu Glu
305                 310
```

(2) INFORMATION FOR SEQ ID NO:11:

(i) SEQUENCE CHARACTERISTICS:
        (A) LENGTH: 2735 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (ix) FEATURE:
        (A) NAME/KEY: CDS
        (B) LOCATION: 2..1822

(xi) SEQUENCE DESCRIPTION: SEQ ID NO:11:

```
G GAG ATC AGT CGG AAG GTG TAC AAG GGA ATG TTA GAC CTC CTC AAG       46
  Glu Ile Ser Arg Lys Val Tyr Lys Gly Met Leu Asp Leu Leu Lys
  1               5                   10                  15

TGT ACA GTC CTC AGC TTG GAG CAG TCC TAT GCC CAC GCG GGT CTG GGT     94
Cys Thr Val Leu Ser Leu Glu Gln Ser Tyr Ala His Ala Gly Leu Gly
                20                  25                  30

GGC ATG GCC AGC ATC TTT GGG CTT TTG GAG ATT GCC CAG ACC CAC TAC    142
Gly Met Ala Ser Ile Phe Gly Leu Leu Glu Ile Ala Gln Thr His Tyr
            35                  40                  45

TAT AGT AAA GAA CCA GAC AAG CGG AAG AGA AGT CCA ACA GAA AGT GTA    190
Tyr Ser Lys Glu Pro Asp Lys Arg Lys Arg Ser Pro Thr Glu Ser Val
        50                  55                  60

AAT ACC CCA GTT GGC AAG GAT CCT GGC CTA GCT GGG CGG GGG GAC CCA    238
Asn Thr Pro Val Gly Lys Asp Pro Gly Leu Ala Gly Arg Gly Asp Pro
    65                  70                  75

AAG GCT ATG GCA CAA CTG AGA GTT CCA CAA CTG GGA CCT CGG GCA CCA    286
Lys Ala Met Ala Gln Leu Arg Val Pro Gln Leu Gly Pro Arg Ala Pro
80                  85                  90                  95

AGT GCC ACA GGA AAG GGT CCT AAG GAA CTG GAC ACC AGA AGT TTA AAG    334
Ser Ala Thr Gly Lys Gly Pro Lys Glu Leu Asp Thr Arg Ser Leu Lys
                100                 105                 110

GAA GAA AAT TTT ATA GCA TCT ATT GGG CCT GAA GTA ATC AAA CCT GTC    382
Glu Glu Asn Phe Ile Ala Ser Ile Gly Pro Glu Val Ile Lys Pro Val
            115                 120                 125

TTT GAC CTT GGT GAG ACA GAG GAG AAA AAG TCC CAG ATC AGC GCA GAC    430
```

```
            Phe Asp Leu Gly Glu Thr Glu Glu Lys Lys Ser Gln Ile Ser Ala Asp
                    130             135                 140

AGT GGT GTG AGC CTG ACG TCT AGT TCC CAG AGG ACT GAT CAA GAC TCT                478
Ser Gly Val Ser Leu Thr Ser Ser Ser Gln Arg Thr Asp Gln Asp Ser
    145                 150                 155

GTC ATC GGC GTG AGT CCA GCT GTT ATG ATC CGC AGC TCA AGT CAG GAT                526
Val Ile Gly Val Ser Pro Ala Val Met Ile Arg Ser Ser Ser Gln Asp
160                 165                 170                 175

TCT GAA GTT AGC ACC GTG GTG AGT AAT AGC TCT GGA GAG ACC CTT GGA                574
Ser Glu Val Ser Thr Val Val Ser Asn Ser Ser Gly Glu Thr Leu Gly
                180                 185                 190

GCT GAC AGT GAC TTG AGC AGC AAT GCA GGT GAT GGA CCA GGT GGC GAG                622
Ala Asp Ser Asp Leu Ser Ser Asn Ala Gly Asp Gly Pro Gly Gly Glu
            195                 200                 205

GGC AGT GTT CAC CTG GCA AGC TCT CGG GGC ACT TTG TCT GAT AGT GAA                670
Gly Ser Val His Leu Ala Ser Ser Arg Gly Thr Leu Ser Asp Ser Glu
        210                 215                 220

ATT GAG ACC AAC TCT GCC ACA AGC ACC ATC TTT GGT AAA GCC CAC AGC                718
Ile Glu Thr Asn Ser Ala Thr Ser Thr Ile Phe Gly Lys Ala His Ser
    225                 230                 235

TTG AAG CCA AGC ATA AAG GAG AAG CTG GCA GGC AGC CCC ATT CGT ACT                766
Leu Lys Pro Ser Ile Lys Glu Lys Leu Ala Gly Ser Pro Ile Arg Thr
240                 245                 250                 255

TCT GAA GAT GTG AGC CAG CGA GTC TAT CTC TAT GAG GGA CTC CTA GGC                814
Ser Glu Asp Val Ser Gln Arg Val Tyr Leu Tyr Glu Gly Leu Leu Gly
                260                 265                 270

AAA GAG CGT TCT ACT TTA TGG GAC CAA ATG CAA TTC TGG GAA GAT GCC                862
Lys Glu Arg Ser Thr Leu Trp Asp Gln Met Gln Phe Trp Glu Asp Ala
            275                 280                 285

TTC TTA GAT GCT GTG ATG TTG GAG AGA GAA GGG ATG GGT ATG GAC CAG                910
Phe Leu Asp Ala Val Met Leu Glu Arg Glu Gly Met Gly Met Asp Gln
        290                 295                 300

GGT CCC CAG GAA ATG ATC GAC AGG TAC CTG TCC CTT GGA GAA CAT GAC                958
Gly Pro Gln Glu Met Ile Asp Arg Tyr Leu Ser Leu Gly Glu His Asp
    305                 310                 315

CGG AAG CGC CTG GAA GAT GAT GAA GAT CGC TTG CTG GCC ACA CTT CTG               1006
Arg Lys Arg Leu Glu Asp Asp Glu Asp Arg Leu Leu Ala Thr Leu Leu
320                 325                 330                 335

CAC AAC CTC ATC TCC TAC ATG CTG CTG ATG AAG GTA AAT AAG AAT GAC               1054
His Asn Leu Ile Ser Tyr Met Leu Leu Met Lys Val Asn Lys Asn Asp
                340                 345                 350

ATC CGC AAG AAG GTG AGG CGC CTA ATG GGA AAG TCG CAC ATT GGG CTT               1102
Ile Arg Lys Lys Val Arg Arg Leu Met Gly Lys Ser His Ile Gly Leu
            355                 360                 365

GTG TAC AGC CAG CAA ATC AAT GAG GTG CTT GAT CAG CTG GCG AAC CTG               1150
Val Tyr Ser Gln Gln Ile Asn Glu Val Leu Asp Gln Leu Ala Asn Leu
        370                 375                 380

AAT GGA CGC GAT CTC TCT ATC TGG TCC AGT GGC AGC CGG CAC ATG AAG               1198
Asn Gly Arg Asp Leu Ser Ile Trp Ser Ser Gly Ser Arg His Met Lys
    385                 390                 395

AAG CAG ACA TTT GTG GTA CAT GCA GGG ACA GAT ACA AAC GGA GAT ATC               1246
Lys Gln Thr Phe Val Val His Ala Gly Thr Asp Thr Asn Gly Asp Ile
400                 405                 410                 415

TTT TTC ATG GAG GTG TGC GAT GAC TGT GTG GTG TTG CGT AGT AAC ATC               1294
Phe Phe Met Glu Val Cys Asp Asp Cys Val Val Leu Arg Ser Asn Ile
                420                 425                 430

GGA ACA GTG TAT GAG CGC TGG TGG TAC GAG AAG CTC ATC AAC ATG ACC               1342
Gly Thr Val Tyr Glu Arg Trp Trp Tyr Glu Lys Leu Ile Asn Met Thr
            435                 440                 445

TAC TGT CCC AAG ACG AAG GTG TTG TGC TTG TGG CGT AGA AAT GGC TCT               1390
```

| | | | | | | | | | | | | | | | | |
|---|---|---|---|---|---|---|---|---|---|---|---|---|---|---|---|---|
| Tyr | Cys | Pro | Lys | Thr | Lys | Val | Leu | Cys | Leu | Trp | Arg | Arg | Asn | Gly | Ser | |
| | | 450 | | | | 455 | | | | | | 460 | | | | |

| GAG | ACC | CAG | CTC | AAC | AAG | TTC | TAT | ACT | AAA | AAG | TGT | CGG | GAG | CTG | TAC | 1438 |
|---|---|---|---|---|---|---|---|---|---|---|---|---|---|---|---|---|
| Glu | Thr | Gln | Leu | Asn | Lys | Phe | Tyr | Thr | Lys | Lys | Cys | Arg | Glu | Leu | Tyr | |
| | 465 | | | | | 470 | | | | | 475 | | | | | |

| TAC | TGT | GTG | AAG | GAC | AGC | ATG | GAG | CGC | GCT | GCC | GCC | CGA | CAG | CAA | AGC | 1486 |
|---|---|---|---|---|---|---|---|---|---|---|---|---|---|---|---|---|
| Tyr | Cys | Val | Lys | Asp | Ser | Met | Glu | Arg | Ala | Ala | Ala | Arg | Gln | Gln | Ser | |
| 480 | | | | | 485 | | | | | 490 | | | | | 495 | |

| ATC | AAA | CCC | GGA | CCT | GAA | TTG | GGT | GGC | GAG | TTC | CCT | GTG | CAG | GAC | CTG | 1534 |
|---|---|---|---|---|---|---|---|---|---|---|---|---|---|---|---|---|
| Ile | Lys | Pro | Gly | Pro | Glu | Leu | Gly | Gly | Glu | Phe | Pro | Val | Gln | Asp | Leu | |
| | | | | 500 | | | | | 505 | | | | | 510 | | |

| AAG | ACT | GGT | GAG | GGT | GGC | CTG | CTG | CAG | GTG | ACC | CTG | GAA | GGG | ATC | AAC | 1582 |
|---|---|---|---|---|---|---|---|---|---|---|---|---|---|---|---|---|
| Lys | Thr | Gly | Glu | Gly | Gly | Leu | Leu | Gln | Val | Thr | Leu | Glu | Gly | Ile | Asn | |
| | | | 515 | | | | | 520 | | | | | 525 | | | |

| CTC | AAA | TTC | ATG | CAC | AAT | CAG | GTT | TTC | ATA | GAG | CTG | AAT | CAC | ATT | AAA | 1630 |
|---|---|---|---|---|---|---|---|---|---|---|---|---|---|---|---|---|
| Leu | Lys | Phe | Met | His | Asn | Gln | Val | Phe | Ile | Glu | Leu | Asn | His | Ile | Lys | |
| | | 530 | | | | | 535 | | | | | 540 | | | | |

| AAG | TGC | AAT | ACA | GTT | CGA | GGC | GTC | TTT | GTC | CTG | GAG | GAA | TTT | GTT | CCT | 1678 |
|---|---|---|---|---|---|---|---|---|---|---|---|---|---|---|---|---|
| Lys | Cys | Asn | Thr | Val | Arg | Gly | Val | Phe | Val | Leu | Glu | Glu | Phe | Val | Pro | |
| 545 | | | | | 550 | | | | | 555 | | | | | | |

| GAA | ATT | AAA | GAA | GTG | GTG | AGC | CAC | AAG | TAC | AAG | ACA | CCA | ATG | GCC | CAC | 1726 |
|---|---|---|---|---|---|---|---|---|---|---|---|---|---|---|---|---|
| Glu | Ile | Lys | Glu | Val | Val | Ser | His | Lys | Tyr | Lys | Thr | Pro | Met | Ala | His | |
| 560 | | | | | 565 | | | | | 570 | | | | | 575 | |

| GAA | ATC | TGC | TAC | TCC | GTA | TTA | TGT | CTC | TTC | TCG | TAC | GTG | GCT | GCA | GTT | 1774 |
|---|---|---|---|---|---|---|---|---|---|---|---|---|---|---|---|---|
| Glu | Ile | Cys | Tyr | Ser | Val | Leu | Cys | Leu | Phe | Ser | Tyr | Val | Ala | Ala | Val | |
| | | | | 580 | | | | | 585 | | | | | 590 | | |

| CAT | AGC | AGT | GAG | GAA | GAT | CTC | AGA | ACC | CCG | CCC | CGG | CCT | GTC | TCT | AGC | 1822 |
|---|---|---|---|---|---|---|---|---|---|---|---|---|---|---|---|---|
| His | Ser | Ser | Glu | Glu | Asp | Leu | Arg | Thr | Pro | Pro | Arg | Pro | Val | Ser | Ser | |
| | | | 595 | | | | | 600 | | | | | 605 | | | |

| | | | | | |
|---|---|---|---|---|---|
| TGATGGAGAG | GGGCTACGCA | GCTGCCCCAG | CCCAGGGCAC | GCCCTGGCC | CCTTGCTGTT | 1882 |
| CCCAAGTGCA | CGATGCTGCT | GTGACTGAGG | AGTGGATGAT | GCTCGTGTGT | CCTCTGCAAG | 1942 |
| CCCCCTGCTG | TGGCTTGGTT | GGTTACCGGT | TATGTGTCCC | TCTGAGTGTG | TCTTGAGCGT | 2002 |
| GTCCACCTTC | TCCCTCTCCA | CTCCCAGAAG | ACCAAACTGC | CTTCCCCTCA | GGGCTCAAGA | 2062 |
| ATGTGTACAG | TCTGTGGGGC | CGGTGTGAAC | CCACTATTTT | GTGTCCTTGA | GACATTTGTG | 2122 |
| TTGTGGTTCC | TTGTCCTTGT | CCCTGGCGTT | ATAACTGTCC | ACTGCAAGAG | TCTGGCTCTC | 2182 |
| CCTTCTCTGT | GACCCGGCAT | GACTGGGCGC | CTGGAGCAGT | TCACTCTGT | GAGGAGTGAG | 2242 |
| GGAACCCTGG | GGCTCACCCT | CTCAGAGGAA | GGGCACAGAG | AGGAAGGGAA | GAATTGGGGG | 2302 |
| GCAGCCGGAG | TGAGTGGCAG | CCTCCCTGCT | TCCTTCTGCA | TTCCCAAGCC | GGCAGCTACT | 2362 |
| GCCCAGGGCC | CGCAGTGTTG | GCTGCTGCCT | GCCACAGCCT | CTGTGACTGC | AGTGGAGCGG | 2422 |
| CGAATTCCCT | GTGGCCTGCC | ACGCCTTCGG | CATCAGAGGA | TGGAGTGGTC | GAGGCTAGTG | 2482 |
| GAGTCCCAGG | GACCGCTGGC | TGCTCTGCCT | GAGCATCAGG | GAGGGGGCAG | GAAAGACCAA | 2542 |
| GCTGGGTTTG | CACATCTGTC | TGCAGGCTGT | CTCTCCAGGC | ACGGGGTGTC | AGGAGGGAGA | 2602 |
| GACAGCCTGG | GTATGGGCAA | GAAATGACTG | TAAATATTTC | AGCCCCACAT | TATTTATAGA | 2662 |
| AAATGTACAG | TTGTGTGAAT | GTGAAATAAA | TGTCCTCAAC | TCCCAAAAAA | AAAAAAAAAA | 2722 |
| AAAAAAAAAA | AAA | | | | | 2735 |

( 2 ) INFORMATION FOR SEQ ID NO:12:

( i ) SEQUENCE CHARACTERISTICS:
    ( A ) LENGTH: 607 amino acids
    ( B ) TYPE: amino acid
    ( D ) TOPOLOGY: linear ( i i ) MOLECULE TYPE: protein ( x i ) SEQUENCE DESCRIPTION: SEQ ID NO:12:

```
Glu Ile Ser Arg Lys Val Tyr Lys Gly Met Leu Asp Leu Leu Lys Cys
 1               5                  10                  15

Thr Val Leu Ser Leu Glu Gln Ser Tyr Ala His Ala Gly Leu Gly Gly
                20                  25                  30

Met Ala Ser Ile Phe Gly Leu Leu Glu Ile Ala Gln Thr His Tyr Tyr
            35                  40                  45

Ser Lys Glu Pro Asp Lys Arg Lys Arg Ser Pro Thr Glu Ser Val Asn
        50                  55                  60

Thr Pro Val Gly Lys Asp Pro Gly Leu Ala Gly Arg Gly Asp Pro Lys
 65                  70                  75                  80

Ala Met Ala Gln Leu Arg Val Pro Gln Leu Gly Pro Arg Ala Pro Ser
                85                  90                  95

Ala Thr Gly Lys Gly Pro Lys Glu Leu Asp Thr Arg Ser Leu Lys Glu
            100                 105                 110

Glu Asn Phe Ile Ala Ser Ile Gly Pro Glu Val Ile Lys Pro Val Phe
        115                 120                 125

Asp Leu Gly Glu Thr Glu Glu Lys Lys Ser Gln Ile Ser Ala Asp Ser
    130                 135                 140

Gly Val Ser Leu Thr Ser Ser Ser Gln Arg Thr Asp Gln Asp Ser Val
145                 150                 155                 160

Ile Gly Val Ser Pro Ala Val Met Ile Arg Ser Ser Ser Gln Asp Ser
                165                 170                 175

Glu Val Ser Thr Val Val Ser Asn Ser Ser Gly Glu Thr Leu Gly Ala
            180                 185                 190

Asp Ser Asp Leu Ser Ser Asn Ala Gly Asp Gly Pro Gly Gly Glu Gly
        195                 200                 205

Ser Val His Leu Ala Ser Ser Arg Gly Thr Leu Ser Asp Ser Glu Ile
    210                 215                 220

Glu Thr Asn Ser Ala Thr Ser Thr Ile Phe Gly Lys Ala His Ser Leu
225                 230                 235                 240

Lys Pro Ser Ile Lys Glu Lys Leu Ala Gly Ser Pro Ile Arg Thr Ser
                245                 250                 255

Glu Asp Val Ser Gln Arg Val Tyr Leu Tyr Glu Gly Leu Leu Gly Lys
            260                 265                 270

Glu Arg Ser Thr Leu Trp Asp Gln Met Gln Phe Trp Glu Asp Ala Phe
        275                 280                 285

Leu Asp Ala Val Met Leu Glu Arg Glu Gly Met Gly Met Asp Gln Gly
    290                 295                 300

Pro Gln Glu Met Ile Asp Arg Tyr Leu Ser Leu Gly Glu His Asp Arg
305                 310                 315                 320

Lys Arg Leu Glu Asp Asp Glu Asp Arg Leu Leu Ala Thr Leu Leu His
                325                 330                 335

Asn Leu Ile Ser Tyr Met Leu Leu Met Lys Val Asn Lys Asn Asp Ile
            340                 345                 350

Arg Lys Lys Val Arg Arg Leu Met Gly Lys Ser His Ile Gly Leu Val
        355                 360                 365

Tyr Ser Gln Gln Ile Asn Glu Val Leu Asp Gln Leu Ala Asn Leu Asn
    370                 375                 380

Gly Arg Asp Leu Ser Ile Trp Ser Ser Gly Ser Arg His Met Lys Lys
385                 390                 395                 400

Gln Thr Phe Val Val His Ala Gly Thr Asp Thr Asn Gly Asp Ile Phe
                405                 410                 415
```

```
Phe  Met  Glu  Val  Cys  Asp  Asp  Cys  Val  Val  Leu  Arg  Ser  Asn  Ile  Gly
          420                     425                     430

Thr  Val  Tyr  Glu  Arg  Trp  Trp  Tyr  Glu  Lys  Leu  Ile  Asn  Met  Thr  Tyr
          435                     440                     445

Cys  Pro  Lys  Thr  Lys  Val  Leu  Cys  Leu  Trp  Arg  Arg  Asn  Gly  Ser  Glu
          450                     455                     460

Thr  Gln  Leu  Asn  Lys  Phe  Tyr  Thr  Lys  Lys  Cys  Arg  Glu  Leu  Tyr  Tyr
465                      470                     475                          480

Cys  Val  Lys  Asp  Ser  Met  Glu  Arg  Ala  Ala  Ala  Arg  Gln  Gln  Ser  Ile
               485                     490                     495

Lys  Pro  Gly  Pro  Glu  Leu  Gly  Gly  Glu  Phe  Pro  Val  Gln  Asp  Leu  Lys
          500                     505                     510

Thr  Gly  Glu  Gly  Gly  Leu  Leu  Gln  Val  Thr  Leu  Glu  Gly  Ile  Asn  Leu
          515                     520                     525

Lys  Phe  Met  His  Asn  Gln  Val  Phe  Ile  Glu  Leu  Asn  His  Ile  Lys  Lys
          530                     535                     540

Cys  Asn  Thr  Val  Arg  Gly  Val  Phe  Val  Leu  Glu  Glu  Phe  Val  Pro  Glu
545                      550                     555                          560

Ile  Lys  Glu  Val  Val  Ser  His  Lys  Tyr  Lys  Thr  Pro  Met  Ala  His  Glu
               565                     570                     575

Ile  Cys  Tyr  Ser  Val  Leu  Cys  Leu  Phe  Ser  Tyr  Val  Ala  Ala  Val  His
          580                     585                     590

Ser  Ser  Glu  Glu  Asp  Leu  Arg  Thr  Pro  Pro  Arg  Pro  Val  Ser  Ser
          595                     600                     605
```

( 2 ) INFORMATION FOR SEQ ID NO:13:

( i ) SEQUENCE CHARACTERISTICS:
        ( A ) LENGTH: 3225 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 3..2846

( x i ) SEQUENCE DESCRIPTION: SEQ ID NO:13:

```
CC  CAG  ACT  CGC  CCC  GCC  CCA  GAG  ACT  GCG  CCT  GCG  CGG  GCA  CGA  GAC      47
    Gln  Thr  Arg  Pro  Ala  Pro  Glu  Thr  Ala  Pro  Ala  Arg  Ala  Arg  Asp
    1                   5                        10                      15

ACC  CTC  TCC  GCG  ATG  ACT  GCC  AGC  TCA  GTG  GAG  CAG  CTG  CGG  AAG  GAG      95
Thr  Leu  Ser  Ala  Met  Thr  Ala  Ser  Ser  Val  Glu  Gln  Leu  Arg  Lys  Glu
                    20                       25                      30

GGC  AAT  GAG  CTG  TTC  AAA  TGT  GGA  GAC  TAC  GGG  GGC  GCC  CTG  GCG  GCC     143
Gly  Asn  Glu  Leu  Phe  Lys  Cys  Gly  Asp  Tyr  Gly  Gly  Ala  Leu  Ala  Ala
               35                       40                      45

TAC  ACT  CAG  GCC  CTG  GGT  CTG  GAC  GCG  ACG  CCC  CAG  GAC  CAG  GCC  GTT     191
Tyr  Thr  Gln  Ala  Leu  Gly  Leu  Asp  Ala  Thr  Pro  Gln  Asp  Gln  Ala  Val
          50                       55                      60

CTG  CAC  CGG  AAC  CGG  GCC  GCC  TGC  CAC  CTC  AAG  CTG  GAA  GAT  TAC  GAC     239
Leu  His  Arg  Asn  Arg  Ala  Ala  Cys  His  Leu  Lys  Leu  Glu  Asp  Tyr  Asp
     65                       70                      75

AAA  GCA  GAA  ACA  GAG  GCA  TCC  AAA  GCC  ATT  GAA  AAG  GAT  GGT  GGG  GAT     287
Lys  Ala  Glu  Thr  Glu  Ala  Ser  Lys  Ala  Ile  Glu  Lys  Asp  Gly  Gly  Asp
80                       85                      90                          95
```

```
GTC AAA GCA CTC TAC CGG CGG AGC CAA GCC CTA GAG AAG CTG GGC CGC      335
Val Lys Ala Leu Tyr Arg Arg Ser Gln Ala Leu Glu Lys Leu Gly Arg
            100                 105                 110

CTG GAC CAG GCT GTC CTT GAC CTG CAG AGA TGT GTG AGC TTG GAG CCC      383
Leu Asp Gln Ala Val Leu Asp Leu Gln Arg Cys Val Ser Leu Glu Pro
            115                 120                 125

AAG AAC AAA GTT TTC CAG GAG GCC TTG CGG AAC ATC GGG GGC CAG ATT      431
Lys Asn Lys Val Phe Gln Glu Ala Leu Arg Asn Ile Gly Gly Gln Ile
            130                 135                 140

CAG GAG AAG GTG CGA TAC ATG TCC TCG ACG GAT GCC AAA GTG GAA CAG      479
Gln Glu Lys Val Arg Tyr Met Ser Ser Thr Asp Ala Lys Val Glu Gln
            145                 150                 155

ATG TTT CAG ATA CTG TTG GAC CCA GAA GAG AAG GGC ACT GAG AAA AAG      527
Met Phe Gln Ile Leu Leu Asp Pro Glu Glu Lys Gly Thr Glu Lys Lys
160                 165                 170                 175

CAA AAG GCT TCT CAG AAC CTG GTG GTG CTG GCC AGG GAG GAT GCT GGA      575
Gln Lys Ala Ser Gln Asn Leu Val Val Leu Ala Arg Glu Asp Ala Gly
            180                 185                 190

GCG GAG AAG ATC TTC CGG AGT AAT GGG GTT CAG CTC TTG CAA CGT TTA      623
Ala Glu Lys Ile Phe Arg Ser Asn Gly Val Gln Leu Leu Gln Arg Leu
            195                 200                 205

CTG GAC ATG GGA GAG ACT GAC CTC ATG CTG GCG GCT CTG CGT ACG CTG      671
Leu Asp Met Gly Glu Thr Asp Leu Met Leu Ala Ala Leu Arg Thr Leu
            210                 215                 220

GTT GGC ATT TGC TCT GAG CAT CAG TCA CGG ACA GTG GCA ACC CTG AGC      719
Val Gly Ile Cys Ser Glu His Gln Ser Arg Thr Val Ala Thr Leu Ser
            225                 230                 235

ATA CTG GGA ACT CGG CGA GTA GTC TCC ATC CTG GGC GTG GAA AGC CAG      767
Ile Leu Gly Thr Arg Arg Val Val Ser Ile Leu Gly Val Glu Ser Gln
240                 245                 250                 255

GCT GTG TCC CTG GCT GCC TGC CAC CTG CTG CAG GTT ATG TTT GAT GCC      815
Ala Val Ser Leu Ala Ala Cys His Leu Leu Gln Val Met Phe Asp Ala
            260                 265                 270

CTC AAG GAA GGT GTC AAA AAA GGC TTC CGA GGC AAA GAA GGT GCC ATC      863
Leu Lys Glu Gly Val Lys Lys Gly Phe Arg Gly Lys Glu Gly Ala Ile
            275                 280                 285

ATT GTG GAT CCT GCC CGG GAG CTG AAG GTC CTC ATC AGT AAC CTC TTA      911
Ile Val Asp Pro Ala Arg Glu Leu Lys Val Leu Ile Ser Asn Leu Leu
            290                 295                 300

GAT CTG CTG ACA GAG GTG GGG GTC TCT GGC CAA GGC CGA GAC AAT GCC      959
Asp Leu Leu Thr Glu Val Gly Val Ser Gly Gln Gly Arg Asp Asn Ala
            305                 310                 315

CTG ACC CTC CTG ATT AAA GCG GTG CCC CGG AAG TCT CTC AAG GAC CCC      1007
Leu Thr Leu Leu Ile Lys Ala Val Pro Arg Lys Ser Leu Lys Asp Pro
320                 325                 330                 335

AAC AAC AGC CTC ACC CTC TGG GTC ATC GAC CAA GGT CTG AAA AAG ATT      1055
Asn Asn Ser Leu Thr Leu Trp Val Ile Asp Gln Gly Leu Lys Lys Ile
            340                 345                 350

TTG GAA GTG GGG GGC TCT CTA CAG GAC CCT CCT GGG GAG CTC GCA GTG      1103
Leu Glu Val Gly Gly Ser Leu Gln Asp Pro Pro Gly Glu Leu Ala Val
            355                 360                 365

ACC GCA AAC AGC CGC ATG AGC GCC TCT ATT CTC CTC AGC AAG CTC TTT      1151
Thr Ala Asn Ser Arg Met Ser Ala Ser Ile Leu Leu Ser Lys Leu Phe
            370                 375                 380

GAT GAC CTC AAG TGT GAT GCG GAG AGG GAG AAT TTC CAC AGA CTT TGT      1199
Asp Asp Leu Lys Cys Asp Ala Glu Arg Glu Asn Phe His Arg Leu Cys
            385                 390                 395

GAA AAC TAC ATC AAG AGC TGG TTT GAG GGC CAA GGG CTG GCC GGG AAG      1247
Glu Asn Tyr Ile Lys Ser Trp Phe Glu Gly Gln Gly Leu Ala Gly Lys
400                 405                 410                 415
```

-continued

| | | | | | | | | | | | | | | | | |
|---|---|---|---|---|---|---|---|---|---|---|---|---|---|---|---|---|
| CTA | CGG | GCC | ATC | CAG | ACG | GTG | TCC | TGC | CTC | CTG | CAG | GGC | CCA | TGT | GAC | 1295 |
| Leu | Arg | Ala | Ile | Gln<br>420 | Thr | Val | Ser | Cys | Leu<br>425 | Leu | Gln | Gly | Pro | Cys<br>430 | Asp | |
| GCT | GGC | AAC | CGG | GCC | TTG | GAG | CTG | AGC | GGT | GTC | ATG | GAG | AGT | GTG | ATT | 1343 |
| Ala | Gly | Asn | Arg<br>435 | Ala | Leu | Glu | Leu | Ser<br>440 | Gly | Val | Met | Glu | Ser<br>445 | Val | Ile | |
| GCT | CTG | TGT | GCC | TCT | GAG | CAG | GAG | GAG | GAG | CAG | CTG | GTG | GCC | GTG | GAG | 1391 |
| Ala | Leu | Cys<br>450 | Ala | Ser | Glu | Gln | Glu<br>455 | Glu | Glu | Gln | Leu | Val<br>460 | Ala | Val | Glu | |
| GCT | CTG | ATC | CAT | GCA | GCC | GGC | AAG | GCT | AAG | CGG | GCC | TCA | TTC | ATC | ACT | 1439 |
| Ala | Leu | Ile<br>465 | His | Ala | Ala | Gly | Lys<br>470 | Ala | Lys | Arg | Ala<br>475 | Ser | Phe | Ile | Thr | |
| GCC | AAT | GGT | GTC | TCG | CTG | CTG | AAG | GAC | CTA | TAT | AAG | TGC | AGC | GAG | AAG | 1487 |
| Ala<br>480 | Asn | Gly | Val | Ser | Leu<br>485 | Leu | Lys | Asp | Leu | Tyr<br>490 | Lys | Cys | Ser | Glu | Lys<br>495 | |
| GAC | AGC | ATC | CGC | ATC | CGG | GCG | CTA | GTG | GGA | CTC | TGT | AAG | CTC | GGT | TCG | 1535 |
| Asp | Ser | Ile | Arg | Ile<br>500 | Arg | Ala | Leu | Val | Gly<br>505 | Leu | Cys | Lys | Leu | Gly<br>510 | Ser | |
| GCT | GGA | GGG | ACT | GAC | TTC | AGC | ATG | AAG | CAG | TTT | GCT | GAA | GGC | TCC | ACT | 1583 |
| Ala | Gly | Gly | Thr<br>515 | Asp | Phe | Ser | Met | Lys<br>520 | Gln | Phe | Ala | Glu | Gly<br>525 | Ser | Thr | |
| CTC | AAA | CTG | GCT | AAG | CAG | TGT | CGA | AAG | TGG | CTG | TGC | AAT | GAC | CAG | ATC | 1631 |
| Leu | Lys | Leu<br>530 | Ala | Lys | Gln | Cys | Arg<br>535 | Lys | Trp | Leu | Cys | Asn<br>540 | Asp | Gln | Ile | |
| GAC | GCA | GGC | ACT | CGG | CGC | TGG | GCA | GTG | GAG | GGC | CTG | GCT | TAC | CTG | ACC | 1679 |
| Asp | Ala<br>545 | Gly | Thr | Arg | Arg | Trp<br>550 | Ala | Val | Glu | Gly | Leu<br>555 | Ala | Tyr | Leu | Thr | |
| TTT | GAT | GCC | GAC | GTG | AAG | GAA | GAG | TTT | GTG | GAG | GAT | GCG | GCT | GCT | CTG | 1727 |
| Phe<br>560 | Asp | Ala | Asp | Val | Lys<br>565 | Glu | Glu | Phe | Val | Glu<br>570 | Asp | Ala | Ala | Ala | Leu<br>575 | |
| AAA | GCT | CTG | TTC | CAG | CTC | AGC | AGG | TTG | GAG | GAG | AGG | TCA | GTG | CTC | TTT | 1775 |
| Lys | Ala | Leu | Phe | Gln<br>580 | Leu | Ser | Arg | Leu | Glu<br>585 | Glu | Arg | Ser | Val | Leu<br>590 | Phe | |
| GCG | GTG | GCC | TCA | GCG | CTG | GTG | AAC | TGC | ACC | AAC | AGC | TAT | GAC | TAC | GAG | 1823 |
| Ala | Val | Ala | Ser<br>595 | Ala | Leu | Val | Asn | Cys<br>600 | Thr | Asn | Ser | Tyr | Asp<br>605 | Tyr | Glu | |
| GAG | CCC | GAC | CCC | AAG | ATG | GTG | GAG | CTG | GCC | AAG | TAT | GCC | AAG | CAG | CAT | 1871 |
| Glu | Pro | Asp<br>610 | Pro | Lys | Met | Val | Glu<br>615 | Leu | Ala | Lys | Tyr | Ala<br>620 | Lys | Gln | His | |
| GTG | CCC | GAG | CAG | CAC | CCC | AAG | GAC | AAG | CCA | AGC | TTC | GTG | CGG | GCT | CGG | 1919 |
| Val | Pro | Glu<br>625 | Gln | His | Pro | Lys | Asp<br>630 | Lys | Pro | Ser | Phe | Val<br>635 | Arg | Ala | Arg | |
| GTG | AAG | AAG | CTG | CTG | GCA | GCG | GGT | GTG | GTG | TCG | GCC | ATG | GTG | TGC | ATG | 1967 |
| Val | Lys<br>640 | Lys | Leu | Leu | Ala | Ala<br>645 | Gly | Val | Val | Ser | Ala<br>650 | Met | Val | Cys | Met<br>655 | |
| GTG | AAG | ACG | GAG | AGC | CCT | GTG | CTG | ACC | AGT | TCC | TGC | AGA | GAG | CTG | CTC | 2015 |
| Val | Lys | Thr | Glu | Ser<br>660 | Pro | Val | Leu | Thr | Ser<br>665 | Ser | Cys | Arg | Glu | Leu<br>670 | Leu | |
| TCC | AGG | GTC | TTC | TTG | GCT | TTA | GTG | GAA | GAG | GTA | GAG | GAC | CGA | GGC | ACT | 2063 |
| Ser | Arg | Val | Phe<br>675 | Leu | Ala | Leu | Val | Glu<br>680 | Glu | Val | Glu | Asp | Arg<br>685 | Gly | Thr | |
| GTG | GTT | GCC | CAG | GGA | GGC | GGC | AGG | GCG | CTG | ATC | CCG | CTG | GCC | CTG | GAA | 2111 |
| Val | Val | Ala | Gln<br>690 | Gly | Gly | Gly | Arg<br>695 | Ala | Leu | Ile | Pro<br>700 | Leu | Ala | Leu | Glu | |
| GGC | ACG | GAC | GTG | GGG | CAG | ACA | AAG | GCA | GCC | CAG | GCC | CTT | GCC | AAG | CTC | 2159 |
| Gly | Thr | Asp<br>705 | Val | Gly | Gln | Thr | Lys<br>710 | Ala | Ala | Gln | Ala<br>715 | Leu | Ala | Lys | Leu | |
| ACC | ATC | ACC | TCC | AAC | CCG | GAG | ATG | ACC | TTC | CCT | GGC | GAG | CGG | ATC | TAT | 2207 |
| Thr | Ile | Thr<br>720 | Ser | Asn | Pro | Glu | Met<br>725 | Thr | Phe | Pro | Gly<br>730 | Glu | Arg | Ile | Tyr<br>735 | |

| | | | | | | | | | | | | | | | | |
|---|---|---|---|---|---|---|---|---|---|---|---|---|---|---|---|---|
| GAG | GTG | GTC | CGG | CCC | CTC | GTC | TCC | CTG | TTG | CAC | CTC | AAC | TGC | TCA | GGC | 2255 |
| Glu | Val | Val | Arg | Pro | Leu | Val | Ser | Leu | Leu | His | Leu | Asn | Cys | Ser | Gly | |
| | | | 740 | | | | | 745 | | | | | 750 | | | |
| CTG | CAG | AAC | TTC | GAG | GCG | CTC | ATG | GCC | CTA | ACA | AAC | CTG | GCT | GGG | ATC | 2303 |
| Leu | Gln | Asn | Phe | Glu | Ala | Leu | Met | Ala | Leu | Thr | Asn | Leu | Ala | Gly | Ile | |
| | | | 755 | | | | | 760 | | | | | 765 | | | |
| AGC | GAG | AGG | CTC | CGG | CAG | AAG | ATC | CTG | AAG | GAG | AAG | GCT | GTG | CCC | ATG | 2351 |
| Ser | Glu | Arg | Leu | Arg | Gln | Lys | Ile | Leu | Lys | Glu | Lys | Ala | Val | Pro | Met | |
| | | 770 | | | | | 775 | | | | | 780 | | | | |
| ATA | GAA | GGC | TAC | ATG | TTT | GAG | GAG | CAT | GAG | ATG | ATC | CGC | CGG | GCA | GCC | 2399 |
| Ile | Glu | Gly | Tyr | Met | Phe | Glu | Glu | His | Glu | Met | Ile | Arg | Arg | Ala | Ala | |
| | 785 | | | | | 790 | | | | | 795 | | | | | |
| ACG | GAG | TGC | ATG | TGT | AAC | TTG | GCC | ATG | AGC | AAG | GAG | GTG | CAG | GAC | CTC | 2447 |
| Thr | Glu | Cys | Met | Cys | Asn | Leu | Ala | Met | Ser | Lys | Glu | Val | Gln | Asp | Leu | |
| 800 | | | | | 805 | | | | | 810 | | | | | 815 | |
| TTC | GAA | GCC | CAG | GGC | AAT | GAC | CGA | CTG | AAG | CTG | CTG | GTG | CTG | TAC | AGT | 2495 |
| Phe | Glu | Ala | Gln | Gly | Asn | Asp | Arg | Leu | Lys | Leu | Leu | Val | Leu | Tyr | Ser | |
| | | | | 820 | | | | | 825 | | | | | 830 | | |
| GGA | GAG | GAT | GAT | GAG | CTG | CTA | CAG | CGG | GCA | GCT | GCC | GGG | GGC | TTG | GCC | 2543 |
| Gly | Glu | Asp | Asp | Glu | Leu | Leu | Gln | Arg | Ala | Ala | Ala | Gly | Gly | Leu | Ala | |
| | | | 835 | | | | | 840 | | | | | 845 | | | |
| ATG | CTT | ACC | TCC | ATG | CGG | CCC | ACG | CTC | TGC | AGC | CGC | ATT | CCC | CAA | GTG | 2591 |
| Met | Leu | Thr | Ser | Met | Arg | Pro | Thr | Leu | Cys | Ser | Arg | Ile | Pro | Gln | Val | |
| | | 850 | | | | | 855 | | | | | 860 | | | | |
| ACC | ACA | CAC | TGG | CTG | GAG | ATC | CTG | CAG | GCC | CTG | CTT | CTG | AGC | TCC | AAC | 2639 |
| Thr | Thr | His | Trp | Leu | Glu | Ile | Leu | Gln | Ala | Leu | Leu | Leu | Ser | Ser | Asn | |
| | 865 | | | | | 870 | | | | | 875 | | | | | |
| CAG | GAG | CTG | CAG | CAC | CGG | GGT | GCT | GTG | GTG | GTG | CTG | AAC | ATG | GTG | GAG | 2687 |
| Gln | Glu | Leu | Gln | His | Arg | Gly | Ala | Val | Val | Val | Leu | Asn | Met | Val | Glu | |
| 880 | | | | | 885 | | | | | 890 | | | | | 895 | |
| GCC | TCG | AGG | GAG | ATT | GCC | AGC | ACC | CTG | ATG | GAG | AGT | GAG | ATG | ATG | GAG | 2735 |
| Ala | Ser | Arg | Glu | Ile | Ala | Ser | Thr | Leu | Met | Glu | Ser | Glu | Met | Met | Glu | |
| | | | | 900 | | | | | 905 | | | | | 910 | | |
| ATC | TTG | TCA | GTG | CTA | GCT | AAG | GGT | GAC | CAC | AGC | CCT | GTC | ACA | AGG | GCT | 2783 |
| Ile | Leu | Ser | Val | Leu | Ala | Lys | Gly | Asp | His | Ser | Pro | Val | Thr | Arg | Ala | |
| | | | 915 | | | | | 920 | | | | | 925 | | | |
| GCT | GCA | GCC | TGC | CTG | GAC | AAA | GCA | GTG | GAA | TAT | GGG | CTT | ATC | CAA | CCC | 2831 |
| Ala | Ala | Ala | Cys | Leu | Asp | Lys | Ala | Val | Glu | Tyr | Gly | Leu | Ile | Gln | Pro | |
| | | 930 | | | | | 935 | | | | | 940 | | | | |
| AAC | CAA | GAT | GGA | GAG | TGAGGGGTT | GTCCCTGGGC | CCAAGGCTCA | TGCACACGCT | | | | | | | | 2886 |
| Asn | Gln | Asp | Gly | Glu | | | | | | | | | | | | |
| | | 945 | | | | | | | | | | | | | | |

| | | |
|---|---|---|
| ACCTATTGTG GCACGGAGAG TAAGGACGGA AGCAGCTTTG GCTGGTGGTG GCTGGCATGC | 2946 |
| CCAATACTCT TGCCCATCCT CGCTTGCTGC CCTAGGATGT CCTCTGTTCT GAGTCAGCGG | 3006 |
| CCACGTTCAG TCACACAGCC CTGCTTGGCC AGCACTGCCT GCAGCCTCAC TCAGAGGGGC | 3066 |
| CCTTTTTCTG TACTACTGTA GTCAGCTGGG AATGGGAAG GTGCATCCCA ACACAGCCTG | 3126 |
| TGGATCCTGG GGCATTTGGA AGGGCGCACA CATCAGCAGC CTCACCAGCT GTGAGCCTGC | 3186 |
| TATCAGGCCT GCCCCTCCAA TAAAAGTGTG TAGAACTCC | 3225 |

( 2 ) INFORMATION FOR SEQ ID NO:14:

( i ) SEQUENCE CHARACTERISTICS:
        ( A ) LENGTH: 948 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Gln Thr Arg Pro Ala Pro Glu Thr Ala Pro Ala Arg Ala Arg Asp Thr
 1               5               10              15
Leu Ser Ala Met Thr Ala Ser Ser Val Glu Gln Leu Arg Lys Glu Gly
                20              25              30
Asn Glu Leu Phe Lys Cys Gly Asp Tyr Gly Gly Ala Leu Ala Ala Tyr
            35              40              45
Thr Gln Ala Leu Gly Leu Asp Ala Thr Pro Gln Asp Gln Ala Val Leu
        50              55              60
His Arg Asn Arg Ala Ala Cys His Leu Lys Leu Glu Asp Tyr Asp Lys
65              70              75                              80
Ala Glu Thr Glu Ala Ser Lys Ala Ile Glu Lys Asp Gly Gly Asp Val
                85              90              95
Lys Ala Leu Tyr Arg Arg Ser Gln Ala Leu Glu Lys Leu Gly Arg Leu
            100             105             110
Asp Gln Ala Val Leu Asp Leu Gln Arg Cys Val Ser Leu Glu Pro Lys
        115             120             125
Asn Lys Val Phe Gln Glu Ala Leu Arg Asn Ile Gly Gly Gln Ile Gln
    130             135             140
Glu Lys Val Arg Tyr Met Ser Ser Thr Asp Ala Lys Val Glu Gln Met
145             150             155                             160
Phe Gln Ile Leu Leu Asp Pro Glu Glu Lys Gly Thr Glu Lys Lys Gln
                165             170             175
Lys Ala Ser Gln Asn Leu Val Val Leu Ala Arg Glu Asp Ala Gly Ala
            180             185             190
Glu Lys Ile Phe Arg Ser Asn Gly Val Gln Leu Leu Gln Arg Leu Leu
        195             200             205
Asp Met Gly Glu Thr Asp Leu Met Leu Ala Ala Leu Arg Thr Leu Val
    210             215             220
Gly Ile Cys Ser Glu His Gln Ser Arg Thr Val Ala Thr Leu Ser Ile
225             230             235                             240
Leu Gly Thr Arg Arg Val Val Ser Ile Leu Gly Val Glu Ser Gln Ala
                245             250             255
Val Ser Leu Ala Ala Cys His Leu Leu Gln Val Met Phe Asp Ala Leu
            260             265             270
Lys Glu Gly Val Lys Lys Gly Phe Arg Gly Lys Glu Gly Ala Ile Ile
        275             280             285
Val Asp Pro Ala Arg Glu Leu Lys Val Leu Ile Ser Asn Leu Leu Asp
    290             295             300
Leu Leu Thr Glu Val Gly Val Ser Gly Gln Gly Arg Asp Asn Ala Leu
305             310             315                             320
Thr Leu Leu Ile Lys Ala Val Pro Arg Lys Ser Leu Lys Asp Pro Asn
                325             330             335
Asn Ser Leu Thr Leu Trp Val Ile Asp Gln Gly Leu Lys Lys Ile Leu
            340             345             350
Glu Val Gly Gly Ser Leu Gln Asp Pro Pro Gly Glu Leu Ala Val Thr
        355             360             365
Ala Asn Ser Arg Met Ser Ala Ser Ile Leu Leu Ser Lys Leu Phe Asp
    370             375             380
Asp Leu Lys Cys Asp Ala Glu Arg Glu Asn Phe His Arg Leu Cys Glu
385             390             395                             400
Asn Tyr Ile Lys Ser Trp Phe Glu Gly Gln Gly Leu Ala Gly Lys Leu
                405             410             415
Arg Ala Ile Gln Thr Val Ser Cys Leu Leu Gln Gly Pro Cys Asp Ala
            420             425             430
```

-continued

| | | | | | | | | | | | | | | |
|---|---|---|---|---|---|---|---|---|---|---|---|---|---|---|
| Gly | Asn | Arg 435 | Ala | Leu | Glu | Leu 440 | Ser | Gly | Val | Met | Glu | Ser 445 | Val | Ile | Ala |
| Leu | Cys 450 | Ala | Ser | Glu | Gln 455 | Glu | Glu | Gln | Leu | Val 460 | Ala | Val | Glu | Ala |
| Leu 465 | Ile | His | Ala | Ala 470 | Gly | Lys | Ala | Lys | Arg 475 | Ala | Ser | Phe | Ile | Thr | Ala 480 |
| Asn | Gly | Val | Ser | Leu 485 | Leu | Lys | Asp | Leu | Tyr 490 | Lys | Cys | Ser | Glu | Lys 495 | Asp |
| Ser | Ile | Arg | Ile 500 | Arg | Ala | Leu | Val | Gly 505 | Leu | Cys | Lys | Leu | Gly 510 | Ser | Ala |
| Gly | Gly | Thr 515 | Asp | Phe | Ser | Met | Lys 520 | Gln | Phe | Ala | Glu | Gly 525 | Ser | Thr | Leu |
| Lys | Leu 530 | Ala | Lys | Gln | Cys | Arg 535 | Lys | Trp | Leu | Cys | Asn 540 | Asp | Gln | Ile | Asp |
| Ala 545 | Gly | Thr | Arg | Arg | Trp 550 | Ala | Val | Glu | Gly | Leu 555 | Ala | Tyr | Leu | Thr | Phe 560 |
| Asp | Ala | Asp | Val | Lys 565 | Glu | Glu | Phe | Val | Glu 570 | Asp | Ala | Ala | Ala | Leu 575 | Lys |
| Ala | Leu | Phe | Gln 580 | Leu | Ser | Arg | Leu | Glu 585 | Glu | Arg | Ser | Val | Leu 590 | Phe | Ala |
| Val | Ala | Ser 595 | Ala | Leu | Val | Asn | Cys 600 | Thr | Asn | Ser | Tyr | Asp 605 | Tyr | Glu | Glu |
| Pro | Asp 610 | Pro | Lys | Met | Val | Glu 615 | Leu | Ala | Lys | Tyr | Ala 620 | Lys | Gln | His | Val |
| Pro 625 | Glu | Gln | His | Pro | Lys 630 | Asp | Lys | Pro | Ser | Phe 635 | Val | Arg | Ala | Arg | Val 640 |
| Lys | Lys | Leu | Leu | Ala 645 | Ala | Gly | Val | Val | Ser 650 | Ala | Met | Val | Cys | Met 655 | Val |
| Lys | Thr | Glu | Ser 660 | Pro | Val | Leu | Thr | Ser 665 | Ser | Cys | Arg | Glu | Leu 670 | Leu | Ser |
| Arg | Val | Phe 675 | Leu | Ala | Leu | Val | Glu 680 | Glu | Val | Glu | Asp | Arg 685 | Gly | Thr | Val |
| Val | Ala 690 | Gln | Gly | Gly | Gly | Arg 695 | Ala | Leu | Ile | Pro | Leu 700 | Ala | Leu | Glu | Gly |
| Thr 705 | Asp | Val | Gly | Gln | Thr 710 | Lys | Ala | Ala | Gln | Ala 715 | Leu | Ala | Lys | Leu | Thr 720 |
| Ile | Thr | Ser | Asn | Pro 725 | Glu | Met | Thr | Phe | Pro 730 | Gly | Glu | Arg | Ile | Tyr 735 | Glu |
| Val | Val | Arg | Pro 740 | Leu | Val | Ser | Leu | Leu 745 | His | Leu | Asn | Cys | Ser 750 | Gly | Leu |
| Gln | Asn | Phe 755 | Glu | Ala | Leu | Met | Ala 760 | Leu | Thr | Asn | Leu | Ala 765 | Gly | Ile | Ser |
| Glu | Arg 770 | Leu | Arg | Gln | Lys | Ile 775 | Leu | Lys | Glu | Lys | Ala 780 | Val | Pro | Met | Ile |
| Glu 785 | Gly | Tyr | Met | Phe | Glu 790 | Glu | His | Glu | Met | Ile 795 | Arg | Arg | Ala | Ala | Thr 800 |
| Glu | Cys | Met | Cys | Asn 805 | Leu | Ala | Met | Ser | Lys 810 | Glu | Val | Gln | Asp | Leu 815 | Phe |
| Glu | Ala | Gln | Gly 820 | Asn | Asp | Arg | Leu | Lys 825 | Leu | Leu | Val | Leu | Tyr 830 | Ser | Gly |
| Glu | Asp | Asp 835 | Glu | Leu | Leu | Gln | Arg 840 | Ala | Ala | Ala | Gly | Gly 845 | Leu | Ala | Met |
| Leu | Thr | Ser | Met | Arg | Pro | Thr | Leu | Cys | Ser | Arg | Ile | Pro | Gln | Val | Thr |

-continued

|     |     |     |     | 850 |     |     |     |     | 855 |     |     |     |     | 860 |     |     |     |     |
|-----|-----|-----|-----|-----|-----|-----|-----|-----|-----|-----|-----|-----|-----|-----|-----|-----|-----|-----|
| Thr | His | Trp | Leu | Glu | Ile | Leu | Gln | Ala | Leu | Leu | Leu | Ser | Ser | Asn | Gln |
| 865 |     |     |     |     | 870 |     |     |     |     | 875 |     |     |     |     | 880 |

Glu Leu Gln His Arg Gly Ala Val Val Val Leu Asn Met Val Glu Ala
              885                 890                 895

Ser Arg Glu Ile Ala Ser Thr Leu Met Glu Ser Glu Met Met Glu Ile
            900                 905                 910

Leu Ser Val Leu Ala Lys Gly Asp His Ser Pro Val Thr Arg Ala Ala
        915                 920                 925

Ala Ala Cys Leu Asp Lys Ala Val Glu Tyr Gly Leu Ile Gln Pro Asn
930                     935                     940

Gln Asp Gly Glu
945

( 2 ) INFORMATION FOR SEQ ID NO:15:

( i ) SEQUENCE CHARACTERISTICS:
        ( A ) LENGTH: 6002 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 326..5092

( x i ) SEQUENCE DESCRIPTION: SEQ ID NO:15:

```
CACGTGCATG TGTAGCATGC CTTGGTTTTT CCTTTGGCAT CTGAAAAAGG CACAACCTGA      60

AAGACCTAGA ACCCAGTGTC GGTCCCCAGG CCCTTTGGGA CAGGAAGAGA GAGCCGTGT      120

GGCCGCGGGG AGGATGTCCT GCGGCGGGGC TGTCCTCGCG GACTGACTGG ACTCCATCTC     180

CCAGCGGGCG CCGCGGCGCG GCCACGCCCC CCCACTCCCC GCGCGCGCCC GGTGGAGACT     240

TCGATTTTCA GAATTCCTCC TGGGAATGCT GACTCCTTGC TTGGTGCCCT GATGCTTCTC     300

TGAGATAAAC TGATGAATTG GAACC ATG GTG CAA AAG AAG AAG TTC TGT CCT       352
                            Met Val Gln Lys Lys Lys Phe Cys Pro
                             1               5
```

CGG TTA CTT GAC TAT CTA GTG ATC GTA GGG GCC AGG CAC CCG AGC AGT      400
Arg Leu Leu Asp Tyr Leu Val Ile Val Gly Ala Arg His Pro Ser Ser
 10              15                  20                  25

GAT AGC GTG GCC CAG ACT CCT GAA TTG CTA CGG CGA TAC CCC TTG GAG      448
Asp Ser Val Ala Gln Thr Pro Glu Leu Leu Arg Arg Tyr Pro Leu Glu
            30                  35                  40

GAT CAC ACT GAG TTT CCC CTG CCC CCA GAT GTA GTG TTC TTC TGC CAG      496
Asp His Thr Glu Phe Pro Leu Pro Pro Asp Val Val Phe Phe Cys Gln
        45                  50                  55

CCC GAG GGC TGC CTG AGC GTG CGG CAG CGG CGC ATG AGC CTT CGG GAT      544
Pro Glu Gly Cys Leu Ser Val Arg Gln Arg Arg Met Ser Leu Arg Asp
    60                  65                  70

GAT ACC TCT TTT GTC TTC ACC CTC ACT GAC AAG GAC ACT GGA GTC ACG      592
Asp Thr Ser Phe Val Phe Thr Leu Thr Asp Lys Asp Thr Gly Val Thr
75                  80                  85

CGA TAT GGC ATC TGT GTT AAC TTC TAC CGC TCC TTC CAA AAG CGA ATC      640
Arg Tyr Gly Ile Cys Val Asn Phe Tyr Arg Ser Phe Gln Lys Arg Ile
 90                  95                 100                 105

TCT AAG GAG AAG GGG GAA GGT GGG GCA GGG TCC CGT GGG AAG GAA GGA      688
Ser Lys Glu Lys Gly Glu Gly Gly Ala Gly Ser Arg Gly Lys Glu Gly
                110                 115                 120

-continued

```
ACC CAT GCC ACC TGT GCC TCA GAA GAG GGT GGC ACT GAG AGC TCA GAG     736
Thr His Ala Thr Cys Ala Ser Glu Glu Gly Gly Thr Glu Ser Ser Glu
        125                 130                 135

AGT GGC TCA TCC CTG CAG CCT CTC AGT GCT GAC TCT ACC CCT GAT GTG     784
Ser Gly Ser Ser Leu Gln Pro Leu Ser Ala Asp Ser Thr Pro Asp Val
        140                 145                 150

AAC CAG TCT CCT CGG GGC AAA CGC CGG GCC AAG GCG GGG AGC CGC TCC     832
Asn Gln Ser Pro Arg Gly Lys Arg Arg Ala Lys Ala Gly Ser Arg Ser
        155                 160                 165

CGC AAC AGT ACT CTC ACG TCC CTG TGC GTG CTC AGC CAC TAC CCT TTC     880
Arg Asn Ser Thr Leu Thr Ser Leu Cys Val Leu Ser His Tyr Pro Phe
170                 175                 180                 185

TTC TCC ACC TTC CGA GAG TGT TTG TAT ACT CTC AAG CGC CTG GTG GAC     928
Phe Ser Thr Phe Arg Glu Cys Leu Tyr Thr Leu Lys Arg Leu Val Asp
                190                 195                 200

TGC TGT AGT GAG CGC CTT CTG GGC AAG AAA CTG GGC ATC CCT CGA GGC     976
Cys Cys Ser Glu Arg Leu Leu Gly Lys Lys Leu Gly Ile Pro Arg Gly
            205                 210                 215

GTA CAA AGG GAC ACC ATG TGG CGG ATC TTT ACT GGA TCG CTG CTG GTA    1024
Val Gln Arg Asp Thr Met Trp Arg Ile Phe Thr Gly Ser Leu Leu Val
        220                 225                 230

GAG GAG AAG TCA AGT GCC CTT CTG CAT GAC CTT CGA GAG ATT GAG GCC    1072
Glu Glu Lys Ser Ser Ala Leu Leu His Asp Leu Arg Glu Ile Glu Ala
        235                 240                 245

TGG ATC TAT CGA TTG CTG CGC TCC CCA GTA CCC GTC TCT GGG CAG AAG    1120
Trp Ile Tyr Arg Leu Leu Arg Ser Pro Val Pro Val Ser Gly Gln Lys
250                 255                 260                 265

CGA GTA GAC ATC GAG GTC CTA CCC CAA GAG CTC CAG CCA GCT CTG ACC    1168
Arg Val Asp Ile Glu Val Leu Pro Gln Glu Leu Gln Pro Ala Leu Thr
                270                 275                 280

TTT GCT CTT CCA GAC CCA TCT CGA TTC ACC CTA GTG GAT TTC CCA CTG    1216
Phe Ala Leu Pro Asp Pro Ser Arg Phe Thr Leu Val Asp Phe Pro Leu
            285                 290                 295

CAC CTT CCC TTG GAA CTT CTA GGT GTG GAC GCC TGT CTC CAG GTG CTA    1264
His Leu Pro Leu Glu Leu Leu Gly Val Asp Ala Cys Leu Gln Val Leu
        300                 305                 310

ACC TGC ATT CTG TTA GAG CAC AAG GTG GTG CTA CAG TCC CGA GAC TAC    1312
Thr Cys Ile Leu Leu Glu His Lys Val Val Leu Gln Ser Arg Asp Tyr
        315                 320                 325

AAT GCA CTC TCC ATG TCT GTG ATG GCA TTC GTG GCA ATG ATC TAC CCA    1360
Asn Ala Leu Ser Met Ser Val Met Ala Phe Val Ala Met Ile Tyr Pro
330                 335                 340                 345

CTG GAA TAT ATG TTT CCT GTC ATC CCG CTG CTA CCC ACC TGC ATG GCA    1408
Leu Glu Tyr Met Phe Pro Val Ile Pro Leu Leu Pro Thr Cys Met Ala
                350                 355                 360

TCA GCA GAG CAG CTG CTG TTG GCT CCA ACC CCG TAC ATC ATT GGG GTT    1456
Ser Ala Glu Gln Leu Leu Leu Ala Pro Thr Pro Tyr Ile Ile Gly Val
            365                 370                 375

CCT GCC AGC TTC TTC CTC TAC AAA CTG GAC TTC AAA ATG CCT GAT GAT    1504
Pro Ala Ser Phe Phe Leu Tyr Lys Leu Asp Phe Lys Met Pro Asp Asp
        380                 385                 390

GTA TGG CTA GTG GAT CTG GAC AGC AAT AGG GTG ATT GCC CCC ACC AAT    1552
Val Trp Leu Val Asp Leu Asp Ser Asn Arg Val Ile Ala Pro Thr Asn
        395                 400                 405

GCA GAA GTG CTG CCT ATC CTG CCA GAA CCA GAA TCA CTA GAG CTG AAA    1600
Ala Glu Val Leu Pro Ile Leu Pro Glu Pro Glu Ser Leu Glu Leu Lys
410                 415                 420                 425

AAG CAT TTA AAG CAG GCC TTG GCC AGC ATG AGT CTC AAC ACC CAG CCC    1648
Lys His Leu Lys Gln Ala Leu Ala Ser Met Ser Leu Asn Thr Gln Pro
                430                 435                 440
```

```
ATC CTC AAT CTG GAG AAA TTT CAT GAG GGC CAG GAG ATC CCC CTT CTC       1696
Ile Leu Asn Leu Glu Lys Phe His Glu Gly Gln Glu Ile Pro Leu Leu
            445                 450                 455

TTG GGA AGG CCT TCT AAT GAC CTG CAG TCC ACA CCG TCC ACT GAA TTC       1744
Leu Gly Arg Pro Ser Asn Asp Leu Gln Ser Thr Pro Ser Thr Glu Phe
        460                 465                 470

AAC CCA CTC ATC TAT GGC AAT GAT GTG GAT TCT GTG GAT GTT GCA ACC       1792
Asn Pro Leu Ile Tyr Gly Asn Asp Val Asp Ser Val Asp Val Ala Thr
    475                 480                 485

AGG GTT GCC ATG GTA CGG TTC TTC AAT TCC GCC AAC GTG CTG CAG GGA       1840
Arg Val Ala Met Val Arg Phe Phe Asn Ser Ala Asn Val Leu Gln Gly
490                 495                 500                 505

TTT CAG ATG CAC ACG CGT ACC CTG CGC CTC TTT CCT CGG CCT GTG GTA       1888
Phe Gln Met His Thr Arg Thr Leu Arg Leu Phe Pro Arg Pro Val Val
                510                 515                 520

GCT TTT CAA GCT GGC TCC TTT CTA GCC TCA CGT CCC CGG CAG ACT CCT       1936
Ala Phe Gln Ala Gly Ser Phe Leu Ala Ser Arg Pro Arg Gln Thr Pro
            525                 530                 535

TTT GCC GAG AAA TTG GCC AGG ACT CAG GCT GTG GAG TAC TTT GGG GAA       1984
Phe Ala Glu Lys Leu Ala Arg Thr Gln Ala Val Glu Tyr Phe Gly Glu
        540                 545                 550

TGG ATC CTT AAC CCC ACC AAC TAT GCC TTT CAG CGA ATT CAC AAC AAT       2032
Trp Ile Leu Asn Pro Thr Asn Tyr Ala Phe Gln Arg Ile His Asn Asn
    555                 560                 565

ATG TTT GAT CCA GCC CTG ATT GGT GAC AAG CCA AAG TGG TAT GCT CAT       2080
Met Phe Asp Pro Ala Leu Ile Gly Asp Lys Pro Lys Trp Tyr Ala His
570                 575                 580                 585

CAG CTG CAG CCT ATC CAC TAT CGC GTC TAT GAC AGC AAT CCC AGC TG       2128
Gln Leu Gln Pro Ile His Tyr Arg Val Tyr Asp Ser Asn Ser Gln Leu
                590                 595                 600

GCT GAG GCC CTG AGT GTA CCA CCA GAG CGG GAC TCT GAC TCC GAA CCT       2176
Ala Glu Ala Leu Ser Val Pro Pro Glu Arg Asp Ser Asp Ser Glu Pro
            605                 610                 615

ACT GAT GAT AGT GGC AGT GAT AGT ATG GAT TAT GAC GAT TCA AGC TCT       2224
Thr Asp Asp Ser Gly Ser Asp Ser Met Asp Tyr Asp Asp Ser Ser Ser
        620                 625                 630

TCT TAC TCC TCC CTT GGT GAC TTT GTC AGT GAA ATG ATG AAA TGT GAC       2272
Ser Tyr Ser Ser Leu Gly Asp Phe Val Ser Glu Met Met Lys Cys Asp
    635                 640                 645

ATT AAT GGT GAT ACT CCC AAT GTG GAC CCT CTG ACA CAT GCA GCA CTG       2320
Ile Asn Gly Asp Thr Pro Asn Val Asp Pro Leu Thr His Ala Ala Leu
650                 655                 660                 665

GGG GAT GCC AGC GAG GTG GAG ATT GAC GAG CTG CAG AAT CAG AAG GAA       2368
Gly Asp Ala Ser Glu Val Glu Ile Asp Glu Leu Gln Asn Gln Lys Glu
                670                 675                 680

GCA GAA GAG CCT GGC CCA GAC AGT GAG AAC TCT CAG GAA AAC CCC CCA       2416
Ala Glu Glu Pro Gly Pro Asp Ser Glu Asn Ser Gln Glu Asn Pro Pro
            685                 690                 695

CTG CGC TCC AGC TCT AGC ACC ACA GCC AGC AGC AGC CCC AGC ACT GTC       2464
Leu Arg Ser Ser Ser Ser Thr Thr Ala Ser Ser Ser Pro Ser Thr Val
        700                 705                 710

ATC CAC GGA GCC AAC TCT GAA CCT GCT GAC TCT ACG GAG ATG GAT GAT       2512
Ile His Gly Ala Asn Ser Glu Pro Ala Asp Ser Thr Glu Met Asp Asp
    715                 720                 725

AAG GCA GCA GTA GGC GTC TCC AAG CCC CTC CCT TCC GTG CCT CCC AGC       2560
Lys Ala Ala Val Gly Val Ser Lys Pro Leu Pro Ser Val Pro Pro Ser
730                 735                 740                 745

ATT GGC AAA TCG AAC ATG GAC AGA CGT CAG GCA GAA ATT GGA GAG GGG       2608
Ile Gly Lys Ser Asn Met Asp Arg Arg Gln Ala Glu Ile Gly Glu Gly
                750                 755                 760
```

| | | | | | | | | | | | | | | | | |
|---|---|---|---|---|---|---|---|---|---|---|---|---|---|---|---|---|
| TCA | GTG | CGC | CGG | CGA | ATC | TAT | GAC | AAT | CCA | TAC | TTC | GAG | CCC | CAA | TAT | 2656 |
| Ser | Val | Arg | Arg | Arg | Ile | Tyr | Asp | Asn | Pro | Tyr | Phe | Glu | Pro | Gln | Tyr | |
| | | | 765 | | | | 770 | | | | | | 775 | | | |
| GGC | TTT | CCC | CCT | GAG | GAA | GAT | GAG | GAT | GAG | CAG | GGG | GAA | AGT | TAC | ACT | 2704 |
| Gly | Phe | Pro | Pro | Glu | Glu | Asp | Glu | Asp | Glu | Gln | Gly | Glu | Ser | Tyr | Thr | |
| | | | 780 | | | | | 785 | | | | | 790 | | | |
| CCC | CGA | TTC | AGC | CAA | CAT | GTC | AGT | GGC | AAT | CGG | GCT | CAA | AAG | CTG | CTG | 2752 |
| Pro | Arg | Phe | Ser | Gln | His | Val | Ser | Gly | Asn | Arg | Ala | Gln | Lys | Leu | Leu | |
| | 795 | | | | | 800 | | | | | 805 | | | | | |
| CGG | CCC | AAC | AGC | TTG | AGA | CTG | GCA | AGT | GAC | TCA | GAT | GCA | GAG | TCA | GAC | 2800 |
| Arg | Pro | Asn | Ser | Leu | Arg | Leu | Ala | Ser | Asp | Ser | Asp | Ala | Glu | Ser | Asp | |
| 810 | | | | | 815 | | | | | 820 | | | | | 825 | |
| TCT | CGG | GCA | AGC | TCT | CCC | AAC | TCC | ACC | GTC | TCC | AAC | ACC | AGC | ACC | GAG | 2848 |
| Ser | Arg | Ala | Ser | Ser | Pro | Asn | Ser | Thr | Val | Ser | Asn | Thr | Ser | Thr | Glu | |
| | | | | 830 | | | | | 835 | | | | | 840 | | |
| GGC | TTC | GGG | GGC | ATC | ATG | TCT | TTT | GCC | AGC | AGC | CTC | TAT | CGG | AAC | CAC | 2896 |
| Gly | Phe | Gly | Gly | Ile | Met | Ser | Phe | Ala | Ser | Ser | Leu | Tyr | Arg | Asn | His | |
| | | | 845 | | | | | 850 | | | | | 855 | | | |
| AGT | ACC | AGC | TTC | AGT | CTT | TCA | AAC | CTC | ACA | CTG | CCC | ACC | AAA | GGT | GCC | 2944 |
| Ser | Thr | Ser | Phe | Ser | Leu | Ser | Asn | Leu | Thr | Leu | Pro | Thr | Lys | Gly | Ala | |
| | | 860 | | | | | 865 | | | | | 870 | | | | |
| CGA | GAG | AAG | GCC | ACG | CCC | TTC | CCC | AGT | CTG | AAA | GGA | AAC | AGG | AGG | GCG | 2992 |
| Arg | Glu | Lys | Ala | Thr | Pro | Phe | Pro | Ser | Leu | Lys | Gly | Asn | Arg | Arg | Ala | |
| 875 | | | | | 880 | | | | | 885 | | | | | | |
| TTA | GTG | GAT | CAG | AAG | TCA | TCT | GTC | ATT | AAA | CAC | AGC | CCA | ACA | GTG | AAA | 3040 |
| Leu | Val | Asp | Gln | Lys | Ser | Ser | Val | Ile | Lys | His | Ser | Pro | Thr | Val | Lys | |
| 890 | | | | | 895 | | | | | 900 | | | | | 905 | |
| AGA | GAA | CCT | CCA | TCA | CCC | CAG | GGT | CGA | TCC | AGC | AAT | TCT | AGT | GAG | AAC | 3088 |
| Arg | Glu | Pro | Pro | Ser | Pro | Gln | Gly | Arg | Ser | Ser | Asn | Ser | Ser | Glu | Asn | |
| | | | | 910 | | | | | 915 | | | | | 920 | | |
| CAG | CAG | TTC | CTG | AAG | GAG | GTG | GTG | CAC | AGC | GTG | CTG | GAC | GGC | CAG | GGA | 3136 |
| Gln | Gln | Phe | Leu | Lys | Glu | Val | Val | His | Ser | Val | Leu | Asp | Gly | Gln | Gly | |
| | | | 925 | | | | | 930 | | | | | 935 | | | |
| GTT | GGC | TGG | CTC | AAC | ATG | AAA | AAG | GTG | CGC | CGG | CTG | CTG | GAG | AGC | GAG | 3184 |
| Val | Gly | Trp | Leu | Asn | Met | Lys | Lys | Val | Arg | Arg | Leu | Leu | Glu | Ser | Glu | |
| | | | 940 | | | | | 945 | | | | | 950 | | | |
| CAG | CTG | CGA | GTC | TTT | GTC | CTG | AGC | AAG | CTG | AAC | CGC | ATG | GTG | CAG | TCA | 3232 |
| Gln | Leu | Arg | Val | Phe | Val | Leu | Ser | Lys | Leu | Asn | Arg | Met | Val | Gln | Ser | |
| | 955 | | | | | 960 | | | | | 965 | | | | | |
| GAG | GAC | GAT | GCC | CGG | CAG | GAC | ATC | ATC | CCG | GAT | GTG | GAG | ATC | AGT | CGG | 3280 |
| Glu | Asp | Asp | Ala | Arg | Gln | Asp | Ile | Ile | Pro | Asp | Val | Glu | Ile | Ser | Arg | |
| 970 | | | | | 975 | | | | | 980 | | | | | 985 | |
| AAG | GTG | TAC | AAG | GGA | ATG | TTA | GAC | CTC | CTC | AAG | TGT | ACA | GTC | CTC | AGC | 3328 |
| Lys | Val | Tyr | Lys | Gly | Met | Leu | Asp | Leu | Leu | Lys | Cys | Thr | Val | Leu | Ser | |
| | | | | 990 | | | | | 995 | | | | | 1000 | | |
| TTG | GAG | CAG | TCC | TAT | GCC | CAC | GCG | GGT | CTG | GGT | GGC | ATG | GCC | AGC | ATC | 3376 |
| Leu | Glu | Gln | Ser | Tyr | Ala | His | Ala | Gly | Leu | Gly | Gly | Met | Ala | Ser | Ile | |
| | | | 1005 | | | | | 1010 | | | | | 1015 | | | |
| TTT | GGG | CTT | TTG | GAG | ATT | GCC | CAG | ACC | CAC | TAC | TAT | AGT | AAA | GAA | CCA | 3424 |
| Phe | Gly | Leu | Leu | Glu | Ile | Ala | Gln | Thr | His | Tyr | Tyr | Ser | Lys | Glu | Pro | |
| | | | 1020 | | | | | 1025 | | | | | 1030 | | | |
| GAC | AAG | CGG | AAG | AGA | AGT | CCA | ACA | GAA | AGT | GTA | AAT | ACC | CCA | GTT | GGC | 3472 |
| Asp | Lys | Arg | Lys | Arg | Ser | Pro | Thr | Glu | Ser | Val | Asn | Thr | Pro | Val | Gly | |
| | 1035 | | | | | 1040 | | | | | 1045 | | | | | |
| AAG | GAT | CCT | GGC | CTA | GCT | GGG | CGG | GGG | GAC | CCA | AAG | GCT | ATG | GCA | CAA | 3520 |
| Lys | Asp | Pro | Gly | Leu | Ala | Gly | Arg | Gly | Asp | Pro | Lys | Ala | Met | Ala | Gln | |
| 1050 | | | | | 1055 | | | | | 1060 | | | | | 1065 | |
| CTG | AGA | GTT | CCA | CAA | CTG | GGA | CCT | CGG | GCA | CCA | AGT | GCC | ACA | GGA | AAG | 3568 |
| Leu | Arg | Val | Pro | Gln | Leu | Gly | Pro | Arg | Ala | Pro | Ser | Ala | Thr | Gly | Lys | |
| | | | | 1070 | | | | | 1075 | | | | | 1080 | | |

```
GGT CCT AAG GAA CTG GAC ACC AGA AGT TTA AAG GAA GAA AAT TTT ATA    3616
Gly Pro Lys Glu Leu Asp Thr Arg Ser Leu Lys Glu Glu Asn Phe Ile
        1085                1090                1095

GCA TCT ATT GGG CCT GAA GTA ATC AAA CCT GTC TTT GAC CTT GGT GAG    3664
Ala Ser Ile Gly Pro Glu Val Ile Lys Pro Val Phe Asp Leu Gly Glu
    1100                1105                1110

ACA GAG GAG AAA AAG TCC CAG ATC AGC GCA GAC AGT GGT GTG AGC CTG    3712
Thr Glu Glu Lys Lys Ser Gln Ile Ser Ala Asp Ser Gly Val Ser Leu
        1115                1120                1125

ACG TCT AGT TCC CAG AGG ACT GAT CAA GAC TCT GTC ATC GGC GTG AGT    3760
Thr Ser Ser Ser Gln Arg Thr Asp Gln Asp Ser Val Ile Gly Val Ser
1130                1135                1140                1145

CCA GCT GTT ATG ATC CGC AGC TCA AGT CAG GAT TCT GAA GTT AGC ACC    3808
Pro Ala Val Met Ile Arg Ser Ser Ser Gln Asp Ser Glu Val Ser Thr
                1150                1155                1160

GTG GTG AGT AAT AGC TCT GGA GAG ACC CTT GGA GCT GAC AGT GAC TTG    3856
Val Val Ser Asn Ser Ser Gly Glu Thr Leu Gly Ala Asp Ser Asp Leu
        1165                1170                1175

AGC AGC AAT GCA GGT GAT GGA CCA GGT GGC GAG GGC AGT GTT CAC CTG    3904
Ser Ser Asn Ala Gly Asp Gly Pro Gly Gly Glu Gly Ser Val His Leu
    1180                1185                1190

GCA AGC TCT CGG GGC ACT TTG TCT GAT AGT GAA ATT GAG ACC AAC TCT    3952
Ala Ser Ser Arg Gly Thr Leu Ser Asp Ser Glu Ile Glu Thr Asn Ser
1195                1200                1205

GCC ACA AGC ACC ATC TTT GGT AAA GCC CAC AGC TTG AAG CCA AGC ATA    4000
Ala Thr Ser Thr Ile Phe Gly Lys Ala His Ser Leu Lys Pro Ser Ile
1210                1215                1220                1225

AAG GAG AAG CTG GCA GGC AGC CCC ATT CGT ACT TCT GAA GAT GTG AGC    4048
Lys Glu Lys Leu Ala Gly Ser Pro Ile Arg Thr Ser Glu Asp Val Ser
                1230                1235                1240

CAG CGA GTC TAT CTC TAT GAG GGA CTC CTA GGC AAA GAG CGT TCT ACT    4096
Gln Arg Val Tyr Leu Tyr Glu Gly Leu Leu Gly Lys Glu Arg Ser Thr
        1245                1250                1255

TTA TGG GAC CAA ATG CAA TTC TGG GAA GAT GCC TTC TTA GAT GCT GTG    4144
Leu Trp Asp Gln Met Gln Phe Trp Glu Asp Ala Phe Leu Asp Ala Val
    1260                1265                1270

ATG TTG GAG AGA GAA GGG ATG GGT ATG GAC CAG GGT CCC AGG AA ATG    4192
Met Leu Glu Arg Glu Gly Met Gly Met Asp Gln Gly Pro Gln Glu Met
1275                1280                1285

ATC GAC AGG TAC CTG TCC CTT GGA GAA CAT GAC CGG AAG CGC CTG GAA    4240
Ile Asp Arg Tyr Leu Ser Leu Gly Glu His Asp Arg Lys Arg Leu Glu
1290                1295                1300                1305

GAT GAT GAA GAT CGC TTG CTG GCC ACA CTT CTG CAC AAC CTC ATC TCC    4288
Asp Asp Glu Asp Arg Leu Leu Ala Thr Leu Leu His Asn Leu Ile Ser
                1310                1315                1320

TAC ATG CTG CTG ATG AAG GTA AAT AAG AAT GAC ATC CGC AAG AAG GTG    4336
Tyr Met Leu Leu Met Lys Val Asn Lys Asn Asp Ile Arg Lys Lys Val
        1325                1330                1335

AGG CGC CTA ATG GGA AAG TCG CAC ATT GGG CTT GTG TAC AGC CAG CAA    4384
Arg Arg Leu Met Gly Lys Ser His Ile Gly Leu Val Tyr Ser Gln Gln
    1340                1345                1350

ATC AAT GAG GTG CTT GAT CAG CTG GCG AAC CTG AAT GGA CGC GAT CTC    4432
Ile Asn Glu Val Leu Asp Gln Leu Ala Asn Leu Asn Gly Arg Asp Leu
1355                1360                1365

TCT ATC TGG TCC AGT GGC AGC CGG CAC ATG AAG AAG CAG ACA TTT GTG    4480
Ser Ile Trp Ser Ser Gly Ser Arg His Met Lys Lys Gln Thr Phe Val
1370                1375                1380                1385

GTA CAT GCA GGG ACA GAT ACA AAC GGA GAT ATC TTT TTC ATG GAG GTG    4528
Val His Ala Gly Thr Asp Thr Asn Gly Asp Ile Phe Phe Met Glu Val
                1390                1395                1400
```

```
TGC GAT GAC TGT GTG GTG TTG CGT AGT AAC ATC GGA ACA GTG TAT GAG        4576
Cys Asp Asp Cys Val Val Leu Arg Ser Asn Ile Gly Thr Val Tyr Glu
        1405                    1410                    1415

CGC TGG TGG TAC GAG AAG CTC ATC AAC ATG ACC TAC TGT CCC AAG ACG        4624
Arg Trp Trp Tyr Glu Lys Leu Ile Asn Met Thr Tyr Cys Pro Lys Thr
        1420                    1425                    1430

AAG GTG TTG TGC TTG TGG CGT AGA AAT GGC TCT GAG ACC CAG CTC AAC        4672
Lys Val Leu Cys Leu Trp Arg Arg Asn Gly Ser Glu Thr Gln Leu Asn
        1435                    1440                    1445

AAG TTC TAT ACT AAA AAG TGT CGG GAG CTG TAC TAC TGT GTG AAG GAC        4720
Lys Phe Tyr Thr Lys Lys Cys Arg Glu Leu Tyr Tyr Cys Val Lys Asp
1450                    1455                    1460                    1465

AGC ATG GAG CGC GCT GCC GCC CGA CAG CAA AGC ATC AAA CCC GGA CCT        4768
Ser Met Glu Arg Ala Ala Ala Arg Gln Gln Ser Ile Lys Pro Gly Pro
                1470                    1475                    1480

GAA TTG GGT GGC GAG TTC CCT GTG CAG GAC CTG AAG ACT GGT GAG GGT        4816
Glu Leu Gly Gly Glu Phe Pro Val Gln Asp Leu Lys Thr Gly Glu Gly
                1485                    1490                    1495

GGC CTG CTG CAG GTG ACC CTG GAA GGG ATC AAC CTC AAA TTC ATG CAC        4864
Gly Leu Leu Gln Val Thr Leu Glu Gly Ile Asn Leu Lys Phe Met His
        1500                    1505                    1510

AAT CAG GTT TTC ATA GAG CTG AAT CAC ATT AAA AAG TGC AAT ACA GTT        4912
Asn Gln Val Phe Ile Glu Leu Asn His Ile Lys Lys Cys Asn Thr Val
        1515                    1520                    1525

CGA GGC GTC TTT GTC CTG GAG GAA TTT GTT CCT GAA ATT AAA GAA GTG        4960
Arg Gly Val Phe Val Leu Glu Glu Phe Val Pro Glu Ile Lys Glu Val
1530                    1535                    1540                    1545

GTG AGC CAC AAG TAC AAG ACA CCA ATG GCC CAC GAA ATC TGC TAC TCC        5008
Val Ser His Lys Tyr Lys Thr Pro Met Ala His Glu Ile Cys Tyr Ser
                1550                    1555                    1560

GTA TTA TGT CTC TTC TCG TAC GTG GCT GCA GTT CAT AGC AGT GAG GAA        5056
Val Leu Cys Leu Phe Ser Tyr Val Ala Ala Val His Ser Ser Glu Glu
                1565                    1570                    1575

GAT CTC AGA ACC CCG CCC CGG CCT GTC TCT AGC TGA TGGAGAGGGG            5102
Asp Leu Arg Thr Pro Pro Arg Pro Val Ser Ser  *
        1580                    1585

CTACGCAGCT GCCCCAGCCC AGGGCACGCC CCTGGCCCCT TGCTGTTCCC AAGTGCACGA     5162
TGCTGCTGTG ACTGAGGAGT GGATGATGCT CGTGTGTCCT CTGCAAGCCC CCTGCTGTGG     5222
CTTGGTTGGT TACCGGTTAT GTGTCCCTCT GAGTGTGTCT TGAGCGTGTC CACCTTCTCC     5282
CTCTCCACTC CAGAAGACC  AAACTGCCTT CCCCTCAGGG CTCAAGAATG TGTACAGTCT     5342
GTGGGGCCGG TGTGAACCCA CTATTTTGTG TCCTTGAGAC ATTTGTGTTG TGGTTCCTTG     5402
TCCTTGTCCC TGGCGTTATA ACTGTCCACT GCAAGAGTCT GGCTCTCCCT TCTCTGTGAC     5462
CCGGCATGAC TGGGCGCCTG GAGCAGTTTC ACTCTGTGAG GAGTGAGGGA ACCCTGGGGC     5522
TCACCCTCTC AGAGGAAGGG CACAGAGAGG AAGGGAAGAA TTGGGGGGCA GCCGGAGTGA     5582
GTGGCAGCCT CCCTGCTTCC TTCTGCATTC CAAGCCGGC  AGCTACTGCC CAGGGCCCGC     5642
AGTGTTGGCT GCTGCCTGCC ACAGCCTCTG TGACTGCAGT GGAGCGGCGA ATTCCCTGTG     5702
GCCTGCCACG CCTTCGGCAT CAGAGGATGG AGTGGTCGAG GCTAGTGGAG TCCCAGGGAC     5762
CGCTGGCTGC TCTGCCTGAG CATCAGGGAG GGGGCAGGAA AGACCAAGCT GGGTTTGCAC     5822
ATCTGTCTGC AGGCTGTCTC TCCAGGCACG GGGTGTCAGG AGGGAGAGAC AGCCTGGGTA     5882
TGGGCAAGAA ATGACTGTAA ATATTTCAGC CCCACATTAT TTATAGAAAA TGTACAGTTG     5942
TGTGAATGTG AAATAAATGT CCTCAACTCC CAAAAAAAAA AAAAAAAAAA AAAAAAAAAA     6002
```

( 2 ) INFORMATION FOR SEQ ID NO:16:

( i ) SEQUENCE CHARACTERISTICS:
        ( A ) LENGTH: 1588 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
Met Val Gln Lys Lys Lys Phe Cys Pro Arg Leu Leu Asp Tyr Leu Val
 1               5                  10                  15
Ile Val Gly Ala Arg His Pro Ser Ser Asp Ser Val Ala Gln Thr Pro
                20                  25                  30
Glu Leu Leu Arg Arg Tyr Pro Leu Glu Asp His Thr Glu Phe Pro Leu
            35                  40                  45
Pro Pro Asp Val Val Phe Phe Cys Gln Pro Glu Gly Cys Leu Ser Val
        50                  55                  60
Arg Gln Arg Arg Met Ser Leu Arg Asp Asp Thr Ser Phe Val Phe Thr
 65                  70                  75                  80
Leu Thr Asp Lys Asp Thr Gly Val Thr Arg Tyr Gly Ile Cys Val Asn
                85                  90                  95
Phe Tyr Arg Ser Phe Gln Lys Arg Ile Ser Lys Glu Lys Gly Glu Gly
            100                 105                 110
Gly Ala Gly Ser Arg Gly Lys Glu Gly Thr His Ala Thr Cys Ala Ser
        115                 120                 125
Glu Glu Gly Gly Thr Glu Ser Glu Ser Gly Ser Ser Leu Gln Pro
    130                 135                 140
Leu Ser Ala Asp Ser Thr Pro Asp Val Asn Gln Ser Pro Arg Gly Lys
145                 150                 155                 160
Arg Arg Ala Lys Ala Gly Ser Arg Ser Arg Asn Ser Thr Leu Thr Ser
                165                 170                 175
Leu Cys Val Leu Ser His Tyr Pro Phe Phe Ser Thr Phe Arg Glu Cys
            180                 185                 190
Leu Tyr Thr Leu Lys Arg Leu Val Asp Cys Cys Ser Glu Arg Leu Leu
        195                 200                 205
Gly Lys Lys Leu Gly Ile Pro Arg Gly Val Gln Arg Asp Thr Met Trp
    210                 215                 220
Arg Ile Phe Thr Gly Ser Leu Leu Val Glu Glu Lys Ser Ser Ala Leu
225                 230                 235                 240
Leu His Asp Leu Arg Glu Ile Glu Ala Trp Ile Tyr Arg Leu Leu Arg
                245                 250                 255
Ser Pro Val Pro Val Ser Gly Gln Lys Arg Val Asp Ile Glu Val Leu
            260                 265                 270
Pro Gln Glu Leu Gln Pro Ala Leu Thr Phe Ala Leu Pro Asp Pro Ser
        275                 280                 285
Arg Phe Thr Leu Val Asp Phe Pro Leu His Leu Pro Leu Glu Leu Leu
    290                 295                 300
Gly Val Asp Ala Cys Leu Gln Val Leu Thr Cys Ile Leu Leu Glu His
305                 310                 315                 320
Lys Val Val Leu Gln Ser Arg Asp Tyr Asn Ala Leu Ser Met Ser Val
                325                 330                 335
Met Ala Phe Val Ala Met Ile Tyr Pro Leu Glu Tyr Met Phe Pro Val
            340                 345                 350
Ile Pro Leu Leu Pro Thr Cys Met Ala Ser Ala Glu Gln Leu Leu Leu
        355                 360                 365
```

```
Ala Pro Thr Pro Tyr Ile Ile Gly Val Pro Ala Ser Phe Phe Leu Tyr
    370             375             380
Lys Leu Asp Phe Lys Met Pro Asp Asp Val Trp Leu Val Asp Leu Asp
385             390             395             400
Ser Asn Arg Val Ile Ala Pro Thr Asn Ala Glu Val Leu Pro Ile Leu
            405             410             415
Pro Glu Pro Glu Ser Leu Glu Leu Lys Lys His Leu Lys Gln Ala Leu
        420             425             430
Ala Ser Met Ser Leu Asn Thr Gln Pro Ile Leu Asn Leu Glu Lys Phe
        435             440             445
His Glu Gly Gln Glu Ile Pro Leu Leu Leu Gly Arg Pro Ser Asn Asp
    450             455             460
Leu Gln Ser Thr Pro Ser Thr Glu Phe Asn Pro Leu Ile Tyr Gly Asn
465             470             475             480
Asp Val Asp Ser Val Asp Val Ala Thr Arg Val Ala Met Val Arg Phe
            485             490             495
Phe Asn Ser Ala Asn Val Leu Gln Gly Phe Gln Met His Thr Arg Thr
            500             505             510
Leu Arg Leu Phe Pro Arg Pro Val Ala Phe Gln Ala Gly Ser Phe
        515             520             525
Leu Ala Ser Arg Pro Arg Gln Thr Pro Phe Ala Glu Lys Leu Ala Arg
530             535             540
Thr Gln Ala Val Glu Tyr Phe Gly Glu Trp Ile Leu Asn Pro Thr Asn
545             550             555             560
Tyr Ala Phe Gln Arg Ile His Asn Asn Met Phe Asp Pro Ala Leu Ile
            565             570             575
Gly Asp Lys Pro Lys Trp Tyr Ala His Gln Leu Gln Pro Ile His Tyr
            580             585             590
Arg Val Tyr Asp Ser Asn Ser Gln Leu Ala Glu Ala Leu Ser Val Pro
            595             600             605
Pro Glu Arg Asp Ser Asp Ser Glu Pro Thr Asp Asp Ser Gly Ser Asp
        610             615             620
Ser Met Asp Tyr Asp Asp Ser Ser Ser Tyr Ser Ser Leu Gly Asp
625             630             635             640
Phe Val Ser Glu Met Met Lys Cys Asp Ile Asn Gly Asp Thr Pro Asn
            645             650             655
Val Asp Pro Leu Thr His Ala Ala Leu Gly Asp Ala Ser Glu Val Glu
            660             665             670
Ile Asp Glu Leu Gln Asn Gln Lys Glu Ala Glu Glu Pro Gly Pro Asp
        675             680             685
Ser Glu Asn Ser Gln Glu Asn Pro Pro Leu Arg Ser Ser Ser Ser Thr
    690             695             700
Thr Ala Ser Ser Ser Pro Ser Thr Val Ile His Gly Ala Asn Ser Glu
705             710             715             720
Pro Ala Asp Ser Thr Glu Met Asp Asp Lys Ala Ala Val Gly Val Ser
            725             730             735
Lys Pro Leu Pro Ser Val Pro Pro Ser Ile Gly Lys Ser Asn Met Asp
        740             745             750
Arg Arg Gln Ala Glu Ile Gly Glu Gly Ser Val Arg Arg Ile Tyr
    755             760             765
Asp Asn Pro Tyr Phe Glu Pro Gln Tyr Gly Phe Pro Pro Glu Glu Asp
    770             775             780
Glu Asp Glu Gln Gly Glu Ser Tyr Thr Pro Arg Phe Ser Gln His Val
785             790             795             800
```

-continued

Ser Gly Asn Arg Ala Gln Lys Leu Leu Arg Pro Asn Ser Leu Arg Leu
            805                 810                 815

Ala Ser Asp Ser Asp Ala Glu Ser Asp Ser Arg Ala Ser Ser Pro Asn
        820                 825                 830

Ser Thr Val Ser Asn Thr Ser Thr Glu Gly Phe Gly Gly Ile Met Ser
            835                 840                 845

Phe Ala Ser Ser Leu Tyr Arg Asn His Ser Thr Ser Phe Ser Leu Ser
850                 855                 860

Asn Leu Thr Leu Pro Thr Lys Gly Ala Arg Glu Lys Ala Thr Pro Phe
865                 870                 875                 880

Pro Ser Leu Lys Gly Asn Arg Arg Ala Leu Val Asp Gln Lys Ser Ser
            885                 890                 895

Val Ile Lys His Ser Pro Thr Val Lys Arg Glu Pro Pro Ser Pro Gln
            900                 905                 910

Gly Arg Ser Ser Asn Ser Ser Glu Asn Gln Gln Phe Leu Lys Glu Val
            915                 920                 925

Val His Ser Val Leu Asp Gly Gln Gly Val Gly Trp Leu Asn Met Lys
        930                 935                 940

Lys Val Arg Arg Leu Leu Glu Ser Glu Gln Leu Arg Val Phe Val Leu
945                 950                 955                 960

Ser Lys Leu Asn Arg Met Val Gln Ser Glu Asp Asp Ala Arg Gln Asp
                965                 970                 975

Ile Ile Pro Asp Val Glu Ile Ser Arg Lys Val Tyr Lys Gly Met Leu
            980                 985                 990

Asp Leu Leu Lys Cys Thr Val Leu Ser Leu Glu Gln Ser Tyr Ala His
            995                 1000                1005

Ala Gly Leu Gly Gly Met Ala Ser Ile Phe Gly Leu Leu Glu Ile Ala
1010                1015                1020

Gln Thr His Tyr Tyr Ser Lys Glu Pro Asp Lys Arg Lys Arg Ser Pro
1025                1030                1035                1040

Thr Glu Ser Val Asn Thr Pro Val Gly Lys Asp Pro Gly Leu Ala Gly
                1045                1050                1055

Arg Gly Asp Pro Lys Ala Met Ala Gln Leu Arg Val Pro Gln Leu Gly
            1060                1065                1070

Pro Arg Ala Pro Ser Ala Thr Gly Lys Gly Pro Lys Glu Leu Asp Thr
        1075                1080                1085

Arg Ser Leu Lys Glu Glu Asn Phe Ile Ala Ser Ile Gly Pro Glu Val
    1090                1095                1100

Ile Lys Pro Val Phe Asp Leu Gly Glu Thr Glu Glu Lys Lys Ser Gln
1105                1110                1115                1120

Ile Ser Ala Asp Ser Gly Val Ser Leu Thr Ser Ser Ser Gln Arg Thr
                1125                1130                1135

Asp Gln Asp Ser Val Ile Gly Val Ser Pro Ala Val Met Ile Arg Ser
            1140                1145                1150

Ser Ser Gln Asp Ser Glu Val Ser Thr Val Val Ser Asn Ser Ser Gly
        1155                1160                1165

Glu Thr Leu Gly Ala Asp Ser Asp Leu Ser Ser Asn Ala Gly Asp Gly
    1170                1175                1180

Pro Gly Gly Glu Gly Ser Val His Leu Ala Ser Ser Arg Gly Thr Leu
1185                1190                1195                1200

Ser Asp Ser Glu Ile Glu Thr Asn Ser Ala Thr Ser Thr Ile Phe Gly
            1205                1210                1215

Lys Ala His Ser Leu Lys Pro Ser Ile Lys Glu Lys Leu Ala Gly Ser

```
                        1220                      1225                     1230
Pro  Ile  Arg  Thr  Ser  Glu  Asp  Val  Ser  Gln  Arg  Val  Tyr  Leu  Tyr  Glu
               1235                    1240                   1245

Gly  Leu  Leu  Gly  Lys  Glu  Arg  Ser  Thr  Leu  Trp  Asp  Gln  Met  Gln  Phe
1250                         1255                        1260

Trp  Glu  Asp  Ala  Phe  Leu  Asp  Ala  Val  Met  Leu  Glu  Arg  Glu  Gly  Met
1265                    1270                       1275                    1280

Gly  Met  Asp  Gln  Gly  Pro  Gln  Glu  Met  Ile  Asp  Arg  Tyr  Leu  Ser  Leu
                    1285                      1290                       1295

Gly  Glu  His  Asp  Arg  Lys  Arg  Leu  Glu  Asp  Asp  Glu  Asp  Arg  Leu  Leu
               1300                       1305                    1310

Ala  Thr  Leu  Leu  His  Asn  Leu  Ile  Ser  Tyr  Met  Leu  Leu  Met  Lys  Val
               1315                       1320                  1325

Asn  Lys  Asn  Asp  Ile  Arg  Lys  Lys  Val  Arg  Arg  Leu  Met  Gly  Lys  Ser
               1330                    1335                   1340

His  Ile  Gly  Leu  Val  Tyr  Ser  Gln  Gln  Ile  Asn  Glu  Val  Leu  Asp  Gln
1345                         1350                      1355                    1360

Leu  Ala  Asn  Leu  Asn  Gly  Arg  Asp  Leu  Ser  Ile  Trp  Ser  Ser  Gly  Ser
                    1365                       1370                      1375

Arg  His  Met  Lys  Lys  Gln  Thr  Phe  Val  Val  His  Ala  Gly  Thr  Asp  Thr
               1380                       1385                   1390

Asn  Gly  Asp  Ile  Phe  Phe  Met  Glu  Val  Cys  Asp  Asp  Cys  Val  Val  Leu
               1395                    1400                  1405

Arg  Ser  Asn  Ile  Gly  Thr  Val  Tyr  Glu  Arg  Trp  Trp  Tyr  Glu  Lys  Leu
1410                         1415                        1420

Ile  Asn  Met  Thr  Tyr  Cys  Pro  Lys  Thr  Lys  Val  Leu  Cys  Leu  Trp  Arg
1425                    1430                       1435                    1440

Arg  Asn  Gly  Ser  Glu  Thr  Gln  Leu  Asn  Lys  Phe  Tyr  Thr  Lys  Lys  Cys
                    1445                       1450                      1455

Arg  Glu  Leu  Tyr  Tyr  Cys  Val  Lys  Asp  Ser  Met  Glu  Arg  Ala  Ala  Ala
                    1460                       1465                      1470

Arg  Gln  Gln  Ser  Ile  Lys  Pro  Gly  Pro  Glu  Leu  Gly  Gly  Glu  Phe  Pro
               1475                       1480                    1485

Val  Gln  Asp  Leu  Lys  Thr  Gly  Glu  Gly  Gly  Leu  Leu  Gln  Val  Thr  Leu
1490                         1495                         1500

Glu  Gly  Ile  Asn  Leu  Lys  Phe  Met  His  Asn  Gln  Val  Phe  Ile  Glu  Leu
1505                         1510                        1515                    1520

Asn  His  Ile  Lys  Lys  Cys  Asn  Thr  Val  Arg  Gly  Val  Phe  Val  Leu  Glu
                    1525                      1530                    1535

Glu  Phe  Val  Pro  Glu  Ile  Lys  Glu  Val  Val  Ser  His  Lys  Tyr  Lys  Thr
                    1540                      1545                     1550

Pro  Met  Ala  His  Glu  Ile  Cys  Tyr  Ser  Val  Leu  Cys  Leu  Phe  Ser  Tyr
               1555                    1560                    1565

Val  Ala  Ala  Val  His  Ser  Ser  Glu  Glu  Asp  Leu  Arg  Thr  Pro  Pro  Arg
               1570                       1575                   1580

Pro  Val  Ser  Ser
1585
```

( 2 ) INFORMATION FOR SEQ ID NO:17:

( i ) SEQUENCE CHARACTERISTICS:
        ( A ) LENGTH: 2473 base pairs
        ( B ) TYPE: nucleic acid
        ( C ) STRANDEDNESS: double
        ( D ) TOPOLOGY: linear (i i) MOLECULE TYPE: cDNA (i x) FEATURE:
  (A) NAME/KEY: CDS
  (B) LOCATION: 14..2404

(x i) SEQUENCE DESCRIPTION: SEQ ID NO:17:

| | | | | | |
|---|---|---|---|---|---|
| CCGACGAGGA | GACATGGCGG | CGGCGCCGGT | AGCGGCTGGG | TCTGGAGCCG | GCCGAGGGAG | 60 |
| ACGGTCGGCA | GCCACAGTGG | CGGCTTGGGG | CGGATGGGGC | GGCCGGCCGC | GGCCTGGTAA | 120 |
| CATTCTGCTG | CAGCTGCGGC | AGGGCCAGCT | GACCGGCCGG | GGCCTGGTCC | GGGCGGTGCA | 180 |
| GTTCACTGAG | ACTTTTTTGA | CGGAGAGGGA | CAAACAATCC | AAGTGGAGTG | GAATTCCTCA | 240 |
| GCTGCTCCTC | AAGCTGCACA | CCACCAGCCA | CCTCCACAGT | GACTTTGTTG | AGTGTCAAAA | 300 |
| CATCCTCAAG | GAAATTTCTC | CTCTTCTCTC | CATGGAGGCT | ATGGCATTTG | TTACTGAAGA | 360 |
| GAGGAAACTT | ACCCAAGAAA | CCACTTATCC | AAATACTTAC | ATTTTTGACT | TGTTTGGAGG | 420 |
| TGTTGATCTT | CTTGTAGAAA | TTCTTATGAG | GCCTACGATC | TCTATCCGGG | GACAGAAACT | 480 |
| GAAAATAAGT | GATGAAATGT | CCAAGGACTG | CTTGAGTATC | CTGTATAATA | CCTGTGTCTG | 540 |
| TACAGAGGGA | GTTACAAAGC | GTTTGGCAGA | AAAGAATGAC | TTTGTGATCT | TCCTGTTTAC | 600 |
| ATTGATGACA | AGTAAGAAGA | CATTCTTACA | AACAGCAACC | CTCATTGAAG | ATATTTTAGG | 660 |
| TGTTAAAAAG | GAAATGATCC | GACTAGATGA | AGTCCCCAAT | CTGAGTTCCT | TAGTATCCAA | 720 |
| TTTCGATCAG | CAGCAGCTCG | CTAATTTCTG | CCGGATTCTG | GCTGTCACCA | TTTCAGAGAT | 780 |
| GGATACAGGG | AATGATGACA | AGCACACGCT | TCTTGCCAAA | AATGCTCAAC | AGAAGAAGAG | 840 |
| CTTGAGTTTG | GGGCCTTCTG | CAGCTGAAAT | CAATCAAGCG | GCCCTTCTCA | GCATTCCTGG | 900 |
| CTTTGTTGAG | CGGCTTTGCA | AACTGGCGAC | TCGAAAGGTG | TCAGAGTCAA | CGGGCACAGC | 960 |
| CAGCTTCCTT | CAGGAGTTGG | AAGAGTGGTA | CACATGGCTA | GACAATGCTT | GGTGCTAGA | 1020 |
| TGCCCTGATG | CGAGTGGCCA | ATGAGGAGTC | AGAGCACAAT | CAAGCCTCCA | TTGTGTTCCC | 1080 |
| TCCTCCAGGG | GCTTCTGAGG | AGAATGGCCT | GCCTCACACG | TCAGCCAGAA | CCCAGCTGCC | 1140 |
| CCAGTCAATG | AAGATTATGC | ATGAGATCAT | GTACAAACTG | GAAGTGCTCT | ATGTCCTCTG | 1200 |
| CGTGCTGCTG | ATGGGGCGTC | AGCGAAACCA | GGTTCACAGA | ATGATTGCAG | AGTTCAAGCT | 1260 |
| GATCCCTGGA | CTTAATAATT | TGTTTGACAA | ACTGATTTGG | AGGAAGCATT | CAGCATCTGC | 1320 |
| CCTTGTCCTC | CATGGTCACA | ACCAGAACTG | TGACTGTAGC | CCGGACATCA | CCTTGAAGAT | 1380 |
| ACAGTTTTTG | AGGCTTCTTC | AGAGCTTCAG | TGACCACCAC | GAGAACAAGT | ACTTGTTACT | 1440 |
| CAACAACCAG | GAGCTGAATG | AACTCAGTGC | CATCTCTCTC | AAGGCCAACA | TCCCTGAGGT | 1500 |
| GGAAGCTGTC | CTCAACACCG | ACAGGAGTTT | GGTGTGTGAT | GGGAAGAGGG | CTTATTAAC | 1560 |
| TCGTCTGCTG | CAGGTCATGA | AGAAGGAGCC | AGCAGAGTCG | TCTTTCAGGT | TTTGGCAAGC | 1620 |
| TCGGGCTGTG | GAGAGTTTCC | TCCGAGGGAC | CACCTCCTAT | GCAGACCAGA | TGTTCCTGCT | 1680 |
| GAAGCGAGGC | CTCTTGGAGC | ACATCCTTTA | CTGCATTGTG | GACAGCGAGT | GTAAGTCAAG | 1740 |
| GGATGTGCTC | CAGAGTTACT | TTGACCTCCT | GGGGGAGCTG | ATGAAGTTCA | ACGTTGATGC | 1800 |
| ATTCAAGAGA | TTCAATAAAA | ATATCAACAC | CGATGCAAAG | TTCCAGGTAT | TCCTGAAGCA | 1860 |
| GATCAACAGC | TCCCTGGTGG | ACTCCAACAT | GCTGGTGCGC | TGTGTCACTC | TGTCCCTGGA | 1920 |
| CCGATTTGAA | AACCAGGTGG | ATATGAAAGT | TGCCGAGGTA | CTGTCTGAAT | GCCGCCTGCT | 1980 |
| CGCCTACATA | TCCCAGGTGC | CCACGCAGAT | GTCCTTCCTC | TTCGCCCTCA | TCAACATCAT | 2040 |
| CCACGTGCAG | ACGCTGACCC | AGGAGAACGT | CAGCTGCCTC | AACACCAGCC | TGGTGATCCT | 2100 |
| GATGCTGGCC | CGACGGAAAG | AGCGGCTGCC | CCTGTACCTG | CGGCTGCTGC | AGCGGATGGA | 2160 |

| | | | | |
|---|---|---|---|---|
| GCACAGCAAG | AAGTACCCCG | GCTTCCTGCT | CAACAACTTC | CACAACCTGC | TGCGCTTCTG | 2220 |
| GCAGCAGCAC | TACCTGCACA | AGGACAAGGA | CAGCACCTGC | CTAGAGAACA | GCTCCTGCAT | 2280 |
| CAGCTTCTCA | TACTGGAAGG | AGACAGTGTC | CATCCTGTTG | AACCCGGACC | GGCAGTCACC | 2340 |
| CTCTGCTCTC | GTTAGCTACA | TTGAGGAGCC | CTACATGGAC | ATAGACAGGG | ACTTCACTGA | 2400 |
| GGAGTGACCT | TGGGCCAGGC | CTCGGGAGGC | TGCTGGGCCA | GTGTGGGTGA | GCGTGGGTAC | 2460 |
| GATGCCACAC | GCC | | | | | 2473 |

(2) INFORMATION FOR SEQ ID NO:18:

(i) SEQUENCE CHARACTERISTICS:
  (A) LENGTH: 797 amino acids
  (B) TYPE: amino acid
  (C) STRANDEDNESS:
  (D) TOPOLOGY: linear (ii) MOLECULE TYPE: protein (xi) SEQUENCE DESCRIPTION: SEQ ID NO:18:

```
Met Ala Ala Ala Pro Val Ala Ala Gly Ser Gly Ala Gly Arg Gly Arg
 1               5                  10                  15

Arg Ser Ala Ala Thr Val Ala Ala Trp Gly Gly Trp Gly Gly Arg Pro
                20                  25                  30

Arg Pro Gly Asn Ile Leu Leu Gln Leu Arg Gln Gly Gln Leu Thr Gly
            35                  40                  45

Arg Gly Leu Val Arg Ala Val Gln Phe Thr Glu Thr Phe Leu Thr Glu
        50                  55                  60

Arg Asp Lys Gln Ser Lys Trp Ser Gly Ile Pro Gln Leu Leu Leu Lys
65                  70                  75                  80

Leu His Thr Thr Ser His Leu His Ser Asp Phe Val Glu Cys Gln Asn
                85                  90                  95

Ile Leu Lys Glu Ile Ser Pro Leu Leu Ser Met Glu Ala Met Ala Phe
               100                 105                 110

Val Thr Glu Glu Arg Lys Leu Thr Gln Glu Thr Thr Tyr Pro Asn Thr
           115                 120                 125

Tyr Ile Phe Asp Leu Phe Gly Gly Val Asp Leu Leu Val Glu Ile Leu
       130                 135                 140

Met Arg Pro Thr Ile Ser Ile Arg Gly Gln Lys Leu Lys Ile Ser Asp
145                 150                 155                 160

Glu Met Ser Lys Asp Cys Leu Ser Ile Leu Tyr Asn Thr Cys Val Cys
               165                 170                 175

Thr Glu Gly Val Thr Lys Arg Leu Ala Glu Lys Asn Asp Phe Val Ile
           180                 185                 190

Phe Leu Phe Thr Leu Met Thr Ser Lys Lys Thr Phe Leu Gln Thr Ala
       195                 200                 205

Thr Leu Ile Glu Asp Ile Leu Gly Val Lys Lys Glu Met Ile Arg Leu
   210                 215                 220

Asp Glu Val Pro Asn Leu Ser Ser Leu Val Ser Asn Phe Asp Gln Gln
225                 230                 235                 240

Gln Leu Ala Asn Phe Cys Arg Ile Leu Ala Val Thr Ile Ser Glu Met
               245                 250                 255

Asp Thr Gly Asn Asp Asp Lys His Thr Leu Leu Ala Lys Asn Ala Gln
           260                 265                 270

Gln Lys Lys Ser Leu Ser Leu Gly Pro Ser Ala Ala Glu Ile Asn Gln
       275                 280                 285

Ala Ala Leu Leu Ser Ile Pro Gly Phe Val Glu Arg Leu Cys Lys Leu
```

```
              290                    295                    300
Ala  Thr  Arg  Lys  Val  Ser  Glu  Ser  Thr  Gly  Thr  Ala  Ser  Phe  Leu  Gln
305                      310                      315                      320

Glu  Leu  Glu  Glu  Trp  Tyr  Thr  Trp  Leu  Asp  Asn  Ala  Leu  Val  Leu  Asp
                         325                      330                      335

Ala  Leu  Met  Arg  Val  Ala  Asn  Glu  Glu  Ser  Glu  His  Asn  Gln  Ala  Ser
                    340                      345                      350

Ile  Val  Phe  Pro  Pro  Pro  Gly  Ala  Ser  Glu  Glu  Asn  Gly  Leu  Pro  His
               355                      360                      365

Thr  Ser  Ala  Arg  Thr  Gln  Leu  Pro  Gln  Ser  Met  Lys  Ile  Met  His  Glu
370                      375                      380

Ile  Met  Tyr  Lys  Leu  Glu  Val  Leu  Tyr  Val  Leu  Cys  Val  Leu  Leu  Met
385                      390                      395                      400

Gly  Arg  Gln  Arg  Asn  Gln  Val  His  Arg  Met  Ile  Ala  Glu  Phe  Lys  Leu
                    405                      410                      415

Ile  Pro  Gly  Leu  Asn  Asn  Leu  Phe  Asp  Lys  Leu  Ile  Trp  Arg  Lys  His
               420                      425                      430

Ser  Ala  Ser  Ala  Leu  Val  Leu  His  Gly  His  Asn  Gln  Asn  Cys  Asp  Cys
          435                      440                      445

Ser  Pro  Asp  Ile  Thr  Leu  Lys  Ile  Gln  Phe  Leu  Arg  Leu  Leu  Gln  Ser
450                      455                      460

Phe  Ser  Asp  His  His  Glu  Asn  Lys  Tyr  Leu  Leu  Leu  Asn  Asn  Gln  Glu
465                      470                      475                      480

Leu  Asn  Glu  Leu  Ser  Ala  Ile  Ser  Leu  Lys  Ala  Asn  Ile  Pro  Glu  Val
               485                      490                      495

Glu  Ala  Val  Leu  Asn  Thr  Asp  Arg  Ser  Leu  Val  Cys  Asp  Gly  Lys  Arg
               500                      505                      510

Gly  Leu  Leu  Thr  Arg  Leu  Leu  Gln  Val  Met  Lys  Lys  Glu  Pro  Ala  Glu
          515                      520                      525

Ser  Ser  Phe  Arg  Phe  Trp  Gln  Ala  Arg  Ala  Val  Glu  Ser  Phe  Leu  Arg
530                      535                      540

Gly  Thr  Thr  Ser  Tyr  Ala  Asp  Gln  Met  Phe  Leu  Leu  Lys  Arg  Gly  Leu
545                      550                      555                      560

Leu  Glu  His  Ile  Leu  Tyr  Cys  Ile  Val  Asp  Ser  Glu  Cys  Lys  Ser  Arg
               565                      570                      575

Asp  Val  Leu  Gln  Ser  Tyr  Phe  Asp  Leu  Leu  Gly  Glu  Leu  Met  Lys  Phe
               580                      585                      590

Asn  Val  Asp  Ala  Phe  Lys  Arg  Phe  Asn  Lys  Asn  Ile  Asn  Thr  Asp  Ala
          595                      600                      605

Lys  Phe  Gln  Val  Phe  Leu  Lys  Gln  Ile  Asn  Ser  Ser  Leu  Val  Asp  Ser
     610                      615                      620

Asn  Met  Leu  Val  Arg  Cys  Val  Thr  Leu  Ser  Leu  Asp  Arg  Phe  Glu  Asn
625                      630                      635                      640

Gln  Val  Asp  Met  Lys  Val  Ala  Glu  Val  Leu  Ser  Glu  Cys  Arg  Leu  Leu
               645                      650                      655

Ala  Tyr  Ile  Ser  Gln  Val  Pro  Thr  Gln  Met  Ser  Phe  Leu  Phe  Arg  Leu
               660                      665                      670

Ile  Asn  Ile  Ile  His  Val  Gln  Thr  Leu  Thr  Gln  Glu  Asn  Val  Ser  Cys
          675                      680                      685

Leu  Asn  Thr  Ser  Leu  Val  Ile  Leu  Met  Leu  Ala  Arg  Arg  Lys  Glu  Arg
     690                      695                      700

Leu  Pro  Leu  Tyr  Leu  Arg  Leu  Leu  Gln  Arg  Met  Glu  His  Ser  Lys  Lys
705                      710                      715                      720
```

-continued

| | | | | | | | | | | | | | | | |
|---|---|---|---|---|---|---|---|---|---|---|---|---|---|---|---|
| Tyr | Pro | Gly | Phe | Leu<br>725 | Leu | Asn | Asn | Phe | His<br>730 | Asn | Leu | Leu | Arg | Phe<br>735 | Trp |
| Gln | Gln | His | Tyr<br>740 | Leu | His | Lys | Asp | Lys<br>745 | Asp | Ser | Thr | Cys | Leu<br>750 | Glu | Asn |
| Ser | Ser | Cys<br>755 | Ile | Ser | Phe | Ser | Tyr<br>760 | Trp | Lys | Glu | Thr | Val<br>765 | Ser | Ile | Leu |
| Leu | Asn<br>770 | Pro | Asp | Arg | Gln | Ser<br>775 | Pro | Ser | Ala | Leu | Val<br>780 | Ser | Tyr | Ile | Glu |
| Glu<br>785 | Pro | Tyr | Met | Asp | Ile<br>790 | Asp | Arg | Asp | Phe | Thr<br>795 | Glu | Glu | | | |

What is claimed is:

1. A composition comprising an isolated polynucleotide encoding a protein having TNF-R1-DD ligand protein activity, wherein said polynucleotide is selected from the group consisting of:

(a) a polynucleotide comprising the nucleotide sequence of SEQ ID NO:1 from nucleotide 2 to nucleotide 1231;

(b) a polynucleotide comprising a fragment of the nucleotide sequence of SEQ ID NO:1;

(c) a polynucleotide encoding an TNF-R1-DD ligand protein comprising the amino acid sequence of SEQ ID NO:2; and (d) a polynucleotide encoding an TNF-R1-DD ligand protein comprising a fragment of the amino acid sequence of SEQ ID NO:2.

2. A composition of claim 1 wherein said polynucleotide is operably linked to an expression control sequence.

3. A host cell transformed with a composition of claim 2.

4. The host cell of claim 3, wherein said cell is a mammalian cell.

5. A process for producing an TNF-R1-DD ligand protein, which comprises:

(a) growing a culture of the host cell of claim 3 in a suitable culture medium; and (b) purifying the TNF-R1-DD ligand protein from the culture.

6. A composition comprising an isolated polynucleotide encoding a protein having TNF-R1-DD ligand protein activity, wherein said polynucleotide is selected from the group consisting of:

(a) a polynucleotide comprising the nucleotide sequence of SEQ ID NO:11 from nucleotide 2 to nucleotide 1822;

(b) a polynucleotide comprising a fragment of the nucleotide sequence of SEQ ID NO:11;

(c) a polynucleotide encoding an TNF-R1-DD ligand protein comprising the amino acid sequence of SEQ ID NO:12; and (d) a polynucleotide encoding an TNF-R1-DD ligand protein comprising a fragment of the amino acid sequence of SEQ ID NO:12.

7. A composition of claim 6 wherein said polynucleotide is operably linked to an expression control sequence.

8. A host cell transformed with a composition of claim 7.

9. The host cell of claim 8, wherein said cell is a mammalian cell.

10. A process for producing an TNF-R1-DD ligand protein, which comprises:

(a) growing a culture of the host cell of claim 8 in a suitable culture medium; and (b) purifying the TNF-R1-DD ligand protein from the culture.

11. A composition comprising an isolated polynucleotide encoding a protein having TNF-R1-DD ligand protein activity, wherein said polynucleotide is selected from the group consisting of:

(a) a polynucleotide comprising the nucleotide sequence of SEQ ID NO:15 from nucleotide 326 to nucleotide 5092;

(b) a polynucleotide comprising a fragment of the nucleotide sequence of SEQ ID NO:15;

(c) a polynucleotide encoding an TNF-R1-DD ligand protein comprising the amino acid sequence of SEQ ID NO:16; and (d) a polynucleotide encoding an TNF-R1-DD ligand protein comprising a fragment of the amino acid sequence of SEQ ID NO:16.

12. A composition of claim 11 wherein said polynucleotide is operably linked to an expression control sequence.

13. A host cell transformed with a composition of claim 12.

14. The host cell of claim 13, wherein said cell is a mammalian cell.

15. A process for producing an TNF-R1-DD ligand protein, which comprises:

(a) growing a culture of the host cell of claim 13 in a suitable culture medium; and (b) purifying the TNF-R1-DD ligand protein from the culture.

16. A composition comprising an isolated polynucleotide encoding a protein having TNF-R1-DD ligand protein activity, wherein said polynucleotide is selected from the group consisting of:

(a) a polynucleotide comprising the nucleotide sequence of SEQ ID NO:1 from nucleotide 2 to nucleotide 1231; and (b) a polynucleotide encoding an TNF-R1-DD ligand protein comprising the amino acid sequence of SEQ ID NO:2.

17. The composition of claim 16 wherein said polynucleotide comprises the nucleotide sequence of SEQ ID NO:1 from nucleotide 2 to nucleotide 1231.

18. The composition of claim 16 wherein said polynucleotide encodes an TNF-R 1-DD ligand protein comprising the amino acid sequence of SEQ ID NO:2.

19. A composition comprising an isolated polynucleotide encoding a protein having TNF-R1-DD ligand protein activity, wherein said polynucleotide is selected from the group consisting of:

(a) a polynucleotide comprising the nucleotide sequence of SEQ ID NO:11 from nucleotide 2 to nucleotide 1822; and (b) a polynucleotide encoding an TNF-R1-DD ligand protein comprising the amino acid sequence of SEQ ID NO:12.

20. The composition of claim 19 wherein the polynucleotide comprises the nucleotide sequence of SEQ ID NO:11 from nucleotide 2 to nucleotide 1822.

21. The composition of claim 19 wherein the polynucleotide encodes an TNF-R 1-DD ligand protein comprising the amino acid sequence of SEQ ID NO:12.

22. A composition comprising an isolated polynucleotide encoding a protein having TNF-R1-DD ligand protein activity, wherein said polynucleotide is selected from the group consisting of:

(a) a polynucleotide comprising the nucleotide sequence of SEQ ID NO:15 from nucleotide 326 to nucleotide 5092; and (b) a polynucleotide encoding an TNF-R1-DD ligand protein comprising the amino acid sequence of SEQ ID NO:16.

23. The composition of claim 22 wherein the polynucleotide comprises the nucleotide sequence of SEQ ID NO:15 from nucleotide 326 to nucleotide 5092.

24. The composition of claim 22 wherein the polynucleotide encodes an TNF-R 1-DD ligand protein comprising the amino acid sequence of SEQ ID NO:16.

* * * * *